(12) United States Patent
Uppenberg

(10) Patent No.: US 6,403,330 B1
(45) Date of Patent: Jun. 11, 2002

(54) METHOD OF STRUCTURE-BASED DRUG DESIGN USING A CRYSTALLINE FORM OF ACTIVATED TRAP

(75) Inventor: Jonas Uppenberg, Uppsala (SE)

(73) Assignee: Biovitrum AB, Stockholm (SE)

( * ) Notice: Subject to any disclaimer, the term of this patent is extended or adjusted under 35 U.S.C. 154(b) by 0 days.

(21) Appl. No.: 09/921,318

(22) Filed: Aug. 2, 2001

Related U.S. Application Data

(62) Division of application No. 09/451,900, filed on Dec. 1, 1999, now Pat. No. 6,329,184.
(60) Provisional application No. 60/113,304, filed on Dec. 22, 1998.

(30) Foreign Application Priority Data

Dec. 18, 1998 (SE) ............................................... 9804418

(51) Int. Cl.$^7$ ............................. C12N 9/16; C12Q 1/42; A61K 38/46
(52) U.S. Cl. ......................... 435/21; 435/196; 424/94.6
(58) Field of Search ......................... 435/195, 21, 196; 424/94.6

(56) References Cited

PUBLICATIONS

Klabunde et al, *Journal of Molecular Biology,* 259;737–748 (1996).
Sträter et al, *Science,* 268:1489–1492 (1995).
Chemical Abstract No. 128:291819 of *Bioinorg. Chem.,* 412–425 (1997).
Chemical Abstract No. 127:199122 of *J. Chem. Soc.,* Dalton Trans., 12:2109–2112 (1997).
Chemical Abstract No. 123:221376 of NATO ASI Ser., C (1995), 459 *Bioinorganic Chemistry,* 371–84.
Ek–Rylander et al, *Biochemical Journal,* 321 (2):305–311 (1997), and Derwent abstract thereof.
Lindqvist et al, *Journal of Molecular Biology,* 291:135–147 (1999).
Guddat et al, *Structure,* 7(7):757–767 (1999).
Uppenberg et al, *Journal of Molecular Biology,* 290:201–211 (1999).
Hayman et al, *The Journal of Biological Chemistry,* 269(2):1294–1300 (1994).
Allen et al, *Journal of Bone and Mineral Research,* 4(1):47–55 (1989).
Marshall et al, *Archives of Biochemistry and Biophysics,* 345 (2):230–236 (1997).
Yin et al, J. Chem. Soc., Dalton Trans., 2109–2112 (1997).
McPherson, *Preparation and Analysis of Protein Crystals,* John Wiley & Sons, 102–106 (1982).

*Primary Examiner*—David M. Naff
*Assistant Examiner*—Mike Meller
(74) *Attorney, Agent, or Firm*—Fish & Richardson P.C.

(57) ABSTRACT

A crystalline form of mammalian TRAP (tartrate-resistant and purple acid phosphatase) is described. The enzyme is activated by cleavage prior to crystallization with a protease and the crystalline form of the mammalian TRAP is capable of being used for X-ray studies.

24 Claims, 6 Drawing Sheets

Figure 2:
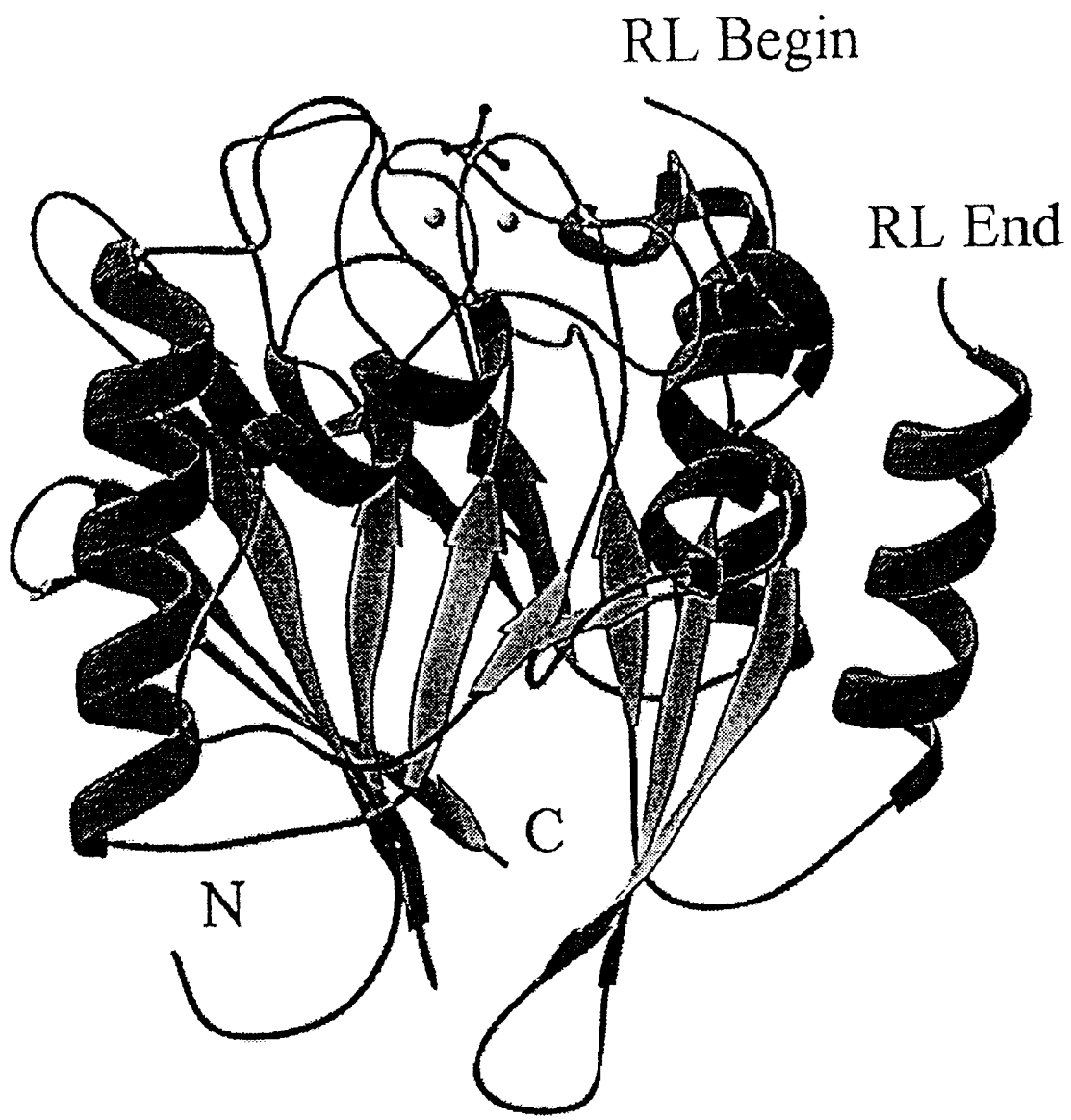

| | | |
|---|---|---|
| 1 | TAPASTLRFVAVGDWGGVPNAPFHTAREMANAKEIARTVQIMGADFIMSLGDNFYFTGVH | 60 |
| 61 | DANDKRFQETFEDVFSDRALRNIPWYVLAGNHDHLGNVSAQIAYSKISKRWNFPSPYYRL | 120 |
| 121 | RFKVPRSNITVAIFMLDTVMLCGNSDDFVSQQPEMPRDLGVARTQLSWLKKQLAAAKEDY | 180 |
| 181 | VLVAGHYPIWSIAEHGPTRCLVKNLRPLLAAYGVTAYLCGHDHNLQYLQDENGVGYVLSG | 240 |
| 241 | AGNFMDPSVRHQRKVPNGYLRFHYGSEDSLGGFTYVEIGSKEMSITYVEASGKSLFKTSL | 300 |
| 301 | PRRPRP | |

Figure 1

METHOD OF STRUCTURE-BASED DRUG DESIGN USING A CRYSTALLINE FORM OF ACTIVATED TRAP

The present application is a divisional of U.S. application Ser. No. 09/451,900, filed Dec. 1, 1999, which issued as U.S. Pat. No. 6,329,184, on Dec. 11, 2001, which claims priority to U.S. Provisional Application Ser. No. 60/113,304, filed Dec. 22, 1998, and Swedish Patent Application No. 9804418-3, filed Dec. 18, 1998. These applications are incorporated herein by reference in their entirety.

The invention relates to crystalline form of TRAP (tartrate-resistant and purple acid phosphatases), which is activated by cleavage. The TRAP is preferably human or rat TRAP. The atomic structural coordinates are given as well as the conserved surface which is created by special atoms, relevant for the design of modulators or inhibitors of the human TRAP. This crystalline form of activated TRAP can be used for structure-based drug design for specific modulator, activator or inhibitor of TRAP activity, useful in the treatment of diseases or degenerative conditions resulting in increased bone resorption, such as tissue damages, bone metabolic disorders, osteoporosis.

BACKGROUND

Tartrate resistant purple acid phosphatase (TRAP or PAP) is a mammalian di-iron containing enzyme highly expressed in a limited number of tissues. In humans and rodents it is primarily present in cells responsible for bone resorption, osteoclasts, and in macrophages of spleen, liver and lung.

Normal bone function requires a turnover of bone. Bone is constantly being rebuilt by cycles of resorption and formation which means that formation is closely linked to resorption (a phenomenon referred to as coupling).

TRAP is an enzyme expressed predominantly in bone resorbing cells (osteoclasts). Investigations in TRAP knockout mice show that the resorption process is disrupted so that, with increasing age, TRAP knockout mice become osteopetrotic, i.e. have an increased bone mineral content and more dense bone is formed. Osteoclasts prepared from these animals are functional and do resorb bone but to a lesser extent than wild type mouse osteoclasts.

Phosphatases are enzymes that remove organic phosphates from proteins. The mammalian Purple Acid Phosphatases (PAPs), a group of enzymes to which Tartrate Resistant and purple Acid Phosphatase (TRAP) belongs, are characterized by a binuclear iron center at the active site.

The binuclear iron center, low pH optimum ($\approx 5$), high isoelectric point ($\approx 9$) and insensitivity to inhibition by L(+) tartrate are features of TRAP that may be involved in the apparent substrate specificity at the low pH in the osteoclastic resorption area. The TRAP enzyme is a cationic glycoprotein with a molecular mass of 35 kD. The rat TRAP is a protein with a monomeric 306 amino acid peptide structure. See FIG. 1. The peptide sequence of rat bone TRAP displays 89–94% homology to TRAP enzyme of the human placenta, bovine spleen, and uteroferrin.

TRAP hydrolyzes aryl phosphates, nucleoside di- and triphosphates, pyrophosphate and phosphoproteins. Its physiological role remains unclear but TRAP may mediate dephosphorylation of bone matrix proteins such as osteopontin and bone sialoprotein. Dephosphorylation of bone matrix proteins enables osteoclasts to migrate over the bone surface and TRAP is therefore likely to be involved in the attachment of osteoclasts to the bone surface.

In humans and rats, PAP enzymes are highly expressed in certain cells of the monocytemacrophage lineage, such as the bone-resorbing osteoclasts and certain activated macrophages in spleen, liver and lung [1–4], and TRAP has since long been used as a histochemical marker for these cells. Given the broad substrate specificity of PAP enzymes, it is conceivable that other factors, such as local availability and proper compartmentalisation of PAPs with their potential substrates, are other important factors in determining the physiological action of PAPs in biological systems.

The cDNA sequences of TRAP/PAP enzymes from different species and organs all indicate that these enzymes are translated as a single polypeptide of around 35 kDa [5–8]. This contrasts with the predominantly two subunit structure, consisting of a 20–23 kDa N-terminal domain linked through a disulphide bond to a 15–17 kDa C-terminal domain, observed in purified enzyme preparations from a variety of sources including human and rat bone [9–10], giant cell tumors [11] and normal and pathological spleen [12–14]. In contrast, uteroferrin purified from endometrial secretions are mostly in the single subunit form [12, 15] as are the recombinant PAPs generated by overexpression using the Baculovirus system [16, 17, 18]. Orlando et al [13] managed to separate the monomeric and two-subunit variants of PAP from bovine spleen, and demonstrated a markedly higher specific enzyme activity associated with the two subunit form. Moreover, digestion of the single subunit form with the serine proteases trypsin or chymotrypsin generated the 23 kDa and 15 kDa disulfide-linked fragments characteristic of the two subunit form together with a significant enhancement of enzyme activity. Similar nicking and activation of the non-cleaved purified recombinant human and mouse PAPs were noted upon prolonged storage [17].

Purple acid phosphatases (PAPs) are acid metallohydrolases that contain a binuclear $Fe^{3+}M^{2+}$ center in their active site, where M=Fe or Zn [19–22]. In mammals, these enzymes are also referred to as tartrate-resistant acid phosphatases (TRAPs) (EC 3.1.3.2) or type 5 acid phosphatases [23]. TRAPs are iron-containing, monomeric glycoproteins with molecular weights of around 35,000 Da [24]. The deduced amino acid sequences of human, rat and mouse TRAPs shows a high degree of identity to the mammalian members of the PAP family, e.g uteroferrin (Uf) and bovine spleen PAP[5–7]. Recently, EPR spectroscopic analysis of rat recombinant TRAPs[16] have provided compelling evidence that this enzyme belong to the purple acid phosphatase family.

Mammalian PAPs contain a FeFe centre, while a plant PAP from red kidney beans (KBPAP) instead has a FeZn center [25]. The anti-ferromagnetically spin-coupled binuclear iron centre of the mammalian PAPs exists in two stable interconvertible states: pink, reduced, EPR-visible and enzymatically active, with a mixed-valent $Fe^{2+}$-$Fe^{3+}$ cluster; and purple, oxidized, EPR-silent and catalytically inactive, with the binuclear pair as $Fe^{3+}$-$Fe^{3+}$ [21, 26–27]. In contrast, the plant enzyme with a mixed-valent $Zn^{2+}$-$Fe^{3+}$ centre is constitutively active [28]. The M(2+) site in the PAPs can harbour either $Zn^{2+}$ or $Fe^{2+}$ without alteration of enzyme activity or spectral properties [28–30]. KBPAP is the only PAP whose X-ray structure has been determined. [17] The active site of KBPAP consists of an iron and a zinc ion bridged by an aspartate and probably a hydroxide. The $Fe^{3+}$ site is coordinated by tyrosine, histidine and aspartate, while the $Zn^{2+}$ site is coordinated by two histidines and an asparagine [17,31]. One solvent molecule is probably bound to each metal ion. Kidney bean PAP is a homodimeric protein with a molecular weight of around 110,000 Da, and exhibits a low overall sequence homology to the mammalian PAPs [32]. However, an alignment of the sequences of Uf and KBPAP displays an identical positioning of the amino acid residues ligating the di-metal centre [31,32]. Moreover, the mammalian protein phosphatases calcineurin (type 2B) [1–2] and protein phosphatase type 1 (PP-1) [3–4] both contain a di-nuclear metal centre and also reveal a striking similarity to the plant PAP enzyme in the coordination environments of the active site, except for the absence of the tyrosine ligand. These two latter enzymes are serine/threonine protein phosphatases, suggesting that also PAPs function as protein phosphatases. A sequence motif, DXH(X)nGDXXD(X)nGNHD/E, incorporating most of the metal-coordinating amino acids found in the PAP and PP structures so far identified has recently been identified also in a large group of phosphoesterases, including other phosphomonoesterases, nucleotide phosphatases and nucleases, from plants, bacteria and animal cells [8–11]. This phosphoesterase signature motif is represented at the secondary structure level as a β-α-β-α-β-fold that serves to position the two metal ions at the active site with four of the metal ligands provided by loop residues between each β-sheet and α-helix. The importance of this motif has been confirmed by site-directed mutagenesis studies [12–13]. Furthermore, the PAP members are related to a superfamily of μ-(hydr)oxo-bridged binuclear iron proteins, including hemerythrin, R2-subunit of ribonucleotide reductase, methane monooxygenase hydroxylase and others [15]. All members of this superfamily of iron-oxygen proteins contain a binuclear iron center but have different functions.

No crystallisation of TRAP, nor of actived TRAP has earlier been performed. The crystal form of the new active form of TRAP is of great use in the screening for specific modulators, activators or inhibitor of TRAP activity. Such specific modulators, activators or inhibitor are useful in the treatment of diseases or degenerative conditions resulting in increased bone resorption, such as tissue damages, bone metabolic disorders, osteoporosis.

FIGURES

FIG. 1. The amino acid sequence of rat TRAP, Sequence listing No 1.

FIG. 2. A view of TRAP.

Figure 3:
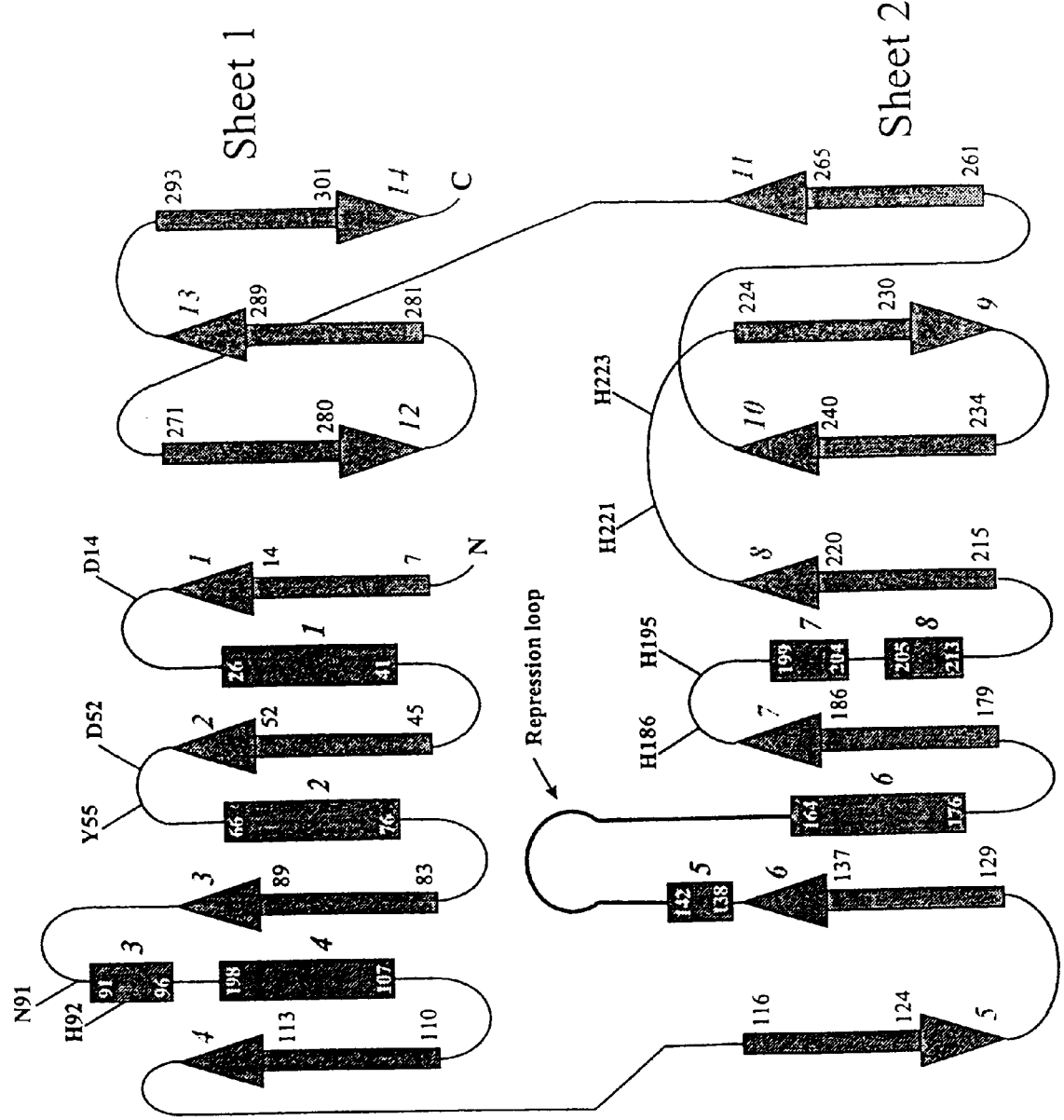

FIG. 3. Secondary structure diagram of the catalytic domains of TRAP

Figure 4:
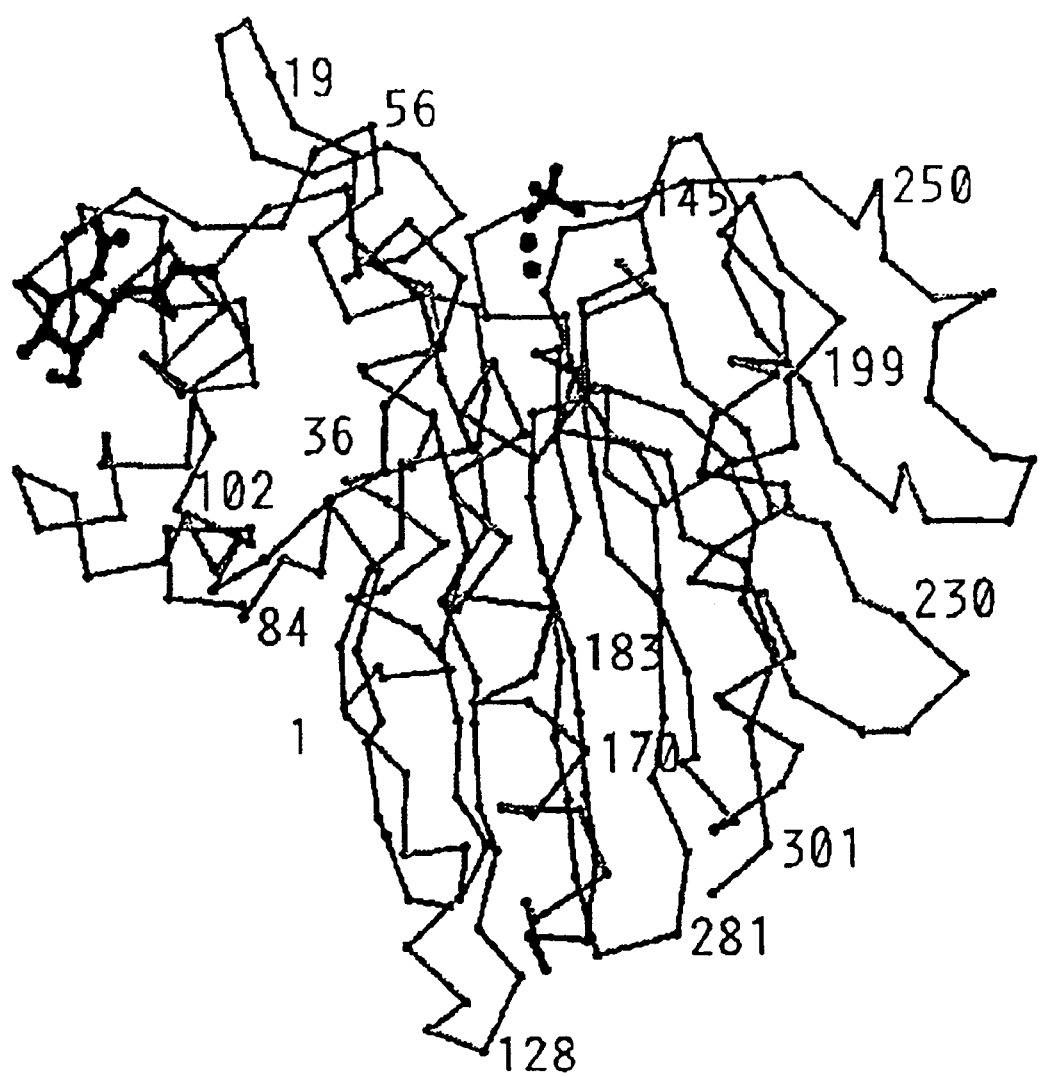

FIG. 4. A tracing of α-carbons in TRAP.

Figure 5:
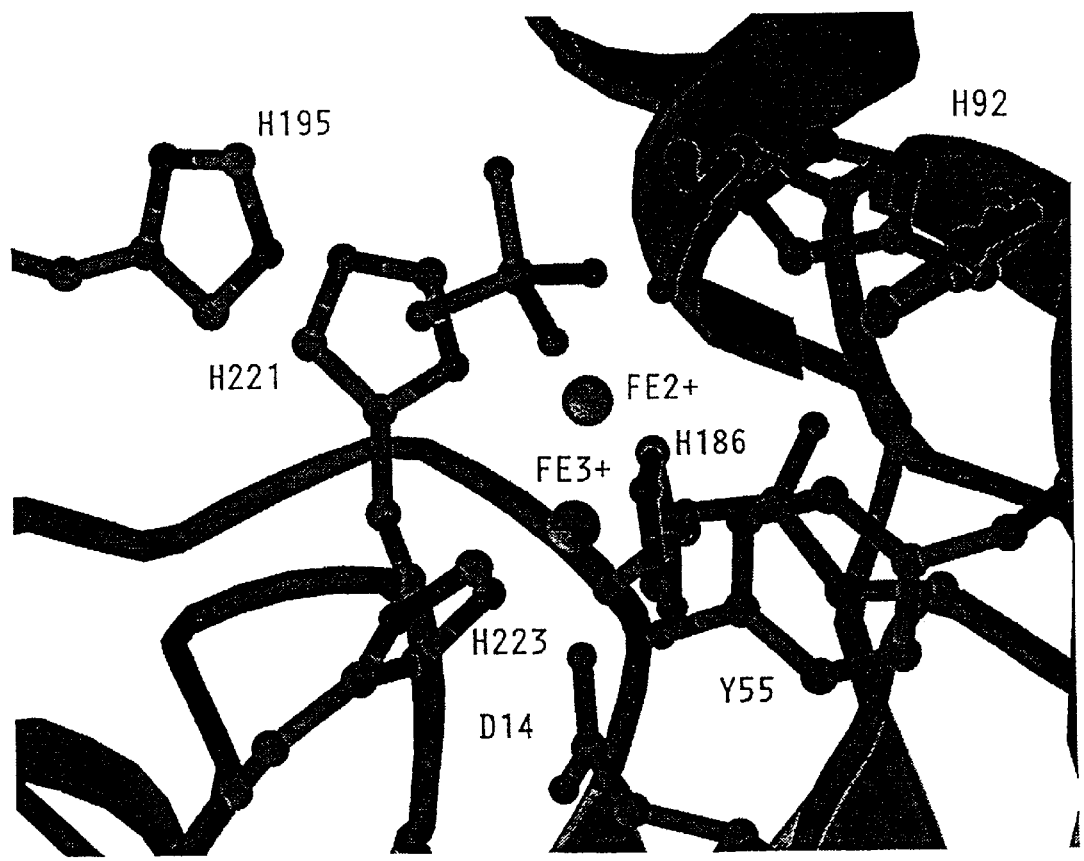

FIG. 5. A view of the active site of TRAP.

Figure 6:
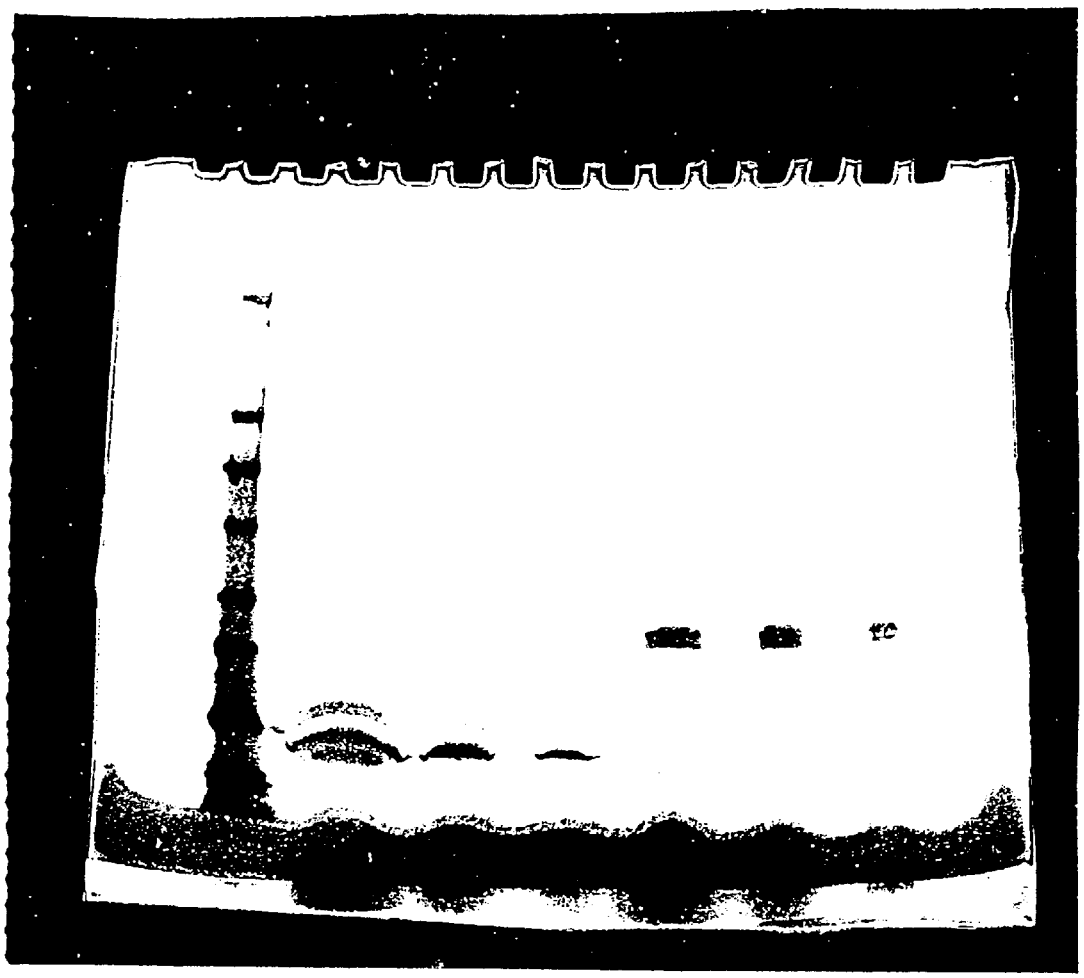

FIG. 6. SDS-PAGE gel showing the contents of the crystal containing drops.

THE INVENTION

The present invention relates to crystalline form of TRAP (tartrate-resistant and purple acid phosphatases), which is activated by cleavage, preferably human or rat TRAP (Sequence listing No 1). The atomic structural coordinates are given in Table 2. The conserved surface which is created by special atoms is important and crucial for the design of modulators or inhibitors of the human TRAP.

This crystalline form of activated TRAP can be used for structure-based drug design for specific modulator, activator or inhibitor of TRAP activity, useful in the treatment of diseases or degenerative conditions resulting in increased bone resorption, such as tissue damages, bone metabolic disorders, osteoporosis.

This claimed crystal form of TRAP is a cleaved form. The cleavage of TRAP increases activity and gives the TRAP, which here is called activated TRAP. Reference is given to U.S. patent application Ser. No. 09/442,816.

The invention is defined in the attached claims.

EXAMPLE

Methods

Protein Production and Purification

Purification of baculovirus produced recombinant TRAP was performed as described [16].

Crystallisation

The protein was crystallized by vapor diffusion with the hanging drop method. The crystals used in the structure determination were grown with a reservoir containing 16% PEG 8000, 0.1 M HEPES (buffer+precipitant+salt) pH 7.0 and 0.1 M $KH_2PO_4$. The drop consisted of 2 μl protein solution and 2 μl from the reservoir. The protein concentration was 5–8 mg/ml. Purple crystals appeared within two weeks at 18 C and reached a maximum size of 0.1×0.1×0.05 mm.

Using different conditions, different crystal forms were obtained but not all of these crystals were suitable for X-ray studies. Common to all successful crystallisation attempts was the presence of inorganic phosphate.

Data Collection

Most X-ray data was collected on an inhouse Raxis-4 imageplate detector mounted on a Rigaku RU300 rotating anode. A two-wavelength MAD dataset was also collected on beamline BL14 at ESRF, Grenoble. All data collection was performed under cryoconditions. Prior to freezing, the crystal was transferred for a few seconds to a cryosolution containing two parts reservoir solution and one part glycerol. The space group was $4_1$, with cell dimensions a=b=116.4 Å and c=63.3 Å. The best crystal diffracted to 2.7 Å resolution.

Three distinct heavy atom derivative crystals were produced, using $Hg(CN)_2/HgCl_2, K_2PtCl_4$ and $Na_2WO_4$. Heavy atom derivatives were prepared by adding small volumes (approximately 0.1 μl) of saturated heavy atom solutions to the crystal containing drop two hours prior to freezing. The mercury solution contained equal amounts of $Hg(CN)_2$ and $HgCl_2$.

The diffraction images were processed with DENZO and Scalepack [33], conserving the anomalous differences for all datasets, including the native. Native and derivative datasets were put to a common scale with the program Scaleit.

Structure Determination and Refinement

The strongest heavy atom site for the mercury derivative was found by difference Patterson map analysis. The other sites were located using difference Fourier syntheses. Mlphare [34] was used for heavy atom parameter refinement and phasing at this stage. Anomalous difference Fouriers were calculated to confirm heavy atom sites and identify the correct enantiomer. The phases were improved by solvent flattening in dm [35] and the corresponding electron density map to 3.5 Å resolution was used for most of the structure interpretation. Later on the programs Sharp [36] and Solomon [37] were used to produce an electron density map of superior quality to 2.7 Å. A partial model of kidney bean acid phosphatase was positioned into the density to facilitate model building. The two highest peaks in the anomalous difference Fourier of the native data corresponded well with the positions of the two metal binding sites in the positioned model of the kidney bean enzyme. A model of hTRAP was built with O [38] with intermittent rounds of refinement in CNS [39]. The progress of model improvement was monitored with Procheck [40]. The model consists of all residues for human TRAP, except a missing loop-region (residues 146–160) and the last four residues. The R-factor is 23% and the free R is 31% for reflections in the interval 50–2.7 Å.

82% of the residues fall in the most favorable regions of the Ramachandran plot as defined by Procheck. Data collection and refinement statistics are summarized in Table 1. The crystal structure giving the atomic structural coordinates is given in Table 2.

TABLE 1

Crystallographic data
Data collection

| Data set | resolution (Å) | λ (Å) | Completeness (%) (redundancy) | Rsym[a] | Riso[b] | Nr of sites | Phasing Power[c] |
|---|---|---|---|---|---|---|---|
| native | 2.7 | 1.542 | 89(3.9) | 0.107 | — | — | — |
| K$_2$PtCl$_4$ | 3.0 | 1.542 | 69(2.2) | 0.065 | 0.433 | 6 | 1.4 |
| Na$_2$WO$_4$ | 6.0 | 1.542 | 93(2.2) | 0.101 | 0.288 | 3 | 1.5 |
| mercury-1 | 3.0 | 1.542 | 88(3.7) | 0.076 | 0.363 | 4 | 2.1 |
| mercury-2 | 4.0 | 1.008 | 72(2.6) | 0.059 | 0.290 | 4 | 3.2 |
| mercury-3 | 4.0 | 0.918 | 68(2.7) | 0.080 | 0.279 | 4 | 2.8 |

Refinement
R-factor: 0.23; Free R: 0.31
[d]Ramachandran angle distribution (%): most favourable: 78.9, allowed: 18.6, generously allowed: 1.2, disallowed: 1.2
[a]$R_{sym} = \Sigma_h \Sigma_i |I(h) - <I(h)_i>|/\Sigma_h \Sigma_i I(h)_i$, where $<I(h)>$ is the average intensity of reflection h, $\Sigma_h$ is the sum over all reflections. and $\Sigma_i$ is the sum of all measurements of reflection h.
[b]$R_{iso} = \Sigma_h |F_{PH} - F_P|/\Sigma_h F_P$, where $F_{PH}$ and $F_P$ are the derivative and native structure factor amplitudes.
[c]Phasing power = $F_h$/lack of closure. Acentric reflections.
[d]Values and definitions from Procheck (49).
mercury-1,2,3: mixture of saturated solutions of Hg(CN)$_2$ and HgCl$_2$.

The Structure

The structure of TRAP can be described as a double beta sheet sandwhich surrounded on both sides by alpha helices and has the overall fold observed for the C-terminal domain of KBPAP. See FIG. 2 which shows a view of TRAP.

The active site with the two iron ions and the phosphate are shown at the top. The beginning and end of the repression loop (RL) are also marked.

The beta sheets have seven strands each and are mostly parallel and the di-iron active site is found at the C-terminal side of the sheets. See FIG. 3 which shows a secondary structure diagrams of the catalytic domains of TRAP.

After cleavage of the 21 amino acid N-terminal signal peptide, the sequential structure begins with five residues leading up to the first strand (β1) in the middle of sheet 1. This strand constitutes the first element in the conserved β-α-β-α-β motif. Asp 14 on β1 coordinate the Fe3+ ion and Asp 52 on β2 coordinate both the Fe2+ and Fe3+ ions. A tyrosine side chain, Tyr 55, also coordinates the Fe3+ ion and is responsible for the characteristic colour of this enzyme, due to a charge relay mechanism between the Fe3+ ion and the tyrosine side chain oxygen atom[18]. The delta oxygen of Asn 91 on β3 coordinates the Fe2+ ion. The sequence then adopts a helix-turn-helix structure followed by a final strand on this side of the sheet, before crossing over to sheet 2. The strand β4 does not have a corresponding element in KBPAP. Sheet 2 begins with two strands, β5 and β6, connected by a short turn. β6 is followed immediately by a short helix, α5. The region between Ser 145 and Val 161 is not visible in the electron density map. The density resumes at Val 161 and leads to α6 and β7. At the C-terminal edge of β7 His 186 is coordinating the Fe2+ ion. The following loop contains two residues, Glu 194 and His 195, that is located close to the active site. The corresponding pair in KBPAP contains two histidine residues. The structure continues with two helices, α7 and α8, interrupted by a proline residue and followed by β8. A short loop between β9 and β10 contains the last metal interaction site, where Nε of His 221 and Nδ of His 223 coordinates the Fe2+ and Fe3+ ions respectively. Sheet 2 continues with three antiparallel strands, β9–β11, before crossing over back to sheet 1. Three sequential and antiparallel strands constitutes the C-terminal part of the structure. The last four residues, Arg 303 -Pro 306 cannot be observed.

There is one disulfide bridge visible in the structure, between Cys142 on α5 and Cys 200 on α7. The two cysteines are located on different sides of the cleavage site and agrees with SDS-polyacrylamide gel electrophoresis studies with and without reducing agent, which suggested that the two substructures were connected by a disulfide[6].

There are two N-glycosylation motifs in the TRAP sequence. At the extension of the Asn 97 side chain extra density can be seen for one carbohydrate moiety, which has been included in the model. For Asn 128 no such density can be seen. The exposed nature and high B-factors of that side chain suggests that high mobility may be the cause for not observing glycosylation at this site. See FIG. 4 showing a view of a-carbons in TRAP. The active site and an N-glycosylation site at Asn 97 are displayed.

The Active Site

The side chains coordinating the iron ions in TRAP all have their equivalent in KBPAP as has been predicted[32]. See FIG. 5, a view of the active site of TRAP.

When all atoms in these residues, two aspartic acids, one asparagine, three histidines and a tyrosine, are aligned, the r.m.s distance is 0.7 Å. To achieve such similiarty in structure for the active site, the two proteins also share a conserved overall structure. A large density is visible near the two metals that agrees with the size of a phosphate ion. The resolution of the data does not inform us of the orientation of this molecule. Likewise, no solvent molecules in the active site can be modelled accurately based on the present data.

The protein surface in and around the active site can be used for structure based drug design. This surface is created by atoms from the two metal ions and from the following amino acid residues: Asp14, Asp52, Tyr55, Phe56, Asn91, His92, His186, Tyr187, Glu194, His195His221, His223, Phe244, Asp246. These amino acids are conserved between the rat enzyme, for which we have determined the structure, and the human enzyme. Their structure in the active site is therefore relevant for the design of modulators or inhibitors of the human TRAP.

The missing density for residues between Ser145 and Val161 raises the question of proteolytic activation. SDS-polyacrylamide gel electrophoresis indicated that crystallized TRAP had been cleaved into two fragments. FIG. 6 shows a SDS-PAGE gel showing the contents of the crystal containing drops. The first three lanes after marker were run under reducing conditions and the last three in non-reducing conditions. The gel shows that the protein has been cleaved between the residues forming the disulfide and where the sizes of the cleavage products corresponds to a cleavage of the protein in the repressions loop.

These fragments corresponded well in size to a cleavage of the protein in this region. We have in U.S. patent application Ser. No. 09/442,816 shown that rat TRAP can be cleaved in this part of the sequence with a resulting increase in activity (41). We cannot at this stage determine whether there is a question of a single nicking of the enzyme or if a part of the sequence has been excised. A single cleavage site would give rise to two loose ends that could be too mobile to be detected in the electron density maps. We have labeled the region between α5 and α6 the repression loop, since its cleavage or removal increases the activity of the enzyme up to ten fold. Ser145 is in close proximity to the active site and it is plausible that the uncleaved loop partly covers it and thereby interferes with activity. Interestingly, this loop domain is missing in KBPAP.

Catalytic Mechanism

The similarity of TRAP with the catalytic domain of KBPAP suggests a similar reaction mechanism for the two enzymes. Klabunde and coworkers have suggested a mechanism for hydrolysis of phosphate substrates by KBPAP, based on the crystal structures of this enzyme in unliganded form as well as in complex with the reaction product phosphate and with the inhibitor tungstate [31]. They conclude that the phosphate substrate interacts with the $Zn^{2+}$ ion followed by a nucleophilic attack on the phosphorous by an hydroxide ion coordinated by the $Fe^{3+}$ ion. The negatively charged transition state is believed to be stabilized by the $Zn^{2+}$ ion and by the imidazoles of three histidine residues His202, His295 and His296, where the latter is also suggested as a potential proton donor to the leaving alcohol group. These histidines in KBPAP have their structural counterparts in His92, Glu194 and His195 in TRAP. The side chain of Glu194 points down into the protein and is not in close contact with the phosphate group and probably has less of an effect on catalysis than His295 has in KBPAP. His92 and His195 on the other hand superposes closely on their KBPAP counterparts. The large difference between KBPAP and TRAP in the active site is the nature of the $M^{2+}$ ion, where KBPAP has a zink ion and TRAP an iron ion. Since the charge can alter between +2 and +3 for iron ions, TRAP is more sensitive than KBPAP to redox agents [21, 25, 28].

References

1. Griffith, J. P et al. Cell 82, 507–522 (1995).
2. Kissinger, C. R et al. Nature 378, 641–644 (1995).
3. Goldberg, J et al. Nature 376, 745–753 (1995).
4. Egloff, M. P et al.. J. Mol. Biol. 254, 942–959 (1995).
5. Ek-Rylander, B et al. J. Biol. Chem. 266, 24684–24689, (1991).
6. Hayman, A. R et al. J. Biol. Chem. 269, 1294–1300 (1994).
7. Cassady, A. I., et al. Gene 56, 109–116 (1993).
8. Koonin, E. V.. Protein Sci. 3, 356–358 (1994).
9. Vincent, J. B. et al.. FEBS Lett. 263, 265–268 (1990).
10. Lohse, D. L, et al. Structure 3, 987–990 (1995).
11. Rusnak, F., et al. J. Bioinorg. Chem. 1, 388–396 (1996).
12. Mertz, P., et al.. J. Biol. Chem. 272, 21296–21302 (1997).
13. Huang, H-B et al. Proc. Natl. Acad. Sci. USA 94, 3530–3535 (1997).
14. Zhang, J., et al.. Biochemistry 35, 6276–6282 (1996).
15. Andersson, K. K. et al. Adv. Inorg. Chem. 43, 359–408 (1995).
16. Ek-Rylander, et al.. Biochem. J. 321, 305–311 (1997).
17. Sträter, N., et al.. Science 268, 1489–1492 (1995).
18. Schlosnagle, D. C., et al. J. Biol. Chem. 249, 7574–7579 (1974).
19. Antanaitis, B. C. & Aisen, P.. Adv. Inorg. Biochem. 5, 111–136 (1983).
20. Averill, B. A.,et al. J. Am. Chem. Soc. 109, 3760–3767 (1987).
21. Doi, K et al. Struct. Bonding 70, 1–26 (1988).
22. Dietrich, M et al.. Eur. J. Biochem. 199, 105–113 (1991).
23. Vincent, J. B. et al.. FASEB. J. 4, 3009–3014 (1990).
24. Andersson, G., et al.. pp 55–80. (1992) CRC Press, Boca Raton.
25. Beck, J. L., et al.. J. Am. Chem. Soc. 110, 3317–3318 (1988).
26. Vincent, J. B et al.. Biochemistry 30, 3025–3034 (1991).
27. Wang, Z., et al. Biochemistry 31, 5263–5268 (1992).
28. Beck, J. L et al.. Biochim. Biophys. Acta 791, 357–363 (1984).
29. Wang, X., et al. Biochemistry 35, 13946–13954 (1996).
30. Battistuzzi, G., et al. Biochem. J. 323, 593–596 (1997).
31. Klabunde,T., et al. J. Mol. Biol. 259, 737–748 (1996).
32. Klabunde, T et al.. FEBS Letters 367, 56–60 (1995).
33. Otwinowski, Z et al. *Methods Enzymol.*, 276, 307–326 (1996).
34. Otwinowski, Z. *Proceedings of the CCP4 study weekend*. Daresbury Laboratory, Warrington, UK, 80–86 (1991).
35. Zhang, K. Y. J. et al.. Acta Cryst., A46, 377–381 (1990).
36. La Fortelle, E. de et al. *Methods EnzymoL.*, 276, 472–494 (1997).
37. Abrahams J. P. et al.. *Acta Cryst*. D52, 30–42 (1996).
38. Jones, T. A., et al.. Acta Cryst., A47, 110–119 (1991).
39. Brüinger, A. T., et al. *Acta Cryst* D54, 905–921 (1998).
40. Morris, A. L., et al. Struct. Funct. and Genet., 12, 345–364 (1992).
41. Ljusberg, J., Ek-Rylander, B., & Andersson, G. Tartrate-resistant purple acid phosphatase is synthesized as a latent proenzyme and activated by cysteine proteinases. Submitted

SEQUENCE LISTING

<160> NUMBER OF SEQ ID NOS: 1

<210> SEQ ID NO 1
<211> LENGTH: 306

```
<212> TYPE: PRT
<213> ORGANISM: rat

<400> SEQUENCE: 1

Thr Ala Pro Ala Ser Thr Leu Arg Phe Val Ala Val Gly Asp Trp Gly
 1               5                  10                  15

Gly Val Pro Asn Ala Pro Phe His Thr Ala Arg Glu Met Ala Asn Ala
                20                  25                  30

Lys Glu Ile Ala Arg Thr Val Gln Ile Met Gly Ala Asp Phe Ile Met
            35                  40                  45

Ser Leu Gly Asp Asn Phe Tyr Phe Thr Gly Val His Asp Ala Asn Asp
    50                  55                  60

Lys Arg Phe Gln Glu Thr Phe Glu Asp Val Phe Ser Asp Arg Ala Leu
65                  70                  75                  80

Arg Asn Ile Pro Trp Tyr Val Leu Ala Gly Asn His Asp His Leu Gly
                85                  90                  95

Asn Val Ser Ala Gln Ile Ala Tyr Ser Lys Ile Ser Lys Arg Trp Asn
            100                 105                 110

Phe Pro Ser Pro Tyr Tyr Arg Leu Arg Phe Lys Val Pro Arg Ser Asn
        115                 120                 125

Ile Thr Val Ala Ile Phe Met Leu Asp Thr Val Met Leu Cys Gly Asn
    130                 135                 140

Ser Asp Asp Phe Val Ser Gln Gln Pro Glu Met Pro Arg Asp Leu Gly
145                 150                 155                 160

Val Ala Arg Thr Gln Leu Ser Trp Leu Lys Lys Gln Leu Ala Ala Ala
                165                 170                 175

Lys Glu Asp Tyr Val Leu Val Ala Gly His Tyr Pro Ile Trp Ser Ile
            180                 185                 190

Ala Glu His Gly Pro Thr Arg Cys Leu Val Lys Asn Leu Arg Pro Leu
        195                 200                 205

Leu Ala Ala Tyr Gly Val Thr Ala Tyr Leu Cys Gly His Asp His Asn
    210                 215                 220

Leu Gln Tyr Leu Gln Asp Glu Asn Gly Val Gly Tyr Val Leu Ser Gly
225                 230                 235                 240

Ala Gly Asn Phe Met Asp Pro Ser Val Arg His Gln Arg Lys Val Pro
                245                 250                 255

Asn Gly Tyr Leu Arg Phe His Tyr Gly Ser Glu Asp Ser Leu Gly Gly
            260                 265                 270

Phe Thr Tyr Val Glu Ile Gly Ser Lys Glu Met Ser Ile Thr Tyr Val
        275                 280                 285

Glu Ala Ser Gly Lys Ser Leu Phe Lys Thr Ser Leu Pro Arg Arg Pro
    290                 295                 300

Arg Pro
305
```

Table 2

Column contents:

1: Atom number
2: Atom type
3: Residue type
4: Residue number
5: atomic coordinate, X (unit Ångström)
6: atomic coordinate, Y
7: atomic coordinate, Z
8: atomic occupancy
9: B-factor

| 1 | 2 | 3 | 4 | 5 | 6 | 7 | 8 | 9 |
|---|---|---|---|---|---|---|---|---|
| 1 | CB | THR | 1 | 120.606 | 13.630 | 3.450 | 1.00 | 30.00 |
| 2 | OG1 | THR | 1 | 121.896 | 13.958 | 2.918 | 1.00 | 30.00 |
| 3 | CG2 | THR | 1 | 120.323 | 14.545 | 4.633 | 1.00 | 30.00 |
| 4 | C | THR | 1 | 119.186 | 11.774 | 4.394 | 1.00 | 30.00 |
| 5 | O | THR | 1 | 118.175 | 12.219 | 3.846 | 1.00 | 30.00 |
| 6 | N | THR | 1 | 120.984 | 11.253 | 2.757 | 1.00 | 30.00 |
| 7 | CA | THR | 1 | 120.584 | 12.139 | 3.885 | 1.00 | 30.00 |
| 8 | N | ALA | 2 | 119.141 | 10.950 | 5.440 | 1.00 | 30.00 |
| 9 | CA | ALA | 2 | 117.891 | 10.508 | 6.061 | 1.00 | 30.00 |
| 10 | CB | ALA | 2 | 117.501 | 9.121 | 5.541 | 1.00 | 30.00 |
| 11 | C | ALA | 2 | 118.087 | 10.467 | 7.582 | 1.00 | 30.00 |
| 12 | O | ALA | 2 | 119.071 | 9.915 | 8.072 | 1.00 | 30.00 |
| 13 | N | PRO | 3 | 117.150 | 11.057 | 8.344 | 1.00 | 30.00 |
| 14 | CD | PRO | 3 | 116.001 | 11.837 | 7.847 | 1.00 | 30.00 |
| 15 | CA | PRO | 3 | 117.205 | 11.102 | 9.812 | 1.00 | 30.00 |
| 16 | CB | PRO | 3 | 115.933 | 11.872 | 10.179 | 1.00 | 30.00 |
| 17 | CG | PRO | 3 | 115.726 | 12.768 | 9.002 | 1.00 | 30.00 |
| 18 | C | PRO | 3 | 117.260 | 9.738 | 10.516 | 1.00 | 30.00 |
| 19 | O | PRO | 3 | 116.666 | 9.570 | 11.584 | 1.00 | 30.00 |
| 20 | N | ALA | 4 | 117.970 | 8.775 | 9.931 | 1.00 | 30.00 |
| 21 | CA | ALA | 4 | 118.078 | 7.433 | 10.512 | 1.00 | 30.00 |
| 22 | CB | ALA | 4 | 118.305 | 6.409 | 9.401 | 1.00 | 30.00 |
| 23 | C | ALA | 4 | 119.196 | 7.335 | 11.553 | 1.00 | 30.00 |
| 24 | O | ALA | 4 | 120.362 | 7.557 | 11.237 | 1.00 | 30.00 |
| 25 | N | SER | 5 | 118.843 | 6.984 | 12.787 | 1.00 | 30.00 |
| 26 | CA | SER | 5 | 119.834 | 6.880 | 13.859 | 1.00 | 30.00 |
| 27 | CB | SER | 5 | 119.142 | 6.930 | 15.220 | 1.00 | 30.00 |
| 28 | OG | SER | 5 | 120.081 | 6.760 | 16.269 | 1.00 | 30.00 |
| 29 | C | SER | 5 | 120.715 | 5.630 | 13.791 | 1.00 | 30.00 |
| 30 | O | SER | 5 | 120.932 | 4.953 | 14.797 | 1.00 | 30.00 |
| 31 | N | THR | 6 | 121.242 | 5.343 | 12.609 | 1.00 | 30.00 |
| 32 | CA | THR | 6 | 122.087 | 4.174 | 12.427 | 1.00 | 30.00 |
| 33 | CB | THR | 6 | 121.391 | 3.142 | 11.537 | 1.00 | 30.00 |
| 34 | OG1 | THR | 6 | 120.893 | 3.793 | 10.362 | 1.00 | 30.00 |
| 35 | CG2 | THR | 6 | 120.255 | 2.480 | 12.279 | 1.00 | 30.00 |

Table 2

Column contents:

1: Atom number
2: Atom type
3: Residue type
4: Residue number
5: atomic coordinate, X (unit Ångström)
6: atomic coordinate, Y
7: atomic coordinate, Z
8: atomic occupancy
9: B-factor

| 1 | 2 | 3 | 4 | 5 | 6 | 7 | 8 | 9 |
|---|---|---|---|---|---|---|---|---|
| 1 | CB | THR | 1 | 120.606 | 13.630 | 3.450 | 1.00 | 30.00 |
| 2 | OG1 | THR | 1 | 121.896 | 13.958 | 2.918 | 1.00 | 30.00 |
| 3 | CG2 | THR | 1 | 120.323 | 14.545 | 4.633 | 1.00 | 30.00 |
| 4 | C | THR | 1 | 119.186 | 11.774 | 4.394 | 1.00 | 30.00 |
| 5 | O | THR | 1 | 118.175 | 12.219 | 3.846 | 1.00 | 30.00 |
| 6 | N | THR | 1 | 120.984 | 11.253 | 2.757 | 1.00 | 30.00 |
| 7 | CA | THR | 1 | 120.584 | 12.139 | 3.885 | 1.00 | 30.00 |
| 8 | N | ALA | 2 | 119.141 | 10.950 | 5.440 | 1.00 | 30.00 |
| 9 | CA | ALA | 2 | 117.891 | 10.508 | 6.061 | 1.00 | 30.00 |
| 10 | CB | ALA | 2 | 117.501 | 9.121 | 5.541 | 1.00 | 30.00 |
| 11 | C | ALA | 2 | 118.087 | 10.467 | 7.582 | 1.00 | 30.00 |
| 12 | O | ALA | 2 | 119.071 | 9.915 | 8.072 | 1.00 | 30.00 |
| 13 | N | PRO | 3 | 117.150 | 11.057 | 8.344 | 1.00 | 30.00 |
| 14 | CD | PRO | 3 | 116.001 | 11.837 | 7.847 | 1.00 | 30.00 |
| 15 | CA | PRO | 3 | 117.205 | 11.102 | 9.812 | 1.00 | 30.00 |
| 16 | CB | PRO | 3 | 115.933 | 11.872 | 10.179 | 1.00 | 30.00 |
| 17 | CG | PRO | 3 | 115.726 | 12.768 | 9.002 | 1.00 | 30.00 |
| 18 | C | PRO | 3 | 117.260 | 9.738 | 10.516 | 1.00 | 30.00 |
| 19 | O | PRO | 3 | 116.666 | 9.570 | 11.584 | 1.00 | 30.00 |
| 20 | N | ALA | 4 | 117.970 | 8.775 | 9.931 | 1.00 | 30.00 |
| 21 | CA | ALA | 4 | 118.078 | 7.433 | 10.512 | 1.00 | 30.00 |
| 22 | CB | ALA | 4 | 118.305 | 6.409 | 9.401 | 1.00 | 30.00 |
| 23 | C | ALA | 4 | 119.196 | 7.335 | 11.553 | 1.00 | 30.00 |
| 24 | O | ALA | 4 | 120.362 | 7.557 | 11.237 | 1.00 | 30.00 |
| 25 | N | SER | 5 | 118.843 | 6.984 | 12.787 | 1.00 | 30.00 |
| 26 | CA | SER | 5 | 119.834 | 6.880 | 13.859 | 1.00 | 30.00 |
| 27 | CB | SER | 5 | 119.142 | 6.930 | 15.220 | 1.00 | 30.00 |
| 28 | OG | SER | 5 | 120.081 | 6.760 | 16.269 | 1.00 | 30.00 |
| 29 | C | SER | 5 | 120.715 | 5.630 | 13.791 | 1.00 | 30.00 |
| 30 | O | SER | 5 | 120.932 | 4.953 | 14.797 | 1.00 | 30.00 |
| 31 | N | THR | 6 | 121.242 | 5.343 | 12.609 | 1.00 | 30.00 |
| 32 | CA | THR | 6 | 122.087 | 4.174 | 12.427 | 1.00 | 30.00 |
| 33 | CB | THR | 6 | 121.391 | 3.142 | 11.537 | 1.00 | 30.00 |
| 34 | OG1 | THR | 6 | 120.893 | 3.793 | 10.362 | 1.00 | 30.00 |
| 35 | CG2 | THR | 6 | 120.255 | 2.480 | 12.279 | 1.00 | 30.00 |

| 36 | C | THR | 6 | 123.436 | 4.486 | 11.790 | 1.00 | 30.00 |
|---|---|---|---|---|---|---|---|---|
| 37 | O | THR | 6 | 123.582 | 5.485 | 11.082 | 1.00 | 30.00 |
| 38 | N | LEU | 7 | 124.418 | 3.624 | 12.053 | 1.00 | 30.00 |
| 39 | CA | LEU | 7 | 125.746 | 3.769 | 11.467 | 1.00 | 30.00 |
| 40 | CB | LEU | 7 | 126.779 | 2.926 | 12.225 | 1.00 | 30.00 |
| 41 | CG | LEU | 7 | 128.207 | 2.995 | 11.671 | 1.00 | 30.00 |
| 42 | CD1 | LEU | 7 | 128.810 | 4.361 | 11.954 | 1.00 | 30.00 |
| 43 | CD2 | LEU | 7 | 129.050 | 1.930 | 12.308 | 1.00 | 30.00 |
| 44 | C | LEU | 7 | 125.578 | 3.218 | 10.060 | 1.00 | 30.00 |
| 45 | O | LEU | 7 | 125.203 | 2.061 | 9.888 | 1.00 | 30.00 |
| 46 | N | ARG | 8 | 125.830 | 4.040 | 9.052 | 1.00 | 30.00 |
| 47 | CA | ARG | 8 | 125.664 | 3.587 | 7.680 | 1.00 | 30.00 |
| 48 | CB | ARG | 8 | 124.577 | 4.408 | 6.983 | 1.00 | 30.00 |
| 49 | CG | ARG | 8 | 123.174 | 4.239 | 7.551 | 1.00 | 30.00 |
| 50 | CD | ARG | 8 | 122.378 | 5.529 | 7.390 | 1.00 | 30.00 |
| 51 | NE | ARG | 8 | 122.937 | 6.621 | 8.193 | 1.00 | 30.00 |
| 52 | CZ | ARG | 8 | 123.262 | 7.820 | 7.719 | 1.00 | 30.00 |
| 53 | NH1 | ARG | 8 | 123.090 | 8.105 | 6.433 | 1.00 | 30.00 |
| 54 | NH2 | ARG | 8 | 123.781 | 8.735 | 8.528 | 1.00 | 30.00 |
| 55 | C | ARG | 8 | 126.965 | 3.716 | 6.913 | 1.00 | 30.00 |
| 56 | O | ARG | 8 | 127.823 | 4.529 | 7.264 | 1.00 | 30.00 |
| 57 | N | PHE | 9 | 127.122 | 2.905 | 5.872 | 1.00 | 30.00 |
| 58 | CA | PHE | 9 | 128.326 | 2.965 | 5.050 | 1.00 | 30.00 |
| 59 | CB | PHE | 9 | 129.596 | 2.632 | 5.872 | 1.00 | 30.00 |
| 60 | CG | PHE | 9 | 129.721 | 1.179 | 6.278 | 1.00 | 30.00 |
| 61 | CD1 | PHE | 9 | 130.156 | 0.214 | 5.368 | 1.00 | 30.00 |
| 62 | CD2 | PHE | 9 | 129.420 | 0.780 | 7.585 | 1.00 | 30.00 |
| 63 | CE1 | PHE | 9 | 130.287 | -1.128 | 5.753 | 1.00 | 30.00 |
| 64 | CE2 | PHE | 9 | 129.547 | -0.553 | 7.982 | 1.00 | 30.00 |
| 65 | CZ | PHE | 9 | 129.981 | -1.509 | 7.070 | 1.00 | 30.00 |
| 66 | C | PHE | 9 | 128.215 | 2.016 | 3.890 | 1.00 | 30.00 |
| 67 | O | PHE | 9 | 127.553 | 0.983 | 3.996 | 1.00 | 30.00 |
| 68 | N | VAL | 10 | 128.844 | 2.387 | 2.775 | 1.00 | 30.00 |
| 69 | CA | VAL | 10 | 128.874 | 1.534 | 1.594 | 1.00 | 30.00 |
| 70 | CB | VAL | 10 | 128.829 | 2.346 | 0.291 | 1.00 | 30.00 |
| 71 | CG1 | VAL | 10 | 129.384 | 1.518 | -0.854 | 1.00 | 30.00 |
| 72 | CG2 | VAL | 10 | 127.393 | 2.752 | -0.015 | 1.00 | 30.00 |
| 73 | C | VAL | 10 | 130.192 | 0.777 | 1.663 | 1.00 | 30.00 |
| 74 | O | VAL | 10 | 131.169 | 1.274 | 2.224 | 1.00 | 30.00 |
| 75 | N | ALA | 11 | 130.201 | -0.432 | 1.116 | 1.00 | 30.00 |
| 76 | CA | ALA | 11 | 131.395 | -1.269 | 1.096 | 1.00 | 30.00 |
| 77 | CB | ALA | 11 | 131.246 | -2.414 | 2.093 | 1.00 | 30.00 |
| 78 | C | ALA | 11 | 131.612 | -1.811 | -0.323 | 1.00 | 30.00 |
| 79 | O | ALA | 11 | 130.892 | -2.706 | -0.777 | 1.00 | 30.00 |
| 80 | N | VAL | 12 | 132.578 | -1.227 | -1.029 | 1.00 | 30.00 |
| 81 | CA | VAL | 12 | 132.919 | -1.638 | -2.394 | 1.00 | 30.00 |
| 82 | CB | VAL | 12 | 133.080 | -0.427 | -3.386 | 1.00 | 30.00 |
| 83 | CG1 | VAL | 12 | 131.886 | -0.315 | -4.316 | 1.00 | 30.00 |
| 84 | CG2 | VAL | 12 | 133.288 | 0.866 | -2.610 | 1.00 | 30.00 |
| 85 | C | VAL | 12 | 134.269 | -2.341 | -2.357 | 1.00 | 30.00 |
| 86 | O | VAL | 12 | 135.033 | -2.229 | -1.397 | 1.00 | 30.00 |
| 87 | N | GLY | 13 | 134.560 | -3.062 | -3.423 | 1.00 | 30.00 |

| 88 | CA | GLY | 13 | 135.825 | -3.742 | -3.500 | 1.00 | 30.00 |
| 89 | C | GLY | 13 | 136.144 | -3.918 | -4.963 | 1.00 | 30.00 |
| 90 | O | GLY | 13 | 135.244 | -3.903 | -5.802 | 1.00 | 30.00 |
| 91 | N | ASP | 14 | 137.426 | -4.013 | -5.273 | 1.00 | 30.00 |
| 92 | CA | ASP | 14 | 137.850 | -4.266 | -6.630 | 1.00 | 30.00 |
| 93 | CB | ASP | 14 | 137.354 | -5.659 | -7.016 | 1.00 | 30.00 |
| 94 | CG | ASP | 14 | 137.870 | -6.730 | -6.078 | 1.00 | 30.00 |
| 95 | OD2 | ASP | 14 | 137.298 | -6.842 | -4.968 | 1.00 | 30.00 |
| 96 | C | ASP | 14 | 137.467 | -3.275 | -7.718 | 1.00 | 30.00 |
| 97 | O | ASP | 14 | 137.030 | -3.692 | -8.790 | 1.00 | 30.00 |
| 98 | OD1 | ASP | 14 | 138.845 | -7.439 | -6.443 | 1.00 | 30.00 |
| 99 | N | TRP | 15 | 137.652 | -1.980 | -7.465 | 1.00 | 30.00 |
| 100 | CA | TRP | 15 | 137.348 | -0.937 | -8.458 | 1.00 | 30.00 |
| 101 | CB | TRP | 15 | 136.492 | 0.156 | -7.815 | 1.00 | 30.00 |
| 102 | CG | TRP | 15 | 137.047 | 0.586 | -6.511 | 1.00 | 30.00 |
| 103 | CD2 | TRP | 15 | 138.005 | 1.624 | -6.304 | 1.00 | 30.00 |
| 104 | CE2 | TRP | 15 | 138.408 | 1.566 | -4.948 | 1.00 | 30.00 |
| 105 | CE3 | TRP | 15 | 138.574 | 2.596 | -7.137 | 1.00 | 30.00 |
| 106 | CD1 | TRP | 15 | 136.890 | -0.038 | -5.296 | 1.00 | 30.00 |
| 107 | NE1 | TRP | 15 | 137.711 | 0.545 | -4.355 | 1.00 | 30.00 |
| 108 | CZ2 | TRP | 15 | 139.358 | 2.435 | -4.410 | 1.00 | 30.00 |
| 109 | CZ3 | TRP | 15 | 139.527 | 3.465 | -6.600 | 1.00 | 30.00 |
| 110 | CH2 | TRP | 15 | 139.905 | 3.379 | -5.249 | 1.00 | 30.00 |
| 111 | C | TRP | 15 | 138.647 | -0.328 | -9.027 | 1.00 | 30.00 |
| 112 | O | TRP | 15 | 139.733 | -0.541 | -8.482 | 1.00 | 30.00 |
| 113 | N | GLY | 16 | 138.546 | 0.402 | -10.135 | 1.00 | 30.00 |
| 114 | CA | GLY | 16 | 139.733 | 1.029 | -10.714 | 1.00 | 30.00 |
| 115 | C | GLY | 16 | 140.336 | 0.329 | -11.920 | 1.00 | 30.00 |
| 116 | O | GLY | 16 | 141.070 | -0.643 | -11.765 | 1.00 | 30.00 |
| 117 | N | GLY | 17 | 140.058 | 0.840 | -13.119 | 1.00 | 30.00 |
| 118 | CA | GLY | 17 | 140.559 | 0.218 | -14.338 | 1.00 | 30.00 |
| 119 | C | GLY | 17 | 141.923 | 0.575 | -14.915 | 1.00 | 30.00 |
| 120 | O | GLY | 17 | 142.136 | 0.393 | -16.114 | 1.00 | 30.00 |
| 121 | N | VAL | 18 | 142.842 | 1.100 | -14.106 | 1.00 | 30.00 |
| 122 | CA | VAL | 18 | 144.185 | 1.400 | -14.613 | 1.00 | 30.00 |
| 123 | CB | VAL | 18 | 144.995 | 2.387 | -13.709 | 1.00 | 30.00 |
| 124 | CG1 | VAL | 18 | 144.574 | 3.801 | -13.984 | 1.00 | 30.00 |
| 125 | CG2 | VAL | 18 | 144.842 | 2.030 | -12.235 | 1.00 | 30.00 |
| 126 | C | VAL | 18 | 144.968 | 0.088 | -14.674 | 1.00 | 30.00 |
| 127 | O | VAL | 18 | 144.574 | -0.912 | -14.059 | 1.00 | 30.00 |
| 128 | N | PRO | 19 | 146.110 | 0.080 | -15.383 | 1.00 | 30.00 |
| 129 | CD | PRO | 19 | 147.072 | -1.032 | -15.327 | 1.00 | 30.00 |
| 130 | CA | PRO | 19 | 146.691 | 1.214 | -16.105 | 1.00 | 30.00 |
| 131 | CB | PRO | 19 | 148.074 | 0.697 | -16.499 | 1.00 | 30.00 |
| 132 | CG | PRO | 19 | 148.386 | -0.308 | -15.417 | 1.00 | 30.00 |
| 133 | C | PRO | 19 | 145.877 | 1.634 | -17.315 | 1.00 | 30.00 |
| 134 | O | PRO | 19 | 144.682 | 1.350 | -17.405 | 1.00 | 30.00 |
| 135 | N | ASN | 20 | 146.547 | 2.321 | -18.236 | 1.00 | 30.00 |
| 136 | CA | ASN | 20 | 145.943 | 2.799 | -19.474 | 1.00 | 30.00 |
| 137 | CB | ASN | 20 | 145.103 | 1.693 | -20.123 | 1.00 | 30.00 |
| 138 | CG | ASN | 20 | 145.899 | 0.428 | -20.374 | 1.00 | 30.00 |
| 139 | OD1 | ASN | 20 | 146.992 | 0.471 | -20.947 | 1.00 | 30.00 |

| | | | | | | | | |
|---|---|---|---|---|---|---|---|---|
| 140 | ND2 | ASN | 20 | 145.348 | -0.711 | -19.957 | 1.00 | 30.00 |
| 141 | C | ASN | 20 | 145.082 | 4.041 | -19.289 | 1.00 | 30.00 |
| 142 | O | ASN | 20 | 145.060 | 4.655 | -18.217 | 1.00 | 30.00 |
| 143 | N | ALA | 21 | 144.380 | 4.411 | -20.352 | 1.00 | 30.00 |
| 144 | CA | ALA | 21 | 143.510 | 5.572 | -20.327 | 1.00 | 30.00 |
| 145 | CB | ALA | 21 | 143.992 | 6.610 | -21.318 | 1.00 | 30.00 |
| 146 | C | ALA | 21 | 142.099 | 5.142 | -20.669 | 1.00 | 30.00 |
| 147 | O | ALA | 21 | 141.876 | 4.467 | -21.671 | 1.00 | 30.00 |
| 148 | N | PRO | 22 | 141.125 | 5.519 | -19.826 | 1.00 | 30.00 |
| 149 | CD | PRO | 22 | 139.695 | 5.510 | -20.177 | 1.00 | 30.00 |
| 150 | CA | PRO | 22 | 141.346 | 6.308 | -18.603 | 1.00 | 30.00 |
| 151 | CB | PRO | 22 | 139.989 | 6.970 | -18.361 | 1.00 | 30.00 |
| 152 | CG | PRO | 22 | 139.267 | 6.862 | -19.700 | 1.00 | 30.00 |
| 153 | C | PRO | 22 | 141.747 | 5.412 | -17.430 | 1.00 | 30.00 |
| 154 | O | PRO | 22 | 142.462 | 4.433 | -17.608 | 1.00 | 30.00 |
| 155 | N | PHE | 23 | 141.298 | 5.756 | -16.231 | 1.00 | 30.00 |
| 156 | CA | PHE | 23 | 141.593 | 4.942 | -15.057 | 1.00 | 30.00 |
| 157 | CB | PHE | 23 | 142.059 | 5.828 | -13.886 | 1.00 | 30.00 |
| 158 | CG | PHE | 23 | 141.719 | 5.288 | -12.500 | 1.00 | 30.00 |
| 159 | CD1 | PHE | 23 | 142.293 | 4.119 | -12.017 | 1.00 | 30.00 |
| 160 | CD2 | PHE | 23 | 140.807 | 5.952 | -11.692 | 1.00 | 30.00 |
| 161 | CE1 | PHE | 23 | 141.957 | 3.625 | -10.759 | 1.00 | 30.00 |
| 162 | CE2 | PHE | 23 | 140.466 | 5.470 | -10.438 | 1.00 | 30.00 |
| 163 | CZ | PHE | 23 | 141.040 | 4.302 | -9.971 | 1.00 | 30.00 |
| 164 | C | PHE | 23 | 140.310 | 4.207 | -14.699 | 1.00 | 30.00 |
| 165 | O | PHE | 23 | 140.246 | 3.479 | -13.709 | 1.00 | 30.00 |
| 166 | N | HIS | 24 | 139.291 | 4.374 | -15.535 | 1.00 | 30.00 |
| 167 | CA | HIS | 24 | 138.005 | 3.746 | -15.272 | 1.00 | 30.00 |
| 168 | CB | HIS | 24 | 136.968 | 4.817 | -14.953 | 1.00 | 30.00 |
| 169 | CG | HIS | 24 | 136.785 | 5.812 | -16.054 | 1.00 | 30.00 |
| 170 | CD2 | HIS | 24 | 136.039 | 5.763 | -17.185 | 1.00 | 30.00 |
| 171 | ND1 | HIS | 24 | 137.454 | 7.018 | -16.089 | 1.00 | 30.00 |
| 172 | CE1 | HIS | 24 | 137.125 | 7.668 | -17.192 | 1.00 | 30.00 |
| 173 | NE2 | HIS | 24 | 136.270 | 6.929 | -17.875 | 1.00 | 30.00 |
| 174 | C | HIS | 24 | 137.463 | 2.874 | -16.395 | 1.00 | 30.00 |
| 175 | O | HIS | 24 | 137.894 | 2.959 | -17.548 | 1.00 | 30.00 |
| 176 | N | THR | 25 | 136.489 | 2.049 | -16.011 | 1.00 | 30.00 |
| 177 | CA | THR | 25 | 135.784 | 1.130 | -16.896 | 1.00 | 30.00 |
| 178 | CB | THR | 25 | 135.888 | -0.305 | -16.377 | 1.00 | 30.00 |
| 179 | OG1 | THR | 25 | 135.449 | -0.340 | -15.012 | 1.00 | 30.00 |
| 180 | CG2 | THR | 25 | 137.325 | -0.805 | -16.467 | 1.00 | 30.00 |
| 181 | C | THR | 25 | 134.314 | 1.550 | -16.865 | 1.00 | 30.00 |
| 182 | O | THR | 25 | 133.878 | 2.230 | -15.932 | 1.00 | 30.00 |
| 183 | N | ALA | 26 | 133.553 | 1.151 | -17.878 | 1.00 | 30.00 |
| 184 | CA | ALA | 26 | 132.139 | 1.509 | -17.925 | 1.00 | 30.00 |
| 185 | CB | ALA | 26 | 131.419 | 0.672 | -18.982 | 1.00 | 30.00 |
| 186 | C | ALA | 26 | 131.524 | 1.256 | -16.558 | 1.00 | 30.00 |
| 187 | O | ALA | 26 | 130.741 | 2.064 | -16.041 | 1.00 | 30.00 |
| 188 | N | ARG | 27 | 131.920 | 0.123 | -15.981 | 1.00 | 30.00 |
| 189 | CA | ARG | 27 | 131.432 | -0.332 | -14.691 | 1.00 | 30.00 |
| 190 | CB | ARG | 27 | 131.823 | -1.796 | -14.474 | 1.00 | 30.00 |
| 191 | CG | ARG | 27 | 131.135 | -2.741 | -15.433 | 1.00 | 30.00 |

| 192 | CD  | ARG | 27 | 131.429 | -4.187 | -15.116 | 1.00 | 30.00 |
| 193 | NE  | ARG | 27 | 130.852 | -5.061 | -16.130 | 1.00 | 30.00 |
| 194 | CZ  | ARG | 27 | 131.320 | -6.267 | -16.430 | 1.00 | 30.00 |
| 195 | NH1 | ARG | 27 | 132.380 | -6.748 | -15.792 | 1.00 | 30.00 |
| 196 | NH2 | ARG | 27 | 130.743 | -6.986 | -17.384 | 1.00 | 30.00 |
| 197 | C   | ARG | 27 | 131.842 | 0.488  | -13.485 | 1.00 | 30.00 |
| 198 | O   | ARG | 27 | 130.998 | 0.782  | -12.642 | 1.00 | 30.00 |
| 199 | N   | GLU | 28 | 133.114 | 0.858  | -13.368 | 1.00 | 30.00 |
| 200 | CA  | GLU | 28 | 133.492 | 1.643  | -12.200 | 1.00 | 30.00 |
| 201 | CB  | GLU | 28 | 134.975 | 2.021  | -12.215 | 1.00 | 30.00 |
| 202 | CG  | GLU | 28 | 135.378 | 2.787  | -10.951 | 1.00 | 30.00 |
| 203 | CD  | GLU | 28 | 136.796 | 3.310  | -10.989 | 1.00 | 30.00 |
| 204 | OE1 | GLU | 28 | 137.266 | 3.670  | -12.090 | 1.00 | 30.00 |
| 205 | OE2 | GLU | 28 | 137.436 | 3.381  | -9.914  | 1.00 | 30.00 |
| 206 | C   | GLU | 28 | 132.623 | 2.901  | -12.204 | 1.00 | 30.00 |
| 207 | O   | GLU | 28 | 131.988 | 3.251  | -11.201 | 1.00 | 30.00 |
| 208 | N   | MET | 29 | 132.588 | 3.566  | -13.353 | 1.00 | 30.00 |
| 209 | CA  | MET | 29 | 131.776 | 4.761  | -13.524 | 1.00 | 30.00 |
| 210 | CB  | MET | 29 | 131.762 | 5.150  | -15.001 | 1.00 | 30.00 |
| 211 | CG  | MET | 29 | 133.109 | 5.603  | -15.507 | 1.00 | 30.00 |
| 212 | SD  | MET | 29 | 133.606 | 7.152  | -14.730 | 1.00 | 30.00 |
| 213 | CE  | MET | 29 | 133.077 | 8.328  | -16.001 | 1.00 | 30.00 |
| 214 | C   | MET | 29 | 130.341 | 4.515  | -13.027 | 1.00 | 30.00 |
| 215 | O   | MET | 29 | 129.809 | 5.296  | -12.226 | 1.00 | 30.00 |
| 216 | N   | ALA | 30 | 129.730 | 3.426  | -13.501 | 1.00 | 30.00 |
| 217 | CA  | ALA | 30 | 128.366 | 3.055  | -13.119 | 1.00 | 30.00 |
| 218 | CB  | ALA | 30 | 127.991 | 1.730  | -13.764 | 1.00 | 30.00 |
| 219 | C   | ALA | 30 | 128.199 | 2.961  | -11.608 | 1.00 | 30.00 |
| 220 | O   | ALA | 30 | 127.256 | 3.518  | -11.042 | 1.00 | 30.00 |
| 221 | N   | ASN | 31 | 129.112 | 2.250  | -10.955 | 1.00 | 30.00 |
| 222 | CA  | ASN | 31 | 129.056 | 2.104  | -9.506  | 1.00 | 30.00 |
| 223 | CB  | ASN | 31 | 130.094 | 1.100  | -9.021  | 1.00 | 30.00 |
| 224 | CG  | ASN | 31 | 129.642 | -0.313 | -9.215  | 1.00 | 30.00 |
| 225 | OD1 | ASN | 31 | 129.866 | -0.907 | -10.265 | 1.00 | 30.00 |
| 226 | ND2 | ASN | 31 | 128.973 | -0.862 | -8.203  | 1.00 | 30.00 |
| 227 | C   | ASN | 31 | 129.273 | 3.431  | -8.800  | 1.00 | 30.00 |
| 228 | O   | ASN | 31 | 128.663 | 3.691  | -7.764  | 1.00 | 30.00 |
| 229 | N   | ALA | 32 | 130.151 | 4.260  | -9.366  | 1.00 | 30.00 |
| 230 | CA  | ALA | 32 | 130.450 | 5.574  | -8.807  | 1.00 | 30.00 |
| 231 | CB  | ALA | 32 | 131.516 | 6.270  | -9.649  | 1.00 | 30.00 |
| 232 | C   | ALA | 32 | 129.165 | 6.397  | -8.787  | 1.00 | 30.00 |
| 233 | O   | ALA | 32 | 128.817 | 7.006  | -7.769  | 1.00 | 30.00 |
| 234 | N   | LYS | 33 | 128.457 | 6.396  | -9.917  | 1.00 | 30.00 |
| 235 | CA  | LYS | 33 | 127.201 | 7.129  | -10.043 | 1.00 | 30.00 |
| 236 | CB  | LYS | 33 | 126.670 | 7.052  | -11.479 | 1.00 | 30.00 |
| 237 | CG  | LYS | 33 | 125.255 | 7.599  | -11.635 | 1.00 | 30.00 |
| 238 | CD  | LYS | 33 | 124.882 | 7.822  | -13.085 | 1.00 | 30.00 |
| 239 | CE  | LYS | 33 | 125.720 | 8.938  | -13.690 | 1.00 | 30.00 |
| 240 | NZ  | LYS | 33 | 125.321 | 9.257  | -15.089 | 1.00 | 30.00 |
| 241 | C   | LYS | 33 | 126.134 | 6.620  | -9.077  | 1.00 | 30.00 |
| 242 | O   | LYS | 33 | 125.422 | 7.423  | -8.466  | 1.00 | 30.00 |
| 243 | N   | GLU | 34 | 126.028 | 5.296  | -8.933  | 1.00 | 30.00 |

| | | | | | | | |
|---|---|---|---|---|---|---|---|
| 244 | CA | GLU | 34 | 125.026 | 4.707 | -8.042 | 1.00 | 30.00 |
| 245 | CB | GLU | 34 | 124.806 | 3.225 | -8.362 | 1.00 | 30.00 |
| 246 | CG | GLU | 34 | 123.694 | 2.581 | -7.538 | 1.00 | 30.00 |
| 247 | CD | GLU | 34 | 122.423 | 3.423 | -7.531 | 1.00 | 30.00 |
| 248 | OE1 | GLU | 34 | 122.011 | 3.870 | -8.624 | 1.00 | 30.00 |
| 249 | OE2 | GLU | 34 | 121.839 | 3.638 | -6.441 | 1.00 | 30.00 |
| 250 | C | GLU | 34 | 125.384 | 4.855 | -6.572 | 1.00 | 30.00 |
| 251 | O | GLU | 34 | 124.507 | 5.104 | -5.743 | 1.00 | 30.00 |
| 252 | N | ILE | 35 | 126.662 | 4.687 | -6.243 | 1.00 | 30.00 |
| 253 | CA | ILE | 35 | 127.103 | 4.835 | -4.856 | 1.00 | 30.00 |
| 254 | CB | ILE | 35 | 128.597 | 4.470 | -4.673 | 1.00 | 30.00 |
| 255 | CG2 | ILE | 35 | 129.051 | 4.824 | -3.256 | 1.00 | 30.00 |
| 256 | CG1 | ILE | 35 | 128.805 | 2.977 | -4.935 | 1.00 | 30.00 |
| 257 | CD1 | ILE | 35 | 130.257 | 2.571 | -4.967 | 1.00 | 30.00 |
| 258 | C | ILE | 35 | 126.897 | 6.290 | -4.456 | 1.00 | 30.00 |
| 259 | O | ILE | 35 | 126.728 | 6.605 | -3.271 | 1.00 | 30.00 |
| 260 | N | ALA | 36 | 126.907 | 7.178 | -5.448 | 1.00 | 30.00 |
| 261 | CA | ALA | 36 | 126.691 | 8.593 | -5.174 | 1.00 | 30.00 |
| 262 | CB | ALA | 36 | 127.163 | 9.449 | -6.350 | 1.00 | 30.00 |
| 263 | C | ALA | 36 | 125.204 | 8.842 | -4.896 | 1.00 | 30.00 |
| 264 | O | ALA | 36 | 124.861 | 9.568 | -3.966 | 1.00 | 30.00 |
| 265 | N | ARG | 37 | 124.323 | 8.235 | -5.690 | 1.00 | 30.00 |
| 266 | CA | ARG | 37 | 122.899 | 8.438 | -5.483 | 1.00 | 30.00 |
| 267 | CB | ARG | 37 | 122.074 | 7.923 | -6.665 | 1.00 | 30.00 |
| 268 | CG | ARG | 37 | 120.561 | 8.052 | -6.418 | 1.00 | 30.00 |
| 269 | CD | ARG | 37 | 119.761 | 8.324 | -7.690 | 1.00 | 30.00 |
| 270 | NE | ARG | 37 | 119.886 | 7.241 | -8.659 | 1.00 | 30.00 |
| 271 | CZ | ARG | 37 | 119.471 | 6.000 | -8.439 | 1.00 | 30.00 |
| 272 | NH1 | ARG | 37 | 118.899 | 5.684 | -7.281 | 1.00 | 30.00 |
| 273 | NH2 | ARG | 37 | 119.638 | 5.076 | -9.375 | 1.00 | 30.00 |
| 274 | C | ARG | 37 | 122.430 | 7.758 | -4.218 | 1.00 | 30.00 |
| 275 | O | ARG | 37 | 121.706 | 8.352 | -3.415 | 1.00 | 30.00 |
| 276 | N | THR | 38 | 122.841 | 6.504 | -4.057 | 1.00 | 30.00 |
| 277 | CA | THR | 38 | 122.484 | 5.707 | -2.893 | 1.00 | 30.00 |
| 278 | CB | THR | 38 | 123.294 | 4.372 | -2.886 | 1.00 | 30.00 |
| 279 | OG1 | THR | 38 | 122.665 | 3.430 | -3.773 | 1.00 | 30.00 |
| 280 | CG2 | THR | 38 | 123.389 | 3.781 | -1.475 | 1.00 | 30.00 |
| 281 | C | THR | 38 | 122.734 | 6.489 | -1.601 | 1.00 | 30.00 |
| 282 | O | THR | 38 | 121.932 | 6.433 | -0.661 | 1.00 | 30.00 |
| 283 | N | VAL | 39 | 123.836 | 7.232 | -1.565 | 1.00 | 30.00 |
| 284 | CA | VAL | 39 | 124.181 | 8.016 | -0.386 | 1.00 | 30.00 |
| 285 | CB | VAL | 39 | 125.730 | 8.201 | -0.299 | 1.00 | 30.00 |
| 286 | CG1 | VAL | 39 | 126.241 | 8.909 | -1.536 | 1.00 | 30.00 |
| 287 | CG2 | VAL | 39 | 126.107 | 8.951 | 0.970 | 1.00 | 30.00 |
| 288 | C | VAL | 39 | 123.436 | 9.374 | -0.322 | 1.00 | 30.00 |
| 289 | O | VAL | 39 | 123.415 | 10.028 | 0.720 | 1.00 | 30.00 |
| 290 | N | GLN | 40 | 122.818 | 9.794 | -1.425 | 1.00 | 30.00 |
| 291 | CA | GLN | 40 | 122.047 | 11.043 | -1.421 | 1.00 | 30.00 |
| 292 | CB | GLN | 40 | 121.663 | 11.487 | -2.829 | 1.00 | 30.00 |
| 293 | CG | GLN | 40 | 122.802 | 11.684 | -3.787 | 1.00 | 30.00 |
| 294 | CD | GLN | 40 | 122.318 | 12.190 | -5.131 | 1.00 | 30.00 |
| 295 | OE1 | GLN | 40 | 123.081 | 12.262 | -6.097 | 1.00 | 30.00 |

| 296 | NE2 | GLN | 40 | 121.040 | 12.554 | -5.196 | 1.00 | 30.00 |
| 297 | C | GLN | 40 | 120.754 | 10.719 | -0.697 | 1.00 | 30.00 |
| 298 | O | GLN | 40 | 120.290 | 11.454 | 0.167 | 1.00 | 30.00 |
| 299 | N | ILE | 41 | 120.183 | 9.590 | -1.085 | 1.00 | 30.00 |
| 300 | CA | ILE | 41 | 118.938 | 9.099 | -0.535 | 1.00 | 30.00 |
| 301 | CB | ILE | 41 | 118.365 | 8.042 | -1.499 | 1.00 | 30.00 |
| 302 | CG2 | ILE | 41 | 116.981 | 7.609 | -1.066 | 1.00 | 30.00 |
| 303 | CG1 | ILE | 41 | 118.325 | 8.644 | -2.912 | 1.00 | 30.00 |
| 304 | CD1 | ILE | 41 | 117.797 | 7.725 | -3.974 | 1.00 | 30.00 |
| 305 | C | ILE | 41 | 119.083 | 8.545 | 0.893 | 1.00 | 30.00 |
| 306 | O | ILE | 41 | 118.540 | 9.115 | 1.845 | 1.00 | 30.00 |
| 307 | N | MET | 42 | 119.824 | 7.454 | 1.057 | 1.00 | 30.00 |
| 308 | CA | MET | 42 | 120.006 | 6.863 | 2.387 | 1.00 | 30.00 |
| 309 | CB | MET | 42 | 120.429 | 5.388 | 2.260 | 1.00 | 30.00 |
| 310 | CG | MET | 42 | 119.292 | 4.367 | 2.156 | 1.00 | 30.00 |
| 311 | SD | MET | 42 | 118.354 | 4.383 | 0.607 | 1.00 | 30.00 |
| 312 | CE | MET | 42 | 119.623 | 3.863 | -0.581 | 1.00 | 30.00 |
| 313 | C | MET | 42 | 121.021 | 7.600 | 3.282 | 1.00 | 30.00 |
| 314 | O | MET | 42 | 120.872 | 7.637 | 4.507 | 1.00 | 30.00 |
| 315 | N | GLY | 43 | 122.046 | 8.186 | 2.670 | 1.00 | 30.00 |
| 316 | CA | GLY | 43 | 123.070 | 8.864 | 3.443 | 1.00 | 30.00 |
| 317 | C | GLY | 43 | 124.097 | 7.832 | 3.872 | 1.00 | 30.00 |
| 318 | O | GLY | 43 | 123.749 | 6.677 | 4.100 | 1.00 | 30.00 |
| 319 | N | ALA | 44 | 125.362 | 8.220 | 3.977 | 1.00 | 30.00 |
| 320 | CA | ALA | 44 | 126.401 | 7.276 | 4.385 | 1.00 | 30.00 |
| 321 | CB | ALA | 44 | 127.068 | 6.665 | 3.141 | 1.00 | 30.00 |
| 322 | C | ALA | 44 | 127.451 | 7.954 | 5.265 | 1.00 | 30.00 |
| 323 | O | ALA | 44 | 127.889 | 9.066 | 4.966 | 1.00 | 30.00 |
| 324 | N | ASP | 45 | 127.849 | 7.292 | 6.351 | 1.00 | 30.00 |
| 325 | CA | ASP | 45 | 128.873 | 7.844 | 7.246 | 1.00 | 30.00 |
| 326 | CB | ASP | 45 | 128.903 | 7.087 | 8.571 | 1.00 | 30.00 |
| 327 | CG | ASP | 45 | 127.612 | 7.200 | 9.323 | 1.00 | 30.00 |
| 328 | OD1 | ASP | 45 | 127.397 | 6.416 | 10.265 | 1.00 | 30.00 |
| 329 | OD2 | ASP | 45 | 126.808 | 8.083 | 8.973 | 1.00 | 30.00 |
| 330 | C | ASP | 45 | 130.240 | 7.740 | 6.583 | 1.00 | 30.00 |
| 331 | O | ASP | 45 | 131.011 | 8.699 | 6.562 | 1.00 | 30.00 |
| 332 | N | PHE | 46 | 130.541 | 6.567 | 6.042 | 1.00 | 30.00 |
| 333 | CA | PHE | 46 | 131.820 | 6.381 | 5.380 | 1.00 | 30.00 |
| 334 | CB | PHE | 46 | 132.895 | 5.983 | 6.397 | 1.00 | 30.00 |
| 335 | CG | PHE | 46 | 132.656 | 4.660 | 7.054 | 1.00 | 30.00 |
| 336 | CD1 | PHE | 46 | 133.039 | 3.481 | 6.430 | 1.00 | 30.00 |
| 337 | CD2 | PHE | 46 | 132.068 | 4.591 | 8.312 | 1.00 | 30.00 |
| 338 | CE1 | PHE | 46 | 132.846 | 2.245 | 7.054 | 1.00 | 30.00 |
| 339 | CE2 | PHE | 46 | 131.866 | 3.358 | 8.947 | 1.00 | 30.00 |
| 340 | CZ | PHE | 46 | 132.258 | 2.186 | 8.317 | 1.00 | 30.00 |
| 341 | C | PHE | 46 | 131.739 | 5.350 | 4.275 | 1.00 | 30.00 |
| 342 | O | PHE | 46 | 130.675 | 4.814 | 3.973 | 1.00 | 30.00 |
| 343 | N | ILE | 47 | 132.879 | 5.084 | 3.663 | 1.00 | 30.00 |
| 344 | CA | ILE | 47 | 132.945 | 4.113 | 2.591 | 1.00 | 30.00 |
| 345 | CB | ILE | 47 | 132.968 | 4.826 | 1.221 | 1.00 | 30.00 |
| 346 | CG2 | ILE | 47 | 133.182 | 3.819 | 0.098 | 1.00 | 30.00 |
| 347 | CG1 | ILE | 47 | 131.660 | 5.594 | 1.025 | 1.00 | 30.00 |

| 348 | CD1 | ILE | 47 | 131.601 | 6.372 | -0.273 | 1.00 | 30.00 |
| 349 | C | ILE | 47 | 134.220 | 3.307 | 2.775 | 1.00 | 30.00 |
| 350 | O | ILE | 47 | 135.273 | 3.886 | 3.015 | 1.00 | 30.00 |
| 351 | N | MET | 48 | 134.134 | 1.978 | 2.717 | 1.00 | 30.00 |
| 352 | CA | MET | 48 | 135.350 | 1.182 | 2.838 | 1.00 | 30.00 |
| 353 | CB | MET | 48 | 135.306 | 0.176 | 4.002 | 1.00 | 30.00 |
| 354 | CG | MET | 48 | 134.511 | -1.084 | 3.761 | 1.00 | 30.00 |
| 355 | SD | MET | 48 | 134.848 | -2.367 | 5.017 | 1.00 | 30.00 |
| 356 | CE | MET | 48 | 134.008 | -1.691 | 6.535 | 1.00 | 30.00 |
| 357 | C | MET | 48 | 135.595 | 0.451 | 1.541 | 1.00 | 30.00 |
| 358 | O | MET | 48 | 134.696 | -0.182 | 0.980 | 1.00 | 30.00 |
| 359 | N | SER | 49 | 136.816 | 0.604 | 1.048 | 1.00 | 30.00 |
| 360 | CA | SER | 49 | 137.270 | -0.040 | -0.168 | 1.00 | 30.00 |
| 361 | CB | SER | 49 | 138.421 | 0.762 | -0.773 | 1.00 | 30.00 |
| 362 | OG | SER | 49 | 138.718 | 0.342 | -2.087 | 1.00 | 30.00 |
| 363 | C | SER | 49 | 137.769 | -1.403 | 0.303 | 1.00 | 30.00 |
| 364 | O | SER | 49 | 138.572 | -1.493 | 1.229 | 1.00 | 30.00 |
| 365 | N | LEU | 50 | 137.283 | -2.466 | -0.317 | 1.00 | 30.00 |
| 366 | CA | LEU | 50 | 137.694 | -3.793 | 0.093 | 1.00 | 30.00 |
| 367 | CB | LEU | 50 | 136.505 | -4.743 | -0.012 | 1.00 | 30.00 |
| 368 | CG | LEU | 50 | 135.395 | -4.431 | 1.003 | 1.00 | 30.00 |
| 369 | CD1 | LEU | 50 | 134.104 | -5.139 | 0.610 | 1.00 | 30.00 |
| 370 | CD2 | LEU | 50 | 135.856 | -4.844 | 2.399 | 1.00 | 30.00 |
| 371 | C | LEU | 50 | 138.901 | -4.355 | -0.650 | 1.00 | 30.00 |
| 372 | O | LEU | 50 | 139.201 | -5.536 | -0.525 | 1.00 | 30.00 |
| 373 | N | GLY | 51 | 139.598 | -3.529 | -1.428 | 1.00 | 30.00 |
| 374 | CA | GLY | 51 | 140.778 | -4.041 | -2.107 | 1.00 | 30.00 |
| 375 | C | GLY | 51 | 140.865 | -3.903 | -3.609 | 1.00 | 30.00 |
| 376 | O | GLY | 51 | 139.854 | -3.725 | -4.277 | 1.00 | 30.00 |
| 377 | N | ASP | 52 | 142.080 | -4.031 | -4.140 | 1.00 | 30.00 |
| 378 | CA | ASP | 52 | 142.312 | -3.874 | -5.567 | 1.00 | 30.00 |
| 379 | CB | ASP | 52 | 141.503 | -4.905 | -6.368 | 1.00 | 30.00 |
| 380 | CG | ASP | 52 | 142.065 | -6.328 | -6.254 | 1.00 | 30.00 |
| 381 | OD1 | ASP | 52 | 143.282 | -6.490 | -6.002 | 1.00 | 30.00 |
| 382 | C | ASP | 52 | 141.892 | -2.444 | -5.930 | 1.00 | 30.00 |
| 383 | O | ASP | 52 | 141.074 | -2.224 | -6.821 | 1.00 | 30.00 |
| 384 | OD2 | ASP | 52 | 141.283 | -7.295 | -6.440 | 1.00 | 30.00 |
| 385 | N | ASN | 53 | 142.476 | -1.482 | -5.214 | 1.00 | 30.00 |
| 386 | CA | ASN | 53 | 142.209 | -0.052 | -5.391 | 1.00 | 30.00 |
| 387 | CB | ASN | 53 | 142.853 | 0.719 | -4.232 | 1.00 | 30.00 |
| 388 | CG | ASN | 53 | 142.327 | 0.264 | -2.877 | 1.00 | 30.00 |
| 389 | OD1 | ASN | 53 | 141.131 | 0.333 | -2.617 | 1.00 | 30.00 |
| 390 | ND2 | ASN | 53 | 143.217 | -0.205 | -2.014 | 1.00 | 30.00 |
| 391 | C | ASN | 53 | 142.608 | 0.575 | -6.752 | 1.00 | 30.00 |
| 392 | O | ASN | 53 | 141.945 | 1.501 | -7.240 | 1.00 | 30.00 |
| 393 | N | PHE | 54 | 143.691 | 0.088 | -7.354 | 1.00 | 30.00 |
| 394 | CA | PHE | 54 | 144.143 | 0.569 | -8.670 | 1.00 | 30.00 |
| 395 | CB | PHE | 54 | 145.278 | 1.572 | -8.497 | 1.00 | 30.00 |
| 396 | CG | PHE | 54 | 144.929 | 2.685 | -7.559 | 1.00 | 30.00 |
| 397 | CD1 | PHE | 54 | 145.239 | 2.593 | -6.201 | 1.00 | 30.00 |
| 398 | CD2 | PHE | 54 | 144.201 | 3.781 | -8.008 | 1.00 | 30.00 |
| 399 | CE1 | PHE | 54 | 144.820 | 3.577 | -5.305 | 1.00 | 30.00 |

| 400 | CE2 | PHE | 54 | 143.778 | 4.769 | -7.124 | 1.00 | 30.00 |
| 401 | CZ | PHE | 54 | 144.087 | 4.666 | -5.769 | 1.00 | 30.00 |
| 402 | C | PHE | 54 | 144.582 | -0.736 | -9.298 | 1.00 | 30.00 |
| 403 | O | PHE | 54 | 145.712 | -1.179 | -9.139 | 1.00 | 30.00 |
| 404 | N | TYR | 55 | 143.656 | -1.317 | -10.048 | 1.00 | 30.00 |
| 405 | CA | TYR | 55 | 143.779 | -2.665 | -10.581 | 1.00 | 30.00 |
| 406 | CB | TYR | 55 | 142.641 | -2.941 | -11.542 | 1.00 | 30.00 |
| 407 | CG | TYR | 55 | 141.719 | -3.887 | -10.869 | 1.00 | 30.00 |
| 408 | CD1 | TYR | 55 | 140.739 | -3.409 | -10.015 | 1.00 | 30.00 |
| 409 | CE1 | TYR | 55 | 139.992 | -4.259 | -9.260 | 1.00 | 30.00 |
| 410 | CD2 | TYR | 55 | 141.920 | -5.261 | -10.954 | 1.00 | 30.00 |
| 411 | CE2 | TYR | 55 | 141.169 | -6.129 | -10.191 | 1.00 | 30.00 |
| 412 | CZ | TYR | 55 | 140.212 | -5.610 | -9.352 | 1.00 | 30.00 |
| 413 | C | TYR | 55 | 144.940 | -3.495 | -11.066 | 1.00 | 30.00 |
| 414 | O | TYR | 55 | 144.973 | -4.672 | -10.701 | 1.00 | 30.00 |
| 415 | OH | TYR | 55 | 139.438 | -6.428 | -8.585 | 1.00 | 30.00 |
| 416 | N | PHE | 56 | 145.890 | -3.019 | -11.854 | 1.00 | 30.00 |
| 417 | CA | PHE | 56 | 146.894 | -4.018 | -12.214 | 1.00 | 30.00 |
| 418 | CB | PHE | 56 | 147.140 | -3.972 | -13.718 | 1.00 | 30.00 |
| 419 | CG | PHE | 56 | 145.953 | -4.489 | -14.513 | 1.00 | 30.00 |
| 420 | CD1 | PHE | 56 | 145.902 | -4.374 | -15.894 | 1.00 | 30.00 |
| 421 | CD2 | PHE | 56 | 144.860 | -5.072 | -13.854 | 1.00 | 30.00 |
| 422 | CE1 | PHE | 56 | 144.782 | -4.827 | -16.606 | 1.00 | 30.00 |
| 423 | CE2 | PHE | 56 | 143.744 | -5.522 | -14.555 | 1.00 | 30.00 |
| 424 | CZ | PHE | 56 | 143.702 | -5.400 | -15.927 | 1.00 | 30.00 |
| 425 | C | PHE | 56 | 148.144 | -4.002 | -11.349 | 1.00 | 30.00 |
| 426 | O | PHE | 56 | 148.644 | -5.051 | -10.944 | 1.00 | 30.00 |
| 427 | N | THR | 57 | 148.614 | -2.812 | -11.025 | 1.00 | 30.00 |
| 428 | CA | THR | 57 | 149.738 | -2.650 | -10.133 | 1.00 | 30.00 |
| 429 | CB | THR | 57 | 151.057 | -2.470 | -10.875 | 1.00 | 30.00 |
| 430 | OG1 | THR | 57 | 151.244 | -3.554 | -11.792 | 1.00 | 30.00 |
| 431 | CG2 | THR | 57 | 152.205 | -2.468 | -9.883 | 1.00 | 30.00 |
| 432 | C | THR | 57 | 149.331 | -1.368 | -9.447 | 1.00 | 30.00 |
| 433 | O | THR | 57 | 149.179 | -0.330 | -10.091 | 1.00 | 30.00 |
| 434 | N | GLY | 58 | 149.133 | -1.442 | -8.141 | 1.00 | 30.00 |
| 435 | CA | GLY | 58 | 148.667 | -0.280 | -7.411 | 1.00 | 30.00 |
| 436 | C | GLY | 58 | 149.544 | 0.869 | -6.953 | 1.00 | 30.00 |
| 437 | O | GLY | 58 | 150.013 | 0.851 | -5.813 | 1.00 | 30.00 |
| 438 | N | VAL | 59 | 149.774 | 1.852 | -7.826 | 1.00 | 30.00 |
| 439 | CA | VAL | 59 | 150.519 | 3.051 | -7.443 | 1.00 | 30.00 |
| 440 | CB | VAL | 59 | 149.865 | 3.607 | -6.146 | 1.00 | 30.00 |
| 441 | CG1 | VAL | 59 | 150.767 | 4.579 | -5.459 | 1.00 | 30.00 |
| 442 | CG2 | VAL | 59 | 148.538 | 4.257 | -6.486 | 1.00 | 30.00 |
| 443 | C | VAL | 59 | 152.060 | 3.049 | -7.284 | 1.00 | 30.00 |
| 444 | O | VAL | 59 | 152.616 | 2.332 | -6.445 | 1.00 | 30.00 |
| 445 | N | HIS | 60 | 152.725 | 3.892 | -8.087 | 1.00 | 30.00 |
| 446 | CA | HIS | 60 | 154.192 | 4.069 | -8.077 | 1.00 | 30.00 |
| 447 | CB | HIS | 60 | 154.691 | 4.744 | -9.371 | 1.00 | 30.00 |
| 448 | CG | HIS | 60 | 154.563 | 3.906 | -10.607 | 1.00 | 30.00 |
| 449 | CD2 | HIS | 60 | 153.904 | 4.131 | -11.768 | 1.00 | 30.00 |
| 450 | ND1 | HIS | 60 | 155.199 | 2.692 | -10.757 | 1.00 | 30.00 |
| 451 | CE1 | HIS | 60 | 154.936 | 2.204 | -11.958 | 1.00 | 30.00 |

| 452 | NE2 | HIS | 60 | 154.153 | 3.058 | -12.591 | 1.00 | 30.00 |
| 453 | C | HIS | 60 | 154.597 | 4.994 | -6.927 | 1.00 | 30.00 |
| 454 | O | HIS | 60 | 154.911 | 4.553 | -5.817 | 1.00 | 30.00 |
| 455 | N | ASP | 61 | 154.594 | 6.293 | -7.236 | 1.00 | 30.00 |
| 456 | CA | ASP | 61 | 154.949 | 7.348 | -6.290 | 1.00 | 30.00 |
| 457 | CB | ASP | 61 | 154.780 | 8.738 | -6.919 | 1.00 | 30.00 |
| 458 | CG | ASP | 61 | 155.718 | 8.980 | -8.075 | 1.00 | 30.00 |
| 459 | OD1 | ASP | 61 | 156.935 | 8.785 | -7.894 | 1.00 | 30.00 |
| 460 | OD2 | ASP | 61 | 155.240 | 9.375 | -9.160 | 1.00 | 30.00 |
| 461 | C | ASP | 61 | 154.106 | 7.305 | -5.033 | 1.00 | 30.00 |
| 462 | O | ASP | 61 | 152.872 | 7.219 | -5.084 | 1.00 | 30.00 |
| 463 | N | ALA | 62 | 154.792 | 7.370 | -3.900 | 1.00 | 30.00 |
| 464 | CA | ALA | 62 | 154.123 | 7.379 | -2.618 | 1.00 | 30.00 |
| 465 | CB | ALA | 62 | 155.153 | 7.404 | -1.478 | 1.00 | 30.00 |
| 466 | C | ALA | 62 | 153.286 | 8.653 | -2.615 | 1.00 | 30.00 |
| 467 | O | ALA | 62 | 153.817 | 9.734 | -2.390 | 1.00 | 30.00 |
| 468 | N | ASN | 63 | 151.993 | 8.521 | -2.906 | 1.00 | 30.00 |
| 469 | CA | ASN | 63 | 151.050 | 9.644 | -2.921 | 1.00 | 30.00 |
| 470 | CB | ASN | 63 | 151.390 | 10.675 | -1.832 | 1.00 | 30.00 |
| 471 | CG | ASN | 63 | 151.733 | 10.042 | -0.500 | 1.00 | 30.00 |
| 472 | OD1 | ASN | 63 | 151.021 | 9.169 | -0.017 | 1.00 | 30.00 |
| 473 | ND2 | ASN | 63 | 152.831 | 10.492 | 0.107 | 1.00 | 30.00 |
| 474 | C | ASN | 63 | 150.953 | 10.400 | -4.241 | 1.00 | 30.00 |
| 475 | O | ASN | 63 | 149.864 | 10.759 | -4.683 | 1.00 | 30.00 |
| 476 | N | ASP | 64 | 152.096 | 10.651 | -4.861 | 1.00 | 30.00 |
| 477 | CA | ASP | 64 | 152.140 | 11.414 | -6.101 | 1.00 | 30.00 |
| 478 | CB | ASP | 64 | 153.555 | 11.954 | -6.314 | 1.00 | 30.00 |
| 479 | CG | ASP | 64 | 154.056 | 12.749 | -5.120 | 1.00 | 30.00 |
| 480 | OD1 | ASP | 64 | 153.371 | 13.713 | -4.713 | 1.00 | 30.00 |
| 481 | OD2 | ASP | 64 | 155.132 | 12.406 | -4.588 | 1.00 | 30.00 |
| 482 | C | ASP | 64 | 151.677 | 10.679 | -7.348 | 1.00 | 30.00 |
| 483 | O | ASP | 64 | 151.426 | 11.304 | -8.378 | 1.00 | 30.00 |
| 484 | N | LYS | 65 | 151.564 | 9.359 | -7.259 | 1.00 | 30.00 |
| 485 | CA | LYS | 65 | 151.128 | 8.563 | -8.398 | 1.00 | 30.00 |
| 486 | CB | LYS | 65 | 150.877 | 7.119 | -7.963 | 1.00 | 30.00 |
| 487 | CG | LYS | 65 | 151.125 | 6.090 | -9.058 | 1.00 | 30.00 |
| 488 | CD | LYS | 65 | 150.401 | 6.440 | -10.354 | 1.00 | 30.00 |
| 489 | CE | LYS | 65 | 151.054 | 5.694 | -11.526 | 1.00 | 30.00 |
| 490 | NZ | LYS | 65 | 150.570 | 6.149 | -12.875 | 1.00 | 30.00 |
| 491 | C | LYS | 65 | 149.845 | 9.185 | -8.946 | 1.00 | 30.00 |
| 492 | O | LYS | 65 | 148.903 | 9.428 | -8.194 | 1.00 | 30.00 |
| 493 | N | ARG | 66 | 149.814 | 9.447 | -10.252 | 1.00 | 30.00 |
| 494 | CA | ARG | 66 | 148.644 | 10.066 | -10.882 | 1.00 | 30.00 |
| 495 | CB | ARG | 66 | 148.937 | 10.415 | -12.349 | 1.00 | 30.00 |
| 496 | CG | ARG | 66 | 149.582 | 11.779 | -12.566 | 1.00 | 30.00 |
| 497 | CD | ARG | 66 | 149.562 | 12.159 | -14.043 | 1.00 | 30.00 |
| 498 | NE | ARG | 66 | 150.212 | 13.444 | -14.306 | 1.00 | 30.00 |
| 499 | CZ | ARG | 66 | 150.283 | 14.021 | -15.504 | 1.00 | 30.00 |
| 500 | NH1 | ARG | 66 | 149.744 | 13.434 | -16.567 | 1.00 | 30.00 |
| 501 | NH2 | ARG | 66 | 150.903 | 15.188 | -15.645 | 1.00 | 30.00 |
| 502 | C | ARG | 66 | 147.341 | 9.275 | -10.814 | 1.00 | 30.00 |
| 503 | O | ARG | 66 | 146.268 | 9.842 | -10.999 | 1.00 | 30.00 |

| 504 | N | PHE | 67 | 147.419 | 7.974 | -10.556 | 1.00 | 30.00 |
| 505 | CA | PHE | 67 | 146.201 | 7.167 | -10.472 | 1.00 | 30.00 |
| 506 | CB | PHE | 67 | 146.537 | 5.671 | -10.559 | 1.00 | 30.00 |
| 507 | CG | PHE | 67 | 146.973 | 5.223 | -11.931 | 1.00 | 30.00 |
| 508 | CD1 | PHE | 67 | 147.549 | 3.970 | -12.115 | 1.00 | 30.00 |
| 509 | CD2 | PHE | 67 | 146.826 | 6.061 | -13.038 | 1.00 | 30.00 |
| 510 | CE1 | PHE | 67 | 147.979 | 3.556 | -13.379 | 1.00 | 30.00 |
| 511 | CE2 | PHE | 67 | 147.250 | 5.658 | -14.307 | 1.00 | 30.00 |
| 512 | CZ | PHE | 67 | 147.828 | 4.402 | -14.476 | 1.00 | 30.00 |
| 513 | C | PHE | 67 | 145.395 | 7.466 | -9.201 | 1.00 | 30.00 |
| 514 | O | PHE | 67 | 144.168 | 7.320 | -9.189 | 1.00 | 30.00 |
| 515 | N | GLN | 68 | 146.081 | 7.880 | -8.137 | 1.00 | 30.00 |
| 516 | CA | GLN | 68 | 145.406 | 8.215 | -6.888 | 1.00 | 30.00 |
| 517 | CB | GLN | 68 | 146.401 | 8.770 | -5.861 | 1.00 | 30.00 |
| 518 | CG | GLN | 68 | 147.415 | 7.777 | -5.285 | 1.00 | 30.00 |
| 519 | CD | GLN | 68 | 146.872 | 7.007 | -4.094 | 1.00 | 30.00 |
| 520 | OE1 | GLN | 68 | 147.631 | 6.429 | -3.310 | 1.00 | 30.00 |
| 521 | NE2 | GLN | 68 | 145.553 | 6.995 | -3.953 | 1.00 | 30.00 |
| 522 | C | GLN | 68 | 144.392 | 9.301 | -7.245 | 1.00 | 30.00 |
| 523 | O | GLN | 68 | 143.376 | 9.485 | -6.571 | 1.00 | 30.00 |
| 524 | N | GLU | 69 | 144.674 | 10.008 | -8.333 | 1.00 | 30.00 |
| 525 | CA | GLU | 69 | 143.812 | 11.085 | -8.778 | 1.00 | 30.00 |
| 526 | CB | GLU | 69 | 144.635 | 12.140 | -9.511 | 1.00 | 30.00 |
| 527 | CG | GLU | 69 | 145.570 | 12.878 | -8.575 | 1.00 | 30.00 |
| 528 | CD | GLU | 69 | 144.872 | 13.276 | -7.284 | 1.00 | 30.00 |
| 529 | OE1 | GLU | 69 | 143.770 | 13.867 | -7.365 | 1.00 | 30.00 |
| 530 | OE2 | GLU | 69 | 145.426 | 12.996 | -6.196 | 1.00 | 30.00 |
| 531 | C | GLU | 69 | 142.638 | 10.665 | -9.630 | 1.00 | 30.00 |
| 532 | O | GLU | 69 | 141.523 | 11.126 | -9.402 | 1.00 | 30.00 |
| 533 | N | THR | 70 | 142.856 | 9.799 | -10.609 | 1.00 | 30.00 |
| 534 | CA | THR | 70 | 141.728 | 9.388 | -11.428 | 1.00 | 30.00 |
| 535 | CB | THR | 70 | 142.179 | 8.618 | -12.673 | 1.00 | 30.00 |
| 536 | OG1 | THR | 70 | 143.356 | 9.232 | -13.220 | 1.00 | 30.00 |
| 537 | CG2 | THR | 70 | 141.071 | 8.659 | -13.729 | 1.00 | 30.00 |
| 538 | C | THR | 70 | 140.669 | 8.587 | -10.634 | 1.00 | 30.00 |
| 539 | O | THR | 70 | 139.609 | 8.261 | -11.177 | 1.00 | 30.00 |
| 540 | N | PHE | 71 | 140.961 | 8.256 | -9.367 | 1.00 | 30.00 |
| 541 | CA | PHE | 71 | 139.991 | 7.594 | -8.474 | 1.00 | 30.00 |
| 542 | CB | PHE | 71 | 140.681 | 6.909 | -7.300 | 1.00 | 30.00 |
| 543 | CG | PHE | 71 | 140.120 | 7.321 | -5.946 | 1.00 | 30.00 |
| 544 | CD1 | PHE | 71 | 138.955 | 6.739 | -5.445 | 1.00 | 30.00 |
| 545 | CD2 | PHE | 71 | 140.731 | 8.327 | -5.196 | 1.00 | 30.00 |
| 546 | CE1 | PHE | 71 | 138.408 | 7.153 | -4.221 | 1.00 | 30.00 |
| 547 | CE2 | PHE | 71 | 140.193 | 8.748 | -3.974 | 1.00 | 30.00 |
| 548 | CZ | PHE | 71 | 139.032 | 8.160 | -3.487 | 1.00 | 30.00 |
| 549 | C | PHE | 71 | 139.172 | 8.766 | -7.900 | 1.00 | 30.00 |
| 550 | O | PHE | 71 | 137.944 | 8.725 | -7.812 | 1.00 | 30.00 |
| 551 | N | GLU | 72 | 139.906 | 9.799 | -7.489 | 1.00 | 30.00 |
| 552 | CA | GLU | 72 | 139.356 | 11.029 | -6.927 | 1.00 | 30.00 |
| 553 | CB | GLU | 72 | 140.500 | 12.017 | -6.688 | 1.00 | 30.00 |
| 554 | CG | GLU | 72 | 140.370 | 12.901 | -5.461 | 1.00 | 30.00 |
| 555 | CD | GLU | 72 | 140.977 | 12.284 | -4.210 | 1.00 | 30.00 |

| 556 | OE1 | GLU | 72 | 142.093 | 11.722 | -4.290 | 1.00 | 30.00 |
| 557 | OE2 | GLU | 72 | 140.342 | 12.376 | -3.138 | 1.00 | 30.00 |
| 558 | C | GLU | 72 | 138.386 | 11.614 | -7.956 | 1.00 | 30.00 |
| 559 | O | GLU | 72 | 137.332 | 12.145 | -7.607 | 1.00 | 30.00 |
| 560 | N | ASP | 73 | 138.763 | 11.492 | -9.225 | 1.00 | 30.00 |
| 561 | CA | ASP | 73 | 137.982 | 11.991 | -10.349 | 1.00 | 30.00 |
| 562 | CB | ASP | 73 | 138.891 | 12.170 | -11.564 | 1.00 | 30.00 |
| 563 | CG | ASP | 73 | 139.740 | 13.424 | -11.473 | 1.00 | 30.00 |
| 564 | OD1 | ASP | 73 | 140.337 | 13.680 | -10.402 | 1.00 | 30.00 |
| 565 | OD2 | ASP | 73 | 139.816 | 14.157 | -12.480 | 1.00 | 30.00 |
| 566 | C | ASP | 73 | 136.794 | 11.118 | -10.723 | 1.00 | 30.00 |
| 567 | O | ASP | 73 | 135.791 | 11.625 | -11.221 | 1.00 | 30.00 |
| 568 | N | VAL | 74 | 136.911 | 9.810 | -10.505 | 1.00 | 30.00 |
| 569 | CA | VAL | 74 | 135.818 | 8.878 | -10.808 | 1.00 | 30.00 |
| 570 | CB | VAL | 74 | 136.322 | 7.413 | -10.794 | 1.00 | 30.00 |
| 571 | CG1 | VAL | 74 | 135.159 | 6.461 | -10.643 | 1.00 | 30.00 |
| 572 | CG2 | VAL | 74 | 137.077 | 7.113 | -12.073 | 1.00 | 30.00 |
| 573 | C | VAL | 74 | 134.699 | 9.044 | -9.771 | 1.00 | 30.00 |
| 574 | O | VAL | 74 | 133.521 | 9.131 | -10.115 | 1.00 | 30.00 |
| 575 | N | PHE | 75 | 135.090 | 9.089 | -8.500 | 1.00 | 30.00 |
| 576 | CA | PHE | 75 | 134.154 | 9.266 | -7.405 | 1.00 | 30.00 |
| 577 | CB | PHE | 75 | 134.633 | 8.478 | -6.181 | 1.00 | 30.00 |
| 578 | CG | PHE | 75 | 134.491 | 6.993 | -6.350 | 1.00 | 30.00 |
| 579 | CD1 | PHE | 75 | 135.316 | 6.296 | -7.230 | 1.00 | 30.00 |
| 580 | CD2 | PHE | 75 | 133.460 | 6.305 | -5.714 | 1.00 | 30.00 |
| 581 | CE1 | PHE | 75 | 135.106 | 4.936 | -7.478 | 1.00 | 30.00 |
| 582 | CE2 | PHE | 75 | 133.243 | 4.942 | -5.956 | 1.00 | 30.00 |
| 583 | CZ | PHE | 75 | 134.064 | 4.260 | -6.839 | 1.00 | 30.00 |
| 584 | C | PHE | 75 | 134.032 | 10.753 | -7.114 | 1.00 | 30.00 |
| 585 | O | PHE | 75 | 134.223 | 11.223 | -5.993 | 1.00 | 30.00 |
| 586 | N | SER | 76 | 133.710 | 11.482 | -8.173 | 1.00 | 30.00 |
| 587 | CA | SER | 76 | 133.541 | 12.923 | -8.132 | 1.00 | 30.00 |
| 588 | CB | SER | 76 | 134.385 | 13.564 | -9.229 | 1.00 | 30.00 |
| 589 | OG | SER | 76 | 133.939 | 13.136 | -10.506 | 1.00 | 30.00 |
| 590 | C | SER | 76 | 132.066 | 13.223 | -8.382 | 1.00 | 30.00 |
| 591 | O | SER | 76 | 131.583 | 13.092 | -9.514 | 1.00 | 30.00 |
| 592 | N | ASP | 77 | 131.358 | 13.622 | -7.327 | 1.00 | 30.00 |
| 593 | CA | ASP | 77 | 129.930 | 13.930 | -7.403 | 1.00 | 30.00 |
| 594 | CB | ASP | 77 | 129.128 | 12.633 | -7.606 | 1.00 | 30.00 |
| 595 | CG | ASP | 77 | 127.676 | 12.881 | -8.005 | 1.00 | 30.00 |
| 596 | OD1 | ASP | 77 | 126.947 | 13.577 | -7.255 | 1.00 | 30.00 |
| 597 | OD2 | ASP | 77 | 127.266 | 12.364 | -9.072 | 1.00 | 30.00 |
| 598 | C | ASP | 77 | 129.593 | 14.551 | -6.053 | 1.00 | 30.00 |
| 599 | O | ASP | 77 | 129.835 | 13.936 | -5.015 | 1.00 | 30.00 |
| 600 | N | ARG | 78 | 129.044 | 15.763 | -6.067 | 1.00 | 30.00 |
| 601 | CA | ARG | 78 | 128.707 | 16.475 | -4.832 | 1.00 | 30.00 |
| 602 | CB | ARG | 78 | 127.722 | 17.617 | -5.130 | 1.00 | 30.00 |
| 603 | CG | ARG | 78 | 126.485 | 17.187 | -5.892 | 1.00 | 30.00 |
| 604 | CD | ARG | 78 | 125.545 | 18.356 | -6.169 | 1.00 | 30.00 |
| 605 | NE | ARG | 78 | 124.377 | 17.928 | -6.939 | 1.00 | 30.00 |
| 606 | CZ | ARG | 78 | 123.395 | 18.732 | -7.332 | 1.00 | 30.00 |
| 607 | NH1 | ARG | 78 | 123.428 | 20.024 | -7.032 | 1.00 | 30.00 |

| 608 | NH2 | ARG | 78 | 122.377 | 18.244 | -8.030 | 1.00 | 30.00 |
| 609 | C | ARG | 78 | 128.164 | 15.607 | -3.689 | 1.00 | 30.00 |
| 610 | O | ARG | 78 | 128.327 | 15.957 | -2.514 | 1.00 | 30.00 |
| 611 | N | ALA | 79 | 127.524 | 14.485 | -4.022 | 1.00 | 30.00 |
| 612 | CA | ALA | 79 | 126.974 | 13.599 | -2.998 | 1.00 | 30.00 |
| 613 | CB | ALA | 79 | 126.124 | 12.525 | -3.642 | 1.00 | 30.00 |
| 614 | C | ALA | 79 | 128.086 | 12.964 | -2.167 | 1.00 | 30.00 |
| 615 | O | ALA | 79 | 128.016 | 12.949 | -0.939 | 1.00 | 30.00 |
| 616 | N | LEU | 80 | 129.111 | 12.445 | -2.842 | 1.00 | 30.00 |
| 617 | CA | LEU | 80 | 130.249 | 11.813 | -2.173 | 1.00 | 30.00 |
| 618 | CB | LEU | 80 | 130.865 | 10.733 | -3.060 | 1.00 | 30.00 |
| 619 | CG | LEU | 80 | 129.990 | 9.709 | -3.771 | 1.00 | 30.00 |
| 620 | CD1 | LEU | 80 | 130.899 | 8.830 | -4.594 | 1.00 | 30.00 |
| 621 | CD2 | LEU | 80 | 129.193 | 8.884 | -2.779 | 1.00 | 30.00 |
| 622 | C | LEU | 80 | 131.331 | 12.850 | -1.878 | 1.00 | 30.00 |
| 623 | O | LEU | 80 | 132.318 | 12.554 | -1.201 | 1.00 | 30.00 |
| 624 | N | ARG | 81 | 131.138 | 14.055 | -2.416 | 1.00 | 30.00 |
| 625 | CA | ARG | 81 | 132.061 | 15.175 | -2.256 | 1.00 | 30.00 |
| 626 | CB | ARG | 81 | 131.364 | 16.480 | -2.686 | 1.00 | 30.00 |
| 627 | CG | ARG | 81 | 132.135 | 17.766 | -2.359 | 1.00 | 30.00 |
| 628 | CD | ARG | 81 | 131.369 | 19.046 | -2.732 | 1.00 | 30.00 |
| 629 | NE | ARG | 81 | 131.386 | 19.319 | -4.170 | 1.00 | 30.00 |
| 630 | CZ | ARG | 81 | 130.932 | 20.437 | -4.728 | 1.00 | 30.00 |
| 631 | NH1 | ARG | 81 | 130.420 | 21.400 | -3.972 | 1.00 | 30.00 |
| 632 | NH2 | ARG | 81 | 130.994 | 20.596 | -6.043 | 1.00 | 30.00 |
| 633 | C | ARG | 81 | 132.641 | 15.344 | -0.851 | 1.00 | 30.00 |
| 634 | O | ARG | 81 | 133.613 | 16.073 | -0.671 | 1.00 | 30.00 |
| 635 | N | ASN | 82 | 132.071 | 14.685 | 0.149 | 1.00 | 30.00 |
| 636 | CA | ASN | 82 | 132.608 | 14.843 | 1.491 | 1.00 | 30.00 |
| 637 | CB | ASN | 82 | 131.939 | 16.048 | 2.144 | 1.00 | 30.00 |
| 638 | CG | ASN | 82 | 132.750 | 16.609 | 3.282 | 1.00 | 30.00 |
| 639 | OD1 | ASN | 82 | 133.919 | 16.964 | 3.106 | 1.00 | 30.00 |
| 640 | ND2 | ASN | 82 | 132.138 | 16.699 | 4.459 | 1.00 | 30.00 |
| 641 | C | ASN | 82 | 132.475 | 13.610 | 2.395 | 1.00 | 30.00 |
| 642 | O | ASN | 82 | 132.471 | 13.729 | 3.622 | 1.00 | 30.00 |
| 643 | N | ILE | 83 | 132.391 | 12.427 | 1.791 | 1.00 | 30.00 |
| 644 | CA | ILE | 83 | 132.241 | 11.185 | 2.545 | 1.00 | 30.00 |
| 645 | CB | ILE | 83 | 131.316 | 10.191 | 1.802 | 1.00 | 30.00 |
| 646 | CG2 | ILE | 83 | 130.962 | 9.032 | 2.728 | 1.00 | 30.00 |
| 647 | CG1 | ILE | 83 | 130.042 | 10.894 | 1.322 | 1.00 | 30.00 |
| 648 | CD1 | ILE | 83 | 129.082 | 11.286 | 2.434 | 1.00 | 30.00 |
| 649 | C | ILE | 83 | 133.565 | 10.459 | 2.803 | 1.00 | 30.00 |
| 650 | O | ILE | 83 | 134.266 | 10.071 | 1.858 | 1.00 | 30.00 |
| 651 | N | PRO | 84 | 133.919 | 10.258 | 4.090 | 1.00 | 30.00 |
| 652 | CD | PRO | 84 | 133.171 | 10.732 | 5.268 | 1.00 | 30.00 |
| 653 | CA | PRO | 84 | 135.148 | 9.571 | 4.508 | 1.00 | 30.00 |
| 654 | CB | PRO | 84 | 134.960 | 9.410 | 6.017 | 1.00 | 30.00 |
| 655 | CG | PRO | 84 | 134.191 | 10.599 | 6.385 | 1.00 | 30.00 |
| 656 | C | PRO | 84 | 135.289 | 8.203 | 3.832 | 1.00 | 30.00 |
| 657 | O | PRO | 84 | 134.295 | 7.503 | 3.619 | 1.00 | 30.00 |
| 658 | N | TRP | 85 | 136.522 | 7.830 | 3.500 | 1.00 | 30.00 |
| 659 | CA | TRP | 85 | 136.805 | 6.535 | 2.885 | 1.00 | 30.00 |

| | | | | | | | |
|---|---|---|---|---|---|---|---|
| 660 | CB | TRP | 85 | 137.419 | 6.683 | 1.490 | 1.00 | 30.00 |
| 661 | CG | TRP | 85 | 136.452 | 6.791 | 0.374 | 1.00 | 30.00 |
| 662 | CD2 | TRP | 85 | 136.237 | 5.835 | -0.673 | 1.00 | 30.00 |
| 663 | CE2 | TRP | 85 | 135.231 | 6.357 | -1.516 | 1.00 | 30.00 |
| 664 | CE3 | TRP | 85 | 136.793 | 4.586 | -0.979 | 1.00 | 30.00 |
| 665 | CD1 | TRP | 85 | 135.599 | 7.820 | 0.132 | 1.00 | 30.00 |
| 666 | NE1 | TRP | 85 | 134.860 | 7.572 | -1.000 | 1.00 | 30.00 |
| 667 | CZ2 | TRP | 85 | 134.766 | 5.676 | -2.649 | 1.00 | 30.00 |
| 668 | CZ3 | TRP | 85 | 136.330 | 3.905 | -2.108 | 1.00 | 30.00 |
| 669 | CH2 | TRP | 85 | 135.326 | 4.457 | -2.926 | 1.00 | 30.00 |
| 670 | C | TRP | 85 | 137.823 | 5.816 | 3.749 | 1.00 | 30.00 |
| 671 | O | TRP | 85 | 138.817 | 6.416 | 4.157 | 1.00 | 30.00 |
| 672 | N | TYR | 86 | 137.565 | 4.541 | 4.032 | 1.00 | 30.00 |
| 673 | CA | TYR | 86 | 138.492 | 3.710 | 4.798 | 1.00 | 30.00 |
| 674 | CB | TYR | 86 | 137.797 | 3.093 | 6.013 | 1.00 | 30.00 |
| 675 | CG | TYR | 86 | 137.431 | 4.141 | 7.023 | 1.00 | 30.00 |
| 676 | CD1 | TYR | 86 | 138.417 | 4.832 | 7.726 | 1.00 | 30.00 |
| 677 | CE1 | TYR | 86 | 138.089 | 5.883 | 8.581 | 1.00 | 30.00 |
| 678 | CD2 | TYR | 86 | 136.107 | 4.517 | 7.207 | 1.00 | 30.00 |
| 679 | CE2 | TYR | 86 | 135.767 | 5.562 | 8.056 | 1.00 | 30.00 |
| 680 | CZ | TYR | 86 | 136.759 | 6.242 | 8.738 | 1.00 | 30.00 |
| 681 | OH | TYR | 86 | 136.414 | 7.287 | 9.557 | 1.00 | 30.00 |
| 682 | C | TYR | 86 | 138.961 | 2.652 | 3.807 | 1.00 | 30.00 |
| 683 | O | TYR | 86 | 138.171 | 1.838 | 3.338 | 1.00 | 30.00 |
| 684 | N | VAL | 87 | 140.249 | 2.690 | 3.479 | 1.00 | 30.00 |
| 685 | CA | VAL | 87 | 140.829 | 1.793 | 2.490 | 1.00 | 30.00 |
| 686 | CB | VAL | 87 | 141.821 | 2.577 | 1.603 | 1.00 | 30.00 |
| 687 | CG1 | VAL | 87 | 142.368 | 1.690 | 0.495 | 1.00 | 30.00 |
| 688 | CG2 | VAL | 87 | 141.126 | 3.796 | 1.020 | 1.00 | 30.00 |
| 689 | C | VAL | 87 | 141.523 | 0.538 | 3.015 | 1.00 | 30.00 |
| 690 | O | VAL | 87 | 141.974 | 0.479 | 4.163 | 1.00 | 30.00 |
| 691 | N | LEU | 88 | 141.589 | -0.464 | 2.138 | 1.00 | 30.00 |
| 692 | CA | LEU | 88 | 142.224 | -1.746 | 2.420 | 1.00 | 30.00 |
| 693 | CB | LEU | 88 | 141.193 | -2.870 | 2.529 | 1.00 | 30.00 |
| 694 | CG | LEU | 88 | 140.844 | -3.287 | 3.947 | 1.00 | 30.00 |
| 695 | CD1 | LEU | 88 | 140.070 | -4.586 | 3.919 | 1.00 | 30.00 |
| 696 | CD2 | LEU | 88 | 142.127 | -3.440 | 4.736 | 1.00 | 30.00 |
| 697 | C | LEU | 88 | 143.180 | -2.118 | 1.311 | 1.00 | 30.00 |
| 698 | O | LEU | 88 | 143.013 | -1.713 | 0.158 | 1.00 | 30.00 |
| 699 | N | ALA | 89 | 144.176 | -2.912 | 1.678 | 1.00 | 30.00 |
| 700 | CA | ALA | 89 | 145.163 | -3.389 | 0.741 | 1.00 | 30.00 |
| 701 | CB | ALA | 89 | 146.429 | -3.708 | 1.496 | 1.00 | 30.00 |
| 702 | C | ALA | 89 | 144.641 | -4.647 | 0.018 | 1.00 | 30.00 |
| 703 | O | ALA | 89 | 144.256 | -5.637 | 0.653 | 1.00 | 30.00 |
| 704 | N | GLY | 90 | 144.600 | -4.599 | -1.307 | 1.00 | 30.00 |
| 705 | CA | GLY | 90 | 144.171 | -5.765 | -2.069 | 1.00 | 30.00 |
| 706 | C | GLY | 90 | 145.430 | -6.482 | -2.544 | 1.00 | 30.00 |
| 707 | O | GLY | 90 | 146.519 | -6.119 | -2.104 | 1.00 | 30.00 |
| 708 | N | ASN | 91 | 145.316 | -7.485 | -3.417 | 1.00 | 30.00 |
| 709 | CA | ASN | 91 | 146.517 | -8.169 | -3.906 | 1.00 | 30.00 |
| 710 | CB | ASN | 91 | 146.217 | -9.592 | -4.443 | 1.00 | 30.00 |
| 711 | CG | ASN | 91 | 145.086 | -9.631 | -5.461 | 1.00 | 30.00 |

| 712 | ND2 | ASN | 91 | 145.415 | -9.931 | -6.709 | 1.00 | 30.00 |
| 713 | C | ASN | 91 | 147.221 | -7.337 | -4.973 | 1.00 | 30.00 |
| 714 | O | ASN | 91 | 148.447 | -7.256 | -4.990 | 1.00 | 30.00 |
| 715 | OD1 | ASN | 91 | 143.934 | -9.412 | -5.122 | 1.00 | 30.00 |
| 716 | N | HIS | 92 | 146.451 | -6.705 | -5.847 | 1.00 | 30.00 |
| 717 | CA | HIS | 92 | 147.035 | -5.874 | -6.886 | 1.00 | 30.00 |
| 718 | CB | HIS | 92 | 145.973 | -5.490 | -7.896 | 1.00 | 30.00 |
| 719 | CG | HIS | 92 | 145.653 | -6.596 | -8.847 | 1.00 | 30.00 |
| 720 | CD2 | HIS | 92 | 144.741 | -7.597 | -8.777 | 1.00 | 30.00 |
| 721 | ND1 | HIS | 92 | 146.365 | -6.805 | -10.008 | 1.00 | 30.00 |
| 722 | CE1 | HIS | 92 | 145.906 | -7.883 | -10.615 | 1.00 | 30.00 |
| 723 | NE2 | HIS | 92 | 144.922 | -8.384 | -9.888 | 1.00 | 30.00 |
| 724 | C | HIS | 92 | 147.712 | -4.634 | -6.333 | 1.00 | 30.00 |
| 725 | O | HIS | 92 | 148.658 | -4.116 | -6.925 | 1.00 | 30.00 |
| 726 | N | ASP | 93 | 147.237 | -4.163 | -5.187 | 1.00 | 30.00 |
| 727 | CA | ASP | 93 | 147.834 | -2.992 | -4.562 | 1.00 | 30.00 |
| 728 | CB | ASP | 93 | 146.898 | -2.432 | -3.491 | 1.00 | 30.00 |
| 729 | CG | ASP | 93 | 145.544 | -2.021 | -4.057 | 1.00 | 30.00 |
| 730 | OD1 | ASP | 93 | 145.496 | -1.119 | -4.927 | 1.00 | 30.00 |
| 731 | OD2 | ASP | 93 | 144.523 | -2.602 | -3.629 | 1.00 | 30.00 |
| 732 | C | ASP | 93 | 149.177 | -3.379 | -3.943 | 1.00 | 30.00 |
| 733 | O | ASP | 93 | 149.985 | -2.523 | -3.612 | 1.00 | 30.00 |
| 734 | N | HIS | 94 | 149.410 | -4.679 | -3.789 | 1.00 | 30.00 |
| 735 | CA | HIS | 94 | 150.665 | -5.155 | -3.228 | 1.00 | 30.00 |
| 736 | CB | HIS | 94 | 150.414 | -6.381 | -2.348 | 1.00 | 30.00 |
| 737 | CG | HIS | 94 | 150.090 | -6.050 | -0.923 | 1.00 | 30.00 |
| 738 | CD2 | HIS | 94 | 148.911 | -6.023 | -0.258 | 1.00 | 30.00 |
| 739 | ND1 | HIS | 94 | 151.047 | -5.669 | -0.009 | 1.00 | 30.00 |
| 740 | CE1 | HIS | 94 | 150.476 | -5.423 | 1.156 | 1.00 | 30.00 |
| 741 | NE2 | HIS | 94 | 149.178 | -5.630 | 1.030 | 1.00 | 30.00 |
| 742 | C | HIS | 94 | 151.678 | -5.476 | -4.339 | 1.00 | 30.00 |
| 743 | O | HIS | 94 | 152.786 | -5.949 | -4.070 | 1.00 | 30.00 |
| 744 | N | LEU | 95 | 151.282 | -5.231 | -5.587 | 1.00 | 30.00 |
| 745 | CA | LEU | 95 | 152.162 | -5.439 | -6.729 | 1.00 | 30.00 |
| 746 | CB | LEU | 95 | 151.371 | -5.909 | -7.957 | 1.00 | 30.00 |
| 747 | CG | LEU | 95 | 150.837 | -7.355 | -7.943 | 1.00 | 30.00 |
| 748 | CD1 | LEU | 95 | 150.032 | -7.619 | -9.195 | 1.00 | 30.00 |
| 749 | CD2 | LEU | 95 | 151.981 | -8.338 | -7.856 | 1.00 | 30.00 |
| 750 | C | LEU | 95 | 152.769 | -4.063 | -6.978 | 1.00 | 30.00 |
| 751 | O | LEU | 95 | 153.680 | -3.889 | -7.785 | 1.00 | 30.00 |
| 752 | N | GLY | 96 | 152.234 | -3.088 | -6.252 | 1.00 | 30.00 |
| 753 | CA | GLY | 96 | 152.702 | -1.720 | -6.338 | 1.00 | 30.00 |
| 754 | C | GLY | 96 | 153.147 | -1.279 | -4.953 | 1.00 | 30.00 |
| 755 | O | GLY | 96 | 153.381 | -2.122 | -4.069 | 1.00 | 30.00 |
| 756 | N | ASN | 97 | 153.257 | 0.034 | -4.756 | 1.00 | 30.00 |
| 757 | CA | ASN | 97 | 153.692 | 0.595 | -3.480 | 1.00 | 30.00 |
| 758 | CB | ASN | 97 | 154.437 | 1.922 | -3.710 | 1.00 | 30.00 |
| 759 | CG | ASN | 97 | 154.997 | 2.522 | -2.418 | 1.00 | 30.00 |
| 760 | OD1 | ASN | 97 | 154.719 | 2.024 | -1.315 | 1.00 | 30.00 |
| 761 | ND2 | ASN | 97 | 155.778 | 3.608 | -2.546 | 1.00 | 30.00 |
| 762 | C | ASN | 97 | 152.501 | 0.824 | -2.561 | 1.00 | 30.00 |
| 763 | O | ASN | 97 | 151.706 | 1.739 | -2.787 | 1.00 | 30.00 |

| 764 | N | VAL | 98 | 152.385 | -0.008 | -1.527 | 1.00 | 30.00 |
| 765 | CA | VAL | 98 | 151.292 | 0.102 | -0.559 | 1.00 | 30.00 |
| 766 | CB | VAL | 98 | 151.119 | -1.228 | 0.231 | 1.00 | 30.00 |
| 767 | CG1 | VAL | 98 | 150.361 | -0.999 | 1.527 | 1.00 | 30.00 |
| 768 | CG2 | VAL | 98 | 150.343 | -2.209 | -0.621 | 1.00 | 30.00 |
| 769 | C | VAL | 98 | 151.495 | 1.276 | 0.405 | 1.00 | 30.00 |
| 770 | O | VAL | 98 | 150.550 | 2.009 | 0.725 | 1.00 | 30.00 |
| 771 | N | SER | 99 | 152.733 | 1.459 | 0.855 | 1.00 | 30.00 |
| 772 | CA | SER | 99 | 153.065 | 2.547 | 1.762 | 1.00 | 30.00 |
| 773 | CB | SER | 99 | 154.567 | 2.580 | 1.997 | 1.00 | 30.00 |
| 774 | OG | SER | 99 | 155.018 | 1.296 | 2.372 | 1.00 | 30.00 |
| 775 | C | SER | 99 | 152.618 | 3.841 | 1.110 | 1.00 | 30.00 |
| 776 | O | SER | 99 | 152.350 | 4.834 | 1.792 | 1.00 | 30.00 |
| 777 | N | ALA | 100 | 152.542 | 3.809 | -0.220 | 1.00 | 30.00 |
| 778 | CA | ALA | 100 | 152.121 | 4.948 | -1.025 | 1.00 | 30.00 |
| 779 | CB | ALA | 100 | 152.297 | 4.632 | -2.492 | 1.00 | 30.00 |
| 780 | C | ALA | 100 | 150.665 | 5.291 | -0.747 | 1.00 | 30.00 |
| 781 | O | ALA | 100 | 150.330 | 6.435 | -0.447 | 1.00 | 30.00 |
| 782 | N | GLN | 101 | 149.795 | 4.296 | -0.851 | 1.00 | 30.00 |
| 783 | CA | GLN | 101 | 148.384 | 4.526 | -0.599 | 1.00 | 30.00 |
| 784 | CB | GLN | 101 | 147.572 | 3.283 | -0.961 | 1.00 | 30.00 |
| 785 | CG | GLN | 101 | 147.754 | 2.791 | -2.384 | 1.00 | 30.00 |
| 786 | CD | GLN | 101 | 146.773 | 1.681 | -2.723 | 1.00 | 30.00 |
| 787 | OE1 | GLN | 101 | 146.866 | 1.048 | -3.779 | 1.00 | 30.00 |
| 788 | NE2 | GLN | 101 | 145.817 | 1.446 | -1.827 | 1.00 | 30.00 |
| 789 | C | GLN | 101 | 148.170 | 4.876 | 0.872 | 1.00 | 30.00 |
| 790 | O | GLN | 101 | 147.236 | 5.580 | 1.222 | 1.00 | 30.00 |
| 791 | N | ILE | 102 | 149.027 | 4.368 | 1.744 | 1.00 | 30.00 |
| 792 | CA | ILE | 102 | 148.891 | 4.678 | 3.161 | 1.00 | 30.00 |
| 793 | CB | ILE | 102 | 149.879 | 3.860 | 4.013 | 1.00 | 30.00 |
| 794 | CG2 | ILE | 102 | 149.891 | 4.384 | 5.440 | 1.00 | 30.00 |
| 795 | CG1 | ILE | 102 | 149.496 | 2.380 | 3.966 | 1.00 | 30.00 |
| 796 | CD1 | ILE | 102 | 150.504 | 1.458 | 4.624 | 1.00 | 30.00 |
| 797 | C | ILE | 102 | 149.173 | 6.164 | 3.370 | 1.00 | 30.00 |
| 798 | O | ILE | 102 | 148.377 | 6.883 | 3.971 | 1.00 | 30.00 |
| 799 | N | ALA | 103 | 150.311 | 6.618 | 2.858 | 1.00 | 30.00 |
| 800 | CA | ALA | 103 | 150.713 | 8.010 | 2.989 | 1.00 | 30.00 |
| 801 | CB | ALA | 103 | 152.126 | 8.187 | 2.457 | 1.00 | 30.00 |
| 802 | C | ALA | 103 | 149.756 | 8.945 | 2.256 | 1.00 | 30.00 |
| 803 | O | ALA | 103 | 149.598 | 10.107 | 2.633 | 1.00 | 30.00 |
| 804 | N | TYR | 104 | 149.112 | 8.432 | 1.212 | 1.00 | 30.00 |
| 805 | CA | TYR | 104 | 148.191 | 9.233 | 0.422 | 1.00 | 30.00 |
| 806 | CB | TYR | 104 | 147.545 | 8.391 | -0.661 | 1.00 | 30.00 |
| 807 | CG | TYR | 104 | 146.740 | 9.220 | -1.612 | 1.00 | 30.00 |
| 808 | CD1 | TYR | 104 | 147.366 | 10.120 | -2.465 | 1.00 | 30.00 |
| 809 | CE1 | TYR | 104 | 146.637 | 10.894 | -3.345 | 1.00 | 30.00 |
| 810 | CD2 | TYR | 104 | 145.350 | 9.117 | -1.658 | 1.00 | 30.00 |
| 811 | CE2 | TYR | 104 | 144.605 | 9.894 | -2.540 | 1.00 | 30.00 |
| 812 | CZ | TYR | 104 | 145.262 | 10.778 | -3.380 | 1.00 | 30.00 |
| 813 | OH | TYR | 104 | 144.553 | 11.532 | -4.274 | 1.00 | 30.00 |
| 814 | C | TYR | 104 | 147.098 | 9.850 | 1.273 | 1.00 | 30.00 |
| 815 | O | TYR | 104 | 146.441 | 10.806 | 0.859 | 1.00 | 30.00 |

| 816 | N | SER | 105 | 146.902 | 9.294 | 2.462 | 1.00 | 30.00 |
| 817 | CA | SER | 105 | 145.885 | 9.790 | 3.375 | 1.00 | 30.00 |
| 818 | CB | SER | 105 | 145.605 | 8.749 | 4.457 | 1.00 | 30.00 |
| 819 | OG | SER | 105 | 146.735 | 8.561 | 5.286 | 1.00 | 30.00 |
| 820 | C | SER | 105 | 146.328 | 11.102 | 4.013 | 1.00 | 30.00 |
| 821 | O | SER | 105 | 145.703 | 11.587 | 4.955 | 1.00 | 30.00 |
| 822 | N | LYS | 106 | 147.421 | 11.660 | 3.498 | 1.00 | 30.00 |
| 823 | CA | LYS | 106 | 147.962 | 12.930 | 3.983 | 1.00 | 30.00 |
| 824 | CB | LYS | 106 | 149.460 | 12.796 | 4.271 | 1.00 | 30.00 |
| 825 | CG | LYS | 106 | 149.806 | 11.766 | 5.349 | 1.00 | 30.00 |
| 826 | CD | LYS | 106 | 149.527 | 12.280 | 6.752 | 1.00 | 30.00 |
| 827 | CE | LYS | 106 | 150.428 | 13.461 | 7.092 | 1.00 | 30.00 |
| 828 | NZ | LYS | 106 | 150.255 | 13.953 | 8.489 | 1.00 | 30.00 |
| 829 | C | LYS | 106 | 147.724 | 13.993 | 2.903 | 1.00 | 30.00 |
| 830 | O | LYS | 106 | 147.709 | 15.194 | 3.184 | 1.00 | 30.00 |
| 831 | N | ILE | 107 | 147.529 | 13.531 | 1.669 | 1.00 | 30.00 |
| 832 | CA | ILE | 107 | 147.265 | 14.412 | 0.534 | 1.00 | 30.00 |
| 833 | CB | ILE | 107 | 147.880 | 13.835 | -0.774 | 1.00 | 30.00 |
| 834 | CG2 | ILE | 107 | 147.514 | 14.704 | -1.977 | 1.00 | 30.00 |
| 835 | CG1 | ILE | 107 | 149.405 | 13.750 | -0.628 | 1.00 | 30.00 |
| 836 | CD1 | ILE | 107 | 150.139 | 13.581 | -1.936 | 1.00 | 30.00 |
| 837 | C | ILE | 107 | 145.750 | 14.577 | 0.354 | 1.00 | 30.00 |
| 838 | O | ILE | 107 | 145.284 | 15.607 | -0.133 | 1.00 | 30.00 |
| 839 | N | SER | 108 | 144.990 | 13.559 | 0.758 | 1.00 | 30.00 |
| 840 | CA | SER | 108 | 143.530 | 13.577 | 0.645 | 1.00 | 30.00 |
| 841 | CB | SER | 108 | 143.063 | 12.475 | -0.317 | 1.00 | 30.00 |
| 842 | OG | SER | 108 | 141.732 | 12.684 | -0.743 | 1.00 | 30.00 |
| 843 | C | SER | 108 | 142.862 | 13.399 | 2.018 | 1.00 | 30.00 |
| 844 | O | SER | 108 | 143.147 | 12.449 | 2.769 | 1.00 | 30.00 |
| 845 | N | LYS | 109 | 141.970 | 14.323 | 2.349 | 1.00 | 30.00 |
| 846 | CA | LYS | 109 | 141.291 | 14.249 | 3.627 | 1.00 | 30.00 |
| 847 | CB | LYS | 109 | 140.540 | 15.555 | 3.922 | 1.00 | 30.00 |
| 848 | CG | LYS | 109 | 139.216 | 15.723 | 3.198 | 1.00 | 30.00 |
| 849 | CD | LYS | 109 | 138.382 | 16.794 | 3.885 | 1.00 | 30.00 |
| 850 | CE | LYS | 109 | 136.960 | 16.860 | 3.347 | 1.00 | 30.00 |
| 851 | NZ | LYS | 109 | 136.185 | 17.956 | 4.005 | 1.00 | 30.00 |
| 852 | C | LYS | 109 | 140.328 | 13.066 | 3.648 | 1.00 | 30.00 |
| 853 | O | LYS | 109 | 140.230 | 12.359 | 4.653 | 1.00 | 30.00 |
| 854 | N | ARG | 110 | 139.632 | 12.834 | 2.538 | 1.00 | 30.00 |
| 855 | CA | ARG | 110 | 138.683 | 11.729 | 2.497 | 1.00 | 30.00 |
| 856 | CB | ARG | 110 | 137.707 | 11.875 | 1.322 | 1.00 | 30.00 |
| 857 | CG | ARG | 110 | 138.249 | 11.610 | -0.070 | 1.00 | 30.00 |
| 858 | CD | ARG | 110 | 137.103 | 11.764 | -1.078 | 1.00 | 30.00 |
| 859 | NE | ARG | 110 | 137.556 | 11.734 | -2.468 | 1.00 | 30.00 |
| 860 | CZ | ARG | 110 | 136.751 | 11.567 | -3.516 | 1.00 | 30.00 |
| 861 | NH1 | ARG | 110 | 135.437 | 11.411 | -3.338 | 1.00 | 30.00 |
| 862 | NH2 | ARG | 110 | 137.264 | 11.551 | -4.745 | 1.00 | 30.00 |
| 863 | C | ARG | 110 | 139.346 | 10.359 | 2.455 | 1.00 | 30.00 |
| 864 | O | ARG | 110 | 138.750 | 9.364 | 2.869 | 1.00 | 30.00 |
| 865 | N | TRP | 111 | 140.579 | 10.303 | 1.969 | 1.00 | 30.00 |
| 866 | CA | TRP | 111 | 141.285 | 9.034 | 1.910 | 1.00 | 30.00 |
| 867 | CB | TRP | 111 | 142.356 | 9.072 | 0.823 | 1.00 | 30.00 |

31

| 868 | CG | TRP | 111 | 143.066 | 7.764 | 0.631 | 1.00 | 30.00 |
| 869 | CD2 | TRP | 111 | 142.801 | 6.788 | -0.387 | 1.00 | 30.00 |
| 870 | CE2 | TRP | 111 | 143.730 | 5.742 | -0.208 | 1.00 | 30.00 |
| 871 | CE3 | TRP | 111 | 141.870 | 6.699 | -1.434 | 1.00 | 30.00 |
| 872 | CD1 | TRP | 111 | 144.105 | 7.281 | 1.367 | 1.00 | 30.00 |
| 873 | NE1 | TRP | 111 | 144.511 | 6.070 | 0.869 | 1.00 | 30.00 |
| 874 | CZ2 | TRP | 111 | 143.761 | 4.612 | -1.045 | 1.00 | 30.00 |
| 875 | CZ3 | TRP | 111 | 141.898 | 5.576 | -2.268 | 1.00 | 30.00 |
| 876 | CH2 | TRP | 111 | 142.840 | 4.549 | -2.065 | 1.00 | 30.00 |
| 877 | C | TRP | 111 | 141.925 | 8.703 | 3.253 | 1.00 | 30.00 |
| 878 | O | TRP | 111 | 142.803 | 9.418 | 3.715 | 1.00 | 30.00 |
| 879 | N | ASN | 112 | 141.460 | 7.624 | 3.872 | 1.00 | 30.00 |
| 880 | CA | ASN | 112 | 141.975 | 7.173 | 5.156 | 1.00 | 30.00 |
| 881 | CB | ASN | 112 | 140.856 | 7.073 | 6.189 | 1.00 | 30.00 |
| 882 | CG | ASN | 112 | 140.337 | 8.419 | 6.613 | 1.00 | 30.00 |
| 883 | OD1 | ASN | 112 | 139.866 | 9.203 | 5.789 | 1.00 | 30.00 |
| 884 | ND2 | ASN | 112 | 140.415 | 8.697 | 7.910 | 1.00 | 30.00 |
| 885 | C | ASN | 112 | 142.613 | 5.804 | 5.001 | 1.00 | 30.00 |
| 886 | O | ASN | 112 | 141.952 | 4.843 | 4.607 | 1.00 | 30.00 |
| 887 | N | PHE | 113 | 143.896 | 5.720 | 5.329 | 1.00 | 30.00 |
| 888 | CA | PHE | 113 | 144.636 | 4.474 | 5.218 | 1.00 | 30.00 |
| 889 | CB | PHE | 113 | 145.008 | 4.224 | 3.749 | 1.00 | 30.00 |
| 890 | CG | PHE | 113 | 145.328 | 2.791 | 3.435 | 1.00 | 30.00 |
| 891 | CD1 | PHE | 113 | 145.511 | 2.387 | 2.117 | 1.00 | 30.00 |
| 892 | CD2 | PHE | 113 | 145.454 | 1.842 | 4.454 | 1.00 | 30.00 |
| 893 | CE1 | PHE | 113 | 145.817 | 1.065 | 1.816 | 1.00 | 30.00 |
| 894 | CE2 | PHE | 113 | 145.759 | 0.513 | 4.164 | 1.00 | 30.00 |
| 895 | CZ | PHE | 113 | 145.941 | 0.125 | 2.845 | 1.00 | 30.00 |
| 896 | C | PHE | 113 | 145.882 | 4.643 | 6.072 | 1.00 | 30.00 |
| 897 | O | PHE | 113 | 146.976 | 4.869 | 5.562 | 1.00 | 30.00 |
| 898 | N | PRO | 114 | 145.721 | 4.531 | 7.395 | 1.00 | 30.00 |
| 899 | CD | PRO | 114 | 144.460 | 4.073 | 8.009 | 1.00 | 30.00 |
| 900 | CA | PRO | 114 | 146.775 | 4.666 | 8.409 | 1.00 | 30.00 |
| 901 | CB | PRO | 114 | 145.973 | 4.678 | 9.710 | 1.00 | 30.00 |
| 902 | CG | PRO | 114 | 144.889 | 3.691 | 9.413 | 1.00 | 30.00 |
| 903 | C | PRO | 114 | 147.861 | 3.574 | 8.395 | 1.00 | 30.00 |
| 904 | O | PRO | 114 | 149.051 | 3.861 | 8.483 | 1.00 | 30.00 |
| 905 | N | SER | 115 | 147.431 | 2.323 | 8.282 | 1.00 | 30.00 |
| 906 | CA | SER | 115 | 148.331 | 1.181 | 8.268 | 1.00 | 30.00 |
| 907 | CB | SER | 115 | 148.440 | 0.613 | 9.687 | 1.00 | 30.00 |
| 908 | OG | SER | 115 | 148.930 | -0.721 | 9.690 | 1.00 | 30.00 |
| 909 | C | SER | 115 | 147.760 | 0.121 | 7.315 | 1.00 | 30.00 |
| 910 | O | SER | 115 | 146.628 | 0.241 | 6.854 | 1.00 | 30.00 |
| 911 | N | PRO | 116 | 148.549 | -0.909 | 6.970 | 1.00 | 30.00 |
| 912 | CD | PRO | 116 | 150.010 | -1.038 | 7.129 | 1.00 | 30.00 |
| 913 | CA | PRO | 116 | 148.029 | -1.947 | 6.070 | 1.00 | 30.00 |
| 914 | CB | PRO | 116 | 149.204 | -2.914 | 5.959 | 1.00 | 30.00 |
| 915 | CG | PRO | 116 | 150.382 | -1.978 | 6.006 | 1.00 | 30.00 |
| 916 | C | PRO | 116 | 146.793 | -2.594 | 6.722 | 1.00 | 30.00 |
| 917 | O | PRO | 116 | 145.847 | -3.022 | 6.048 | 1.00 | 30.00 |
| 918 | N | TYR | 117 | 146.842 | -2.666 | 8.049 | 1.00 | 30.00 |
| 919 | CA | TYR | 117 | 145.754 | -3.201 | 8.840 | 1.00 | 30.00 |

| 920 | CB | TYR | 117 | 146.018 | -4.655 | 9.252 | 1.00 | 30.00 |
| --- | --- | --- | --- | --- | --- | --- | --- | --- |
| 921 | CG | TYR | 117 | 147.243 | -4.907 | 10.106 | 1.00 | 30.00 |
| 922 | CD1 | TYR | 117 | 148.462 | -5.277 | 9.531 | 1.00 | 30.00 |
| 923 | CE1 | TYR | 117 | 149.570 | -5.591 | 10.322 | 1.00 | 30.00 |
| 924 | CD2 | TYR | 117 | 147.169 | -4.845 | 11.495 | 1.00 | 30.00 |
| 925 | CE2 | TYR | 117 | 148.273 | -5.154 | 12.294 | 1.00 | 30.00 |
| 926 | CZ | TYR | 117 | 149.467 | -5.531 | 11.700 | 1.00 | 30.00 |
| 927 | OH | TYR | 117 | 150.544 | -5.874 | 12.491 | 1.00 | 30.00 |
| 928 | C | TYR | 117 | 145.641 | -2.299 | 10.064 | 1.00 | 30.00 |
| 929 | O | TYR | 117 | 146.654 | -1.871 | 10.615 | 1.00 | 30.00 |
| 930 | N | TYR | 118 | 144.409 | -2.004 | 10.476 | 1.00 | 30.00 |
| 931 | CA | TYR | 118 | 144.170 | -1.119 | 11.606 | 1.00 | 30.00 |
| 932 | CB | TYR | 118 | 144.304 | 0.336 | 11.140 | 1.00 | 30.00 |
| 933 | CG | TYR | 118 | 143.507 | 0.660 | 9.885 | 1.00 | 30.00 |
| 934 | CD1 | TYR | 118 | 142.230 | 1.228 | 9.965 | 1.00 | 30.00 |
| 935 | CE1 | TYR | 118 | 141.498 | 1.538 | 8.804 | 1.00 | 30.00 |
| 936 | CD2 | TYR | 118 | 144.031 | 0.404 | 8.612 | 1.00 | 30.00 |
| 937 | CE2 | TYR | 118 | 143.308 | 0.705 | 7.444 | 1.00 | 30.00 |
| 938 | CZ | TYR | 118 | 142.046 | 1.272 | 7.550 | 1.00 | 30.00 |
| 939 | OH | TYR | 118 | 141.331 | 1.562 | 6.407 | 1.00 | 30.00 |
| 940 | C | TYR | 118 | 142.799 | -1.334 | 12.230 | 1.00 | 30.00 |
| 941 | O | TYR | 118 | 142.000 | -2.127 | 11.744 | 1.00 | 30.00 |
| 942 | N | ARG | 119 | 142.540 | -0.617 | 13.317 | 1.00 | 30.00 |
| 943 | CA | ARG | 119 | 141.262 | -0.710 | 14.006 | 1.00 | 30.00 |
| 944 | CB | ARG | 119 | 141.468 | -1.001 | 15.488 | 1.00 | 30.00 |
| 945 | CG | ARG | 119 | 140.175 | -1.135 | 16.268 | 1.00 | 30.00 |
| 946 | CD | ARG | 119 | 140.457 | -1.034 | 17.732 | 1.00 | 30.00 |
| 947 | NE | ARG | 119 | 140.980 | 0.294 | 18.031 | 1.00 | 30.00 |
| 948 | CZ | ARG | 119 | 141.572 | 0.635 | 19.172 | 1.00 | 30.00 |
| 949 | NH1 | ARG | 119 | 141.726 | -0.259 | 20.143 | 1.00 | 30.00 |
| 950 | NH2 | ARG | 119 | 142.006 | 1.878 | 19.345 | 1.00 | 30.00 |
| 951 | C | ARG | 119 | 140.489 | 0.592 | 13.870 | 1.00 | 30.00 |
| 952 | O | ARG | 119 | 141.047 | 1.674 | 14.042 | 1.00 | 30.00 |
| 953 | N | LEU | 120 | 139.206 | 0.471 | 13.547 | 1.00 | 30.00 |
| 954 | CA | LEU | 120 | 138.313 | 1.612 | 13.409 | 1.00 | 30.00 |
| 955 | CB | LEU | 120 | 137.605 | 1.573 | 12.055 | 1.00 | 30.00 |
| 956 | CG | LEU | 120 | 138.452 | 1.765 | 10.798 | 1.00 | 30.00 |
| 957 | CD1 | LEU | 120 | 137.593 | 1.526 | 9.561 | 1.00 | 30.00 |
| 958 | CD2 | LEU | 120 | 139.034 | 3.170 | 10.783 | 1.00 | 30.00 |
| 959 | C | LEU | 120 | 137.295 | 1.459 | 14.533 | 1.00 | 30.00 |
| 960 | O | LEU | 120 | 137.020 | 0.344 | 14.981 | 1.00 | 30.00 |
| 961 | N | ARG | 121 | 136.737 | 2.568 | 15.000 | 1.00 | 30.00 |
| 962 | CA | ARG | 121 | 135.763 | 2.499 | 16.083 | 1.00 | 30.00 |
| 963 | CB | ARG | 121 | 136.466 | 2.703 | 17.421 | 1.00 | 30.00 |
| 964 | CG | ARG | 121 | 135.738 | 2.092 | 18.586 | 1.00 | 30.00 |
| 965 | CD | ARG | 121 | 136.687 | 1.209 | 19.387 | 1.00 | 30.00 |
| 966 | NE | ARG | 121 | 137.782 | 1.981 | 19.971 | 1.00 | 30.00 |
| 967 | CZ | ARG | 121 | 138.679 | 1.491 | 20.822 | 1.00 | 30.00 |
| 968 | NH1 | ARG | 121 | 138.619 | 0.219 | 21.195 | 1.00 | 30.00 |
| 969 | NH2 | ARG | 121 | 139.627 | 2.281 | 21.313 | 1.00 | 30.00 |
| 970 | C | ARG | 121 | 134.656 | 3.529 | 15.921 | 1.00 | 30.00 |
| 971 | O | ARG | 121 | 134.885 | 4.725 | 16.057 | 1.00 | 30.00 |

| 972 | N | PHE | 122 | 133.450 | 3.059 | 15.634 | 1.00 | 30.00 |
| --- | --- | --- | --- | --- | --- | --- | --- | --- |
| 973 | CA | PHE | 122 | 132.329 | 3.963 | 15.451 | 1.00 | 30.00 |
| 974 | CB | PHE | 122 | 131.702 | 3.732 | 14.080 | 1.00 | 30.00 |
| 975 | CG | PHE | 122 | 132.685 | 3.823 | 12.944 | 1.00 | 30.00 |
| 976 | CD1 | PHE | 122 | 133.584 | 2.788 | 12.701 | 1.00 | 30.00 |
| 977 | CD2 | PHE | 122 | 132.720 | 4.943 | 12.122 | 1.00 | 30.00 |
| 978 | CE1 | PHE | 122 | 134.507 | 2.867 | 11.654 | 1.00 | 30.00 |
| 979 | CE2 | PHE | 122 | 133.634 | 5.031 | 11.080 | 1.00 | 30.00 |
| 980 | CZ | PHE | 122 | 134.533 | 3.988 | 10.844 | 1.00 | 30.00 |
| 981 | C | PHE | 122 | 131.273 | 3.833 | 16.546 | 1.00 | 30.00 |
| 982 | O | PHE | 122 | 131.424 | 3.055 | 17.493 | 1.00 | 30.00 |
| 983 | N | LYS | 123 | 130.207 | 4.611 | 16.417 | 1.00 | 30.00 |
| 984 | CA | LYS | 123 | 129.136 | 4.591 | 17.405 | 1.00 | 30.00 |
| 985 | CB | LYS | 123 | 129.472 | 5.572 | 18.536 | 1.00 | 30.00 |
| 986 | CG | LYS | 123 | 128.711 | 5.337 | 19.826 | 1.00 | 30.00 |
| 987 | CD | LYS | 123 | 129.333 | 6.120 | 20.972 | 1.00 | 30.00 |
| 988 | CE | LYS | 123 | 128.661 | 5.791 | 22.298 | 1.00 | 30.00 |
| 989 | NZ | LYS | 123 | 129.244 | 6.563 | 23.431 | 1.00 | 30.00 |
| 990 | C | LYS | 123 | 127.795 | 4.956 | 16.766 | 1.00 | 30.00 |
| 991 | O | LYS | 123 | 127.704 | 5.901 | 15.974 | 1.00 | 30.00 |
| 992 | N | VAL | 124 | 126.759 | 4.194 | 17.097 | 1.00 | 30.00 |
| 993 | CA | VAL | 124 | 125.437 | 4.466 | 16.553 | 1.00 | 30.00 |
| 994 | CB | VAL | 124 | 124.458 | 3.293 | 16.797 | 1.00 | 30.00 |
| 995 | CG1 | VAL | 124 | 125.115 | 1.972 | 16.420 | 1.00 | 30.00 |
| 996 | CG2 | VAL | 124 | 123.994 | 3.292 | 18.248 | 1.00 | 30.00 |
| 997 | C | VAL | 124 | 124.884 | 5.699 | 17.259 | 1.00 | 30.00 |
| 998 | O | VAL | 124 | 125.146 | 5.911 | 18.443 | 1.00 | 30.00 |
| 999 | N | PRO | 125 | 124.115 | 6.532 | 16.540 | 1.00 | 30.00 |
| 1000 | CD | PRO | 125 | 123.875 | 6.496 | 15.086 | 1.00 | 30.00 |
| 1001 | CA | PRO | 125 | 123.531 | 7.741 | 17.129 | 1.00 | 30.00 |
| 1002 | CB | PRO | 125 | 122.673 | 8.286 | 15.994 | 1.00 | 30.00 |
| 1003 | CG | PRO | 125 | 123.479 | 7.926 | 14.791 | 1.00 | 30.00 |
| 1004 | C | PRO | 125 | 122.718 | 7.432 | 18.390 | 1.00 | 30.00 |
| 1005 | O | PRO | 125 | 122.264 | 8.338 | 19.087 | 1.00 | 30.00 |
| 1006 | N | ARG | 126 | 122.533 | 6.144 | 18.668 | 1.00 | 30.00 |
| 1007 | CA | ARG | 126 | 121.801 | 5.709 | 19.852 | 1.00 | 30.00 |
| 1008 | CB | ARG | 126 | 120.879 | 4.538 | 19.506 | 1.00 | 30.00 |
| 1009 | CG | ARG | 126 | 119.774 | 4.904 | 18.519 | 1.00 | 30.00 |
| 1010 | CD | ARG | 126 | 118.975 | 6.121 | 18.995 | 1.00 | 30.00 |
| 1011 | NE | ARG | 126 | 117.931 | 6.510 | 18.047 | 1.00 | 30.00 |
| 1012 | CZ | ARG | 126 | 117.122 | 7.556 | 18.202 | 1.00 | 30.00 |
| 1013 | NH1 | ARG | 126 | 117.229 | 8.331 | 19.273 | 1.00 | 30.00 |
| 1014 | NH2 | ARG | 126 | 116.202 | 7.828 | 17.285 | 1.00 | 30.00 |
| 1015 | C | ARG | 126 | 122.806 | 5.316 | 20.931 | 1.00 | 30.00 |
| 1016 | O | ARG | 126 | 122.684 | 4.282 | 21.594 | 1.00 | 30.00 |
| 1017 | N | SER | 127 | 123.809 | 6.178 | 21.069 | 1.00 | 30.00 |
| 1018 | CA | SER | 127 | 124.896 | 6.051 | 22.032 | 1.00 | 30.00 |
| 1019 | CB | SER | 127 | 124.500 | 6.722 | 23.351 | 1.00 | 30.00 |
| 1020 | OG | SER | 127 | 124.435 | 8.132 | 23.202 | 1.00 | 30.00 |
| 1021 | C | SER | 127 | 125.432 | 4.654 | 22.310 | 1.00 | 30.00 |
| 1022 | O | SER | 127 | 126.070 | 4.048 | 21.450 | 1.00 | 30.00 |
| 1023 | N | ASN | 128 | 125.183 | 4.166 | 23.524 | 1.00 | 30.00 |

| 1024 | CA | ASN | 128 | 125.649 | 2.857 | 23.981 | 1.00 | 30.00 |
| 1025 | CB | ASN | 128 | 124.559 | 2.186 | 24.825 | 1.00 | 30.00 |
| 1026 | CG | ASN | 128 | 124.387 | 2.847 | 26.179 | 1.00 | 30.00 |
| 1027 | OD1 | ASN | 128 | 125.329 | 2.918 | 26.968 | 1.00 | 30.00 |
| 1028 | ND2 | ASN | 128 | 123.183 | 3.336 | 26.456 | 1.00 | 30.00 |
| 1029 | C | ASN | 128 | 126.136 | 1.892 | 22.899 | 1.00 | 30.00 |
| 1030 | O | ASN | 128 | 127.219 | 1.314 | 23.023 | 1.00 | 30.00 |
| 1031 | N | ILE | 129 | 125.340 | 1.724 | 21.845 | 1.00 | 30.00 |
| 1032 | CA | ILE | 129 | 125.688 | 0.826 | 20.746 | 1.00 | 30.00 |
| 1033 | CB | ILE | 129 | 124.501 | 0.636 | 19.775 | 1.00 | 30.00 |
| 1034 | CG2 | ILE | 129 | 124.925 | -0.232 | 18.597 | 1.00 | 30.00 |
| 1035 | CG1 | ILE | 129 | 123.324 | -0.006 | 20.508 | 1.00 | 30.00 |
| 1036 | CD1 | ILE | 129 | 123.604 | -1.409 | 20.973 | 1.00 | 30.00 |
| 1037 | C | ILE | 129 | 126.893 | 1.304 | 19.943 | 1.00 | 30.00 |
| 1038 | O | ILE | 129 | 126.793 | 2.203 | 19.104 | 1.00 | 30.00 |
| 1039 | N | THR | 130 | 128.032 | 0.677 | 20.207 | 1.00 | 30.00 |
| 1040 | CA | THR | 130 | 129.276 | 1.010 | 19.529 | 1.00 | 30.00 |
| 1041 | CB | THR | 130 | 130.382 | 1.330 | 20.539 | 1.00 | 30.00 |
| 1042 | OG1 | THR | 130 | 130.510 | 0.234 | 21.457 | 1.00 | 30.00 |
| 1043 | CG2 | THR | 130 | 130.049 | 2.608 | 21.302 | 1.00 | 30.00 |
| 1044 | C | THR | 130 | 129.729 | -0.161 | 18.674 | 1.00 | 30.00 |
| 1045 | O | THR | 130 | 129.494 | -1.325 | 19.002 | 1.00 | 30.00 |
| 1046 | N | VAL | 131 | 130.391 | 0.164 | 17.576 | 1.00 | 30.00 |
| 1047 | CA | VAL | 131 | 130.872 | -0.847 | 16.659 | 1.00 | 30.00 |
| 1048 | CB | VAL | 131 | 130.187 | -0.676 | 15.290 | 1.00 | 30.00 |
| 1049 | CG1 | VAL | 131 | 130.693 | -1.707 | 14.297 | 1.00 | 30.00 |
| 1050 | CG2 | VAL | 131 | 128.683 | -0.800 | 15.471 | 1.00 | 30.00 |
| 1051 | C | VAL | 131 | 132.381 | -0.746 | 16.493 | 1.00 | 30.00 |
| 1052 | O | VAL | 131 | 132.948 | 0.346 | 16.541 | 1.00 | 30.00 |
| 1053 | N | ALA | 132 | 133.026 | -1.899 | 16.333 | 1.00 | 30.00 |
| 1054 | CA | ALA | 132 | 134.464 | -1.954 | 16.108 | 1.00 | 30.00 |
| 1055 | CB | ALA | 132 | 135.151 | -2.783 | 17.178 | 1.00 | 30.00 |
| 1056 | C | ALA | 132 | 134.666 | -2.597 | 14.737 | 1.00 | 30.00 |
| 1057 | O | ALA | 132 | 134.010 | -3.579 | 14.394 | 1.00 | 30.00 |
| 1058 | N | ILE | 133 | 135.564 | -2.016 | 13.953 | 1.00 | 30.00 |
| 1059 | CA | ILE | 133 | 135.868 | -2.527 | 12.623 | 1.00 | 30.00 |
| 1060 | CB | ILE | 133 | 135.497 | -1.478 | 11.539 | 1.00 | 30.00 |
| 1061 | CG2 | ILE | 133 | 136.177 | -1.802 | 10.215 | 1.00 | 30.00 |
| 1062 | CG1 | ILE | 133 | 133.982 | -1.436 | 11.367 | 1.00 | 30.00 |
| 1063 | CD1 | ILE | 133 | 133.536 | -0.665 | 10.150 | 1.00 | 30.00 |
| 1064 | C | ILE | 133 | 137.363 | -2.841 | 12.553 | 1.00 | 30.00 |
| 1065 | O | ILE | 133 | 138.183 | -1.989 | 12.872 | 1.00 | 30.00 |
| 1066 | N | PHE | 134 | 137.714 | -4.067 | 12.163 | 1.00 | 30.00 |
| 1067 | CA | PHE | 134 | 139.120 | -4.454 | 12.048 | 1.00 | 30.00 |
| 1068 | CB | PHE | 134 | 139.410 | -5.732 | 12.833 | 1.00 | 30.00 |
| 1069 | CG | PHE | 134 | 139.255 | -5.568 | 14.305 | 1.00 | 30.00 |
| 1070 | CD1 | PHE | 134 | 137.998 | -5.573 | 14.887 | 1.00 | 30.00 |
| 1071 | CD2 | PHE | 134 | 140.364 | -5.332 | 15.110 | 1.00 | 30.00 |
| 1072 | CE1 | PHE | 134 | 137.846 | -5.340 | 16.251 | 1.00 | 30.00 |
| 1073 | CE2 | PHE | 134 | 140.221 | -5.099 | 16.475 | 1.00 | 30.00 |
| 1074 | CZ | PHE | 134 | 138.961 | -5.101 | 17.045 | 1.00 | 30.00 |
| 1075 | C | PHE | 134 | 139.514 | -4.650 | 10.599 | 1.00 | 30.00 |

| | | | | | | | |
|---|---|---|---|---|---|---|---|
| 1076 | O | PHE | 134 | 139.167 | -5.654 | 9.980 | 1.00 | 30.00 |
| 1077 | N | MET | 135 | 140.224 | -3.665 | 10.056 | 1.00 | 30.00 |
| 1078 | CA | MET | 135 | 140.696 | -3.709 | 8.675 | 1.00 | 30.00 |
| 1079 | CB | MET | 135 | 140.889 | -2.287 | 8.159 | 1.00 | 30.00 |
| 1080 | CG | MET | 135 | 139.627 | -1.444 | 8.213 | 1.00 | 30.00 |
| 1081 | SD | MET | 135 | 138.439 | -1.872 | 6.926 | 1.00 | 30.00 |
| 1082 | CE | MET | 135 | 139.022 | -0.825 | 5.555 | 1.00 | 30.00 |
| 1083 | C | MET | 135 | 142.027 | -4.471 | 8.650 | 1.00 | 30.00 |
| 1084 | O | MET | 135 | 142.995 | -4.065 | 9.287 | 1.00 | 30.00 |
| 1085 | N | LEU | 136 | 142.079 | -5.573 | 7.919 | 1.00 | 30.00 |
| 1086 | CA | LEU | 136 | 143.298 | -6.368 | 7.877 | 1.00 | 30.00 |
| 1087 | CB | LEU | 136 | 143.001 | -7.818 | 8.307 | 1.00 | 30.00 |
| 1088 | CG | LEU | 136 | 141.989 | -7.959 | 9.452 | 1.00 | 30.00 |
| 1089 | CD1 | LEU | 136 | 141.623 | -9.421 | 9.660 | 1.00 | 30.00 |
| 1090 | CD2 | LEU | 136 | 142.550 | -7.330 | 10.730 | 1.00 | 30.00 |
| 1091 | C | LEU | 136 | 143.939 | -6.387 | 6.499 | 1.00 | 30.00 |
| 1092 | O | LEU | 136 | 143.332 | -5.980 | 5.492 | 1.00 | 30.00 |
| 1093 | N | ASP | 137 | 145.182 | -6.851 | 6.463 | 1.00 | 30.00 |
| 1094 | CA | ASP | 137 | 145.881 | -6.977 | 5.205 | 1.00 | 30.00 |
| 1095 | CB | ASP | 137 | 147.260 | -6.338 | 5.270 | 1.00 | 30.00 |
| 1096 | CG | ASP | 137 | 147.820 | -6.069 | 3.894 | 1.00 | 30.00 |
| 1097 | OD1 | ASP | 137 | 147.747 | -6.982 | 3.036 | 1.00 | 30.00 |
| 1098 | OD2 | ASP | 137 | 148.322 | -4.947 | 3.667 | 1.00 | 30.00 |
| 1099 | C | ASP | 137 | 146.015 | -8.473 | 4.944 | 1.00 | 30.00 |
| 1100 | O | ASP | 137 | 146.809 | -9.160 | 5.591 | 1.00 | 30.00 |
| 1101 | N | THR | 138 | 145.226 | -8.977 | 4.002 | 1.00 | 30.00 |
| 1102 | CA | THR | 138 | 145.249 | -10.397 | 3.696 | 1.00 | 30.00 |
| 1103 | CB | THR | 138 | 144.009 | -10.830 | 2.887 | 1.00 | 30.00 |
| 1104 | OG1 | THR | 138 | 143.894 | -10.031 | 1.702 | 1.00 | 30.00 |
| 1105 | CG2 | THR | 138 | 142.760 | -10.683 | 3.736 | 1.00 | 30.00 |
| 1106 | C | THR | 138 | 146.498 | -10.868 | 2.980 | 1.00 | 30.00 |
| 1107 | O | THR | 138 | 146.954 | -11.978 | 3.227 | 1.00 | 30.00 |
| 1108 | N | VAL | 139 | 147.062 | -10.058 | 2.094 | 1.00 | 30.00 |
| 1109 | CA | VAL | 139 | 148.279 | -10.499 | 1.429 | 1.00 | 30.00 |
| 1110 | CB | VAL | 139 | 148.784 | -9.492 | 0.380 | 1.00 | 30.00 |
| 1111 | CG1 | VAL | 139 | 150.121 | -9.965 | -0.186 | 1.00 | 30.00 |
| 1112 | CG2 | VAL | 139 | 147.768 | -9.377 | -0.755 | 1.00 | 30.00 |
| 1113 | C | VAL | 139 | 149.359 | -10.712 | 2.482 | 1.00 | 30.00 |
| 1114 | O | VAL | 139 | 150.130 | -11.664 | 2.407 | 1.00 | 30.00 |
| 1115 | N | MET | 140 | 149.390 | -9.840 | 3.481 | 1.00 | 30.00 |
| 1116 | CA | MET | 140 | 150.366 | -9.939 | 4.561 | 1.00 | 30.00 |
| 1117 | CB | MET | 140 | 150.468 | -8.597 | 5.293 | 1.00 | 30.00 |
| 1118 | CG | MET | 140 | 151.215 | -7.541 | 4.502 | 1.00 | 30.00 |
| 1119 | SD | MET | 140 | 151.164 | -5.935 | 5.275 | 1.00 | 30.00 |
| 1120 | CE | MET | 140 | 151.439 | -6.397 | 7.016 | 1.00 | 30.00 |
| 1121 | C | MET | 140 | 150.033 | -11.036 | 5.569 | 1.00 | 30.00 |
| 1122 | O | MET | 140 | 150.894 | -11.496 | 6.307 | 1.00 | 30.00 |
| 1123 | N | LEU | 141 | 148.778 | -11.456 | 5.588 | 1.00 | 30.00 |
| 1124 | CA | LEU | 141 | 148.316 | -12.472 | 6.524 | 1.00 | 30.00 |
| 1125 | CB | LEU | 141 | 146.886 | -12.105 | 6.954 | 1.00 | 30.00 |
| 1126 | CG | LEU | 141 | 146.176 | -12.765 | 8.137 | 1.00 | 30.00 |
| 1127 | CD1 | LEU | 141 | 146.868 | -12.424 | 9.458 | 1.00 | 30.00 |

| 1128 | CD2 | LEU | 141 | 144.740 | -12.263 | 8.149 | 1.00 | 30.00 |
|---|---|---|---|---|---|---|---|---|
| 1129 | C | LEU | 141 | 148.368 | -13.884 | 5.916 | 1.00 | 30.00 |
| 1130 | O | LEU | 141 | 148.443 | -14.875 | 6.642 | 1.00 | 30.00 |
| 1131 | N | CYS | 142 | 148.344 | -13.951 | 4.583 | 1.00 | 30.00 |
| 1132 | CA | CYS | 142 | 148.367 | -15.201 | 3.810 | 1.00 | 30.00 |
| 1133 | C | CYS | 142 | 149.481 | -15.288 | 2.786 | 1.00 | 30.00 |
| 1134 | O | CYS | 142 | 150.648 | -15.013 | 3.057 | 1.00 | 30.00 |
| 1135 | CB | CYS | 142 | 147.108 | -15.349 | 2.979 | 1.00 | 30.00 |
| 1136 | SG | CYS | 142 | 145.611 | -16.016 | 3.725 | 1.00 | 30.00 |
| 1137 | N | GLY | 143 | 149.038 | -15.670 | 1.583 | 1.00 | 30.00 |
| 1138 | CA | GLY | 143 | 149.888 | -15.834 | 0.417 | 1.00 | 30.00 |
| 1139 | C | GLY | 143 | 149.213 | -16.549 | -0.763 | 1.00 | 30.00 |
| 1140 | O | GLY | 143 | 149.620 | -16.338 | -1.911 | 1.00 | 30.00 |
| 1141 | N | ASN | 144 | 148.193 | -17.381 | -0.503 | 1.00 | 30.00 |
| 1142 | CA | ASN | 144 | 147.492 | -18.130 | -1.569 | 1.00 | 30.00 |
| 1143 | CB | ASN | 144 | 146.363 | -19.013 | -0.981 | 1.00 | 30.00 |
| 1144 | CG | ASN | 144 | 146.884 | -20.227 | -0.197 | 1.00 | 30.00 |
| 1145 | OD1 | ASN | 144 | 147.637 | -21.050 | -0.718 | 1.00 | 30.00 |
| 1146 | ND2 | ASN | 144 | 146.464 | -20.343 | 1.057 | 1.00 | 30.00 |
| 1147 | C | ASN | 144 | 146.910 | -17.218 | -2.667 | 1.00 | 30.00 |
| 1148 | O | ASN | 144 | 146.643 | -16.041 | -2.426 | 1.00 | 30.00 |
| 1149 | N | SER | 145 | 146.712 | -17.761 | -3.869 | 1.00 | 30.00 |
| 1150 | CA | SER | 145 | 146.177 | -16.960 | -4.976 | 1.00 | 30.00 |
| 1151 | CB | SER | 145 | 147.345 | -16.339 | -5.759 | 1.00 | 30.00 |
| 1152 | OG | SER | 145 | 146.899 | -15.334 | -6.654 | 1.00 | 30.00 |
| 1153 | C | SER | 145 | 145.246 | -17.734 | -5.939 | 1.00 | 30.00 |
| 1154 | O | SER | 145 | 144.050 | -17.377 | -6.037 | 1.00 | 30.00 |
| 1155 | OXT | SER | 145 | 145.714 | -18.691 | -6.591 | 1.00 | 30.00 |
| 1156 | CB | VAL | 161 | 155.920 | -9.913 | 5.983 | 1.00 | 30.00 |
| 1157 | CG1 | VAL | 161 | 156.813 | -9.398 | 7.099 | 1.00 | 30.00 |
| 1158 | CG2 | VAL | 161 | 156.760 | -10.563 | 4.893 | 1.00 | 30.00 |
| 1159 | C | VAL | 161 | 154.015 | -10.255 | 7.593 | 1.00 | 30.00 |
| 1160 | O | VAL | 161 | 154.030 | -9.035 | 7.741 | 1.00 | 30.00 |
| 1161 | N | VAL | 161 | 154.067 | -11.506 | 5.441 | 1.00 | 30.00 |
| 1162 | CA | VAL | 161 | 154.896 | -10.936 | 6.540 | 1.00 | 30.00 |
| 1163 | N | ALA | 162 | 153.244 | -11.057 | 8.319 | 1.00 | 30.00 |
| 1164 | CA | ALA | 162 | 152.365 | -10.531 | 9.352 | 1.00 | 30.00 |
| 1165 | CB | ALA | 162 | 151.153 | -9.866 | 8.716 | 1.00 | 30.00 |
| 1166 | C | ALA | 162 | 151.921 | -11.624 | 10.314 | 1.00 | 30.00 |
| 1167 | O | ALA | 162 | 150.743 | -11.988 | 10.357 | 1.00 | 30.00 |
| 1168 | N | ARG | 163 | 152.872 | -12.160 | 11.074 | 1.00 | 30.00 |
| 1169 | CA | ARG | 163 | 152.565 | -13.191 | 12.058 | 1.00 | 30.00 |
| 1170 | CB | ARG | 163 | 153.774 | -14.095 | 12.318 | 1.00 | 30.00 |
| 1171 | CG | ARG | 163 | 153.478 | -15.235 | 13.292 | 1.00 | 30.00 |
| 1172 | CD | ARG | 163 | 154.713 | -16.080 | 13.593 | 1.00 | 30.00 |
| 1173 | NE | ARG | 163 | 155.217 | -16.783 | 12.416 | 1.00 | 30.00 |
| 1174 | CZ | ARG | 163 | 156.271 | -17.595 | 12.421 | 1.00 | 30.00 |
| 1175 | NH1 | ARG | 163 | 156.940 | -17.813 | 13.544 | 1.00 | 30.00 |
| 1176 | NH2 | ARG | 163 | 156.658 | -18.188 | 11.301 | 1.00 | 30.00 |
| 1177 | C | ARG | 163 | 152.172 | -12.470 | 13.340 | 1.00 | 30.00 |
| 1178 | O | ARG | 163 | 151.643 | -13.078 | 14.272 | 1.00 | 30.00 |
| 1179 | N | THR | 164 | 152.449 | -11.168 | 13.383 | 1.00 | 30.00 |

| 1180 | CA | THR | 164 | 152.083 | -10.353 | 14.533 | 1.00 | 30.00 |
| 1181 | CB | THR | 164 | 153.076 | -9.194 | 14.796 | 1.00 | 30.00 |
| 1182 | OG1 | THR | 164 | 154.409 | -9.704 | 14.885 | 1.00 | 30.00 |
| 1183 | CG2 | THR | 164 | 152.738 | -8.503 | 16.114 | 1.00 | 30.00 |
| 1184 | C | THR | 164 | 150.710 | -9.757 | 14.234 | 1.00 | 30.00 |
| 1185 | O | THR | 164 | 149.990 | -9.379 | 15.156 | 1.00 | 30.00 |
| 1186 | N | GLN | 165 | 150.348 | -9.664 | 12.951 | 1.00 | 30.00 |
| 1187 | CA | GLN | 165 | 149.034 | -9.133 | 12.590 | 1.00 | 30.00 |
| 1188 | CB | GLN | 165 | 148.874 | -8.972 | 11.076 | 1.00 | 30.00 |
| 1189 | CG | GLN | 165 | 147.535 | -8.332 | 10.689 | 1.00 | 30.00 |
| 1190 | CD | GLN | 165 | 147.238 | -8.386 | 9.193 | 1.00 | 30.00 |
| 1191 | OE1 | GLN | 165 | 146.219 | -7.867 | 8.737 | 1.00 | 30.00 |
| 1192 | NE2 | GLN | 165 | 148.124 | -9.015 | 8.425 | 1.00 | 30.00 |
| 1193 | C | GLN | 165 | 148.000 | -10.129 | 13.094 | 1.00 | 30.00 |
| 1194 | O | GLN | 165 | 147.034 | -9.758 | 13.759 | 1.00 | 30.00 |
| 1195 | N | LEU | 166 | 148.212 | -11.403 | 12.778 | 1.00 | 30.00 |
| 1196 | CA | LEU | 166 | 147.303 | -12.446 | 13.223 | 1.00 | 30.00 |
| 1197 | CB | LEU | 166 | 147.717 | -13.796 | 12.647 | 1.00 | 30.00 |
| 1198 | CG | LEU | 166 | 146.711 | -14.911 | 12.938 | 1.00 | 30.00 |
| 1199 | CD1 | LEU | 166 | 145.364 | -14.534 | 12.334 | 1.00 | 30.00 |
| 1200 | CD2 | LEU | 166 | 147.206 | -16.233 | 12.373 | 1.00 | 30.00 |
| 1201 | C | LEU | 166 | 147.317 | -12.509 | 14.751 | 1.00 | 30.00 |
| 1202 | O | LEU | 166 | 146.312 | -12.832 | 15.385 | 1.00 | 30.00 |
| 1203 | N | SER | 167 | 148.465 | -12.191 | 15.341 | 1.00 | 30.00 |
| 1204 | CA | SER | 167 | 148.603 | -12.194 | 16.792 | 1.00 | 30.00 |
| 1205 | CB | SER | 167 | 150.081 | -12.275 | 17.172 | 1.00 | 30.00 |
| 1206 | OG | SER | 167 | 150.227 | -12.619 | 18.537 | 1.00 | 30.00 |
| 1207 | C | SER | 167 | 147.973 | -10.921 | 17.371 | 1.00 | 30.00 |
| 1208 | O | SER | 167 | 147.518 | -10.900 | 18.513 | 1.00 | 30.00 |
| 1209 | N | TRP | 168 | 147.948 | -9.866 | 16.562 | 1.00 | 30.00 |
| 1210 | CA | TRP | 168 | 147.375 | -8.583 | 16.951 | 1.00 | 30.00 |
| 1211 | CB | TRP | 168 | 147.786 | -7.514 | 15.937 | 1.00 | 30.00 |
| 1212 | CG | TRP | 168 | 146.993 | -6.242 | 16.000 | 1.00 | 30.00 |
| 1213 | CD2 | TRP | 168 | 146.012 | -5.802 | 15.056 | 1.00 | 30.00 |
| 1214 | CE2 | TRP | 168 | 145.544 | -4.545 | 15.493 | 1.00 | 30.00 |
| 1215 | CE3 | TRP | 168 | 145.484 | -6.348 | 13.879 | 1.00 | 30.00 |
| 1216 | CD1 | TRP | 168 | 147.074 | -5.264 | 16.953 | 1.00 | 30.00 |
| 1217 | NE1 | TRP | 168 | 146.205 | -4.239 | 16.653 | 1.00 | 30.00 |
| 1218 | CZ2 | TRP | 168 | 144.571 | -3.827 | 14.795 | 1.00 | 30.00 |
| 1219 | CZ3 | TRP | 168 | 144.516 | -5.634 | 13.187 | 1.00 | 30.00 |
| 1220 | CH2 | TRP | 168 | 144.073 | -4.385 | 13.646 | 1.00 | 30.00 |
| 1221 | C | TRP | 168 | 145.851 | -8.683 | 17.004 | 1.00 | 30.00 |
| 1222 | O | TRP | 168 | 145.222 | -8.259 | 17.980 | 1.00 | 30.00 |
| 1223 | N | LEU | 169 | 145.269 | -9.246 | 15.945 | 1.00 | 30.00 |
| 1224 | CA | LEU | 169 | 143.823 | -9.417 | 15.846 | 1.00 | 30.00 |
| 1225 | CB | LEU | 169 | 143.464 | -10.058 | 14.496 | 1.00 | 30.00 |
| 1226 | CG | LEU | 169 | 141.981 | -10.209 | 14.125 | 1.00 | 30.00 |
| 1227 | CD1 | LEU | 169 | 141.283 | -8.859 | 14.127 | 1.00 | 30.00 |
| 1228 | CD2 | LEU | 169 | 141.877 | -10.848 | 12.759 | 1.00 | 30.00 |
| 1229 | C | LEU | 169 | 143.297 | -10.272 | 17.006 | 1.00 | 30.00 |
| 1230 | O | LEU | 169 | 142.182 | -10.054 | 17.491 | 1.00 | 30.00 |
| 1231 | N | LYS | 170 | 144.105 | -11.238 | 17.448 | 1.00 | 30.00 |

38

| 1232 | CA | LYS | 170 | 143.738 | -12.120 | 18.559 | 1.00 | 30.00 |
| 1233 | CB | LYS | 170 | 144.862 | -13.123 | 18.840 | 1.00 | 30.00 |
| 1234 | CG | LYS | 170 | 144.549 | -14.151 | 19.926 | 1.00 | 30.00 |
| 1235 | CD | LYS | 170 | 143.705 | -15.302 | 19.388 | 1.00 | 30.00 |
| 1236 | CE | LYS | 170 | 143.405 | -16.352 | 20.459 | 1.00 | 30.00 |
| 1237 | NZ | LYS | 170 | 144.618 | -17.031 | 20.995 | 1.00 | 30.00 |
| 1238 | C | LYS | 170 | 143.487 | -11.288 | 19.814 | 1.00 | 30.00 |
| 1239 | O | LYS | 170 | 142.379 | -11.284 | 20.353 | 1.00 | 30.00 |
| 1240 | N | LYS | 171 | 144.522 | -10.590 | 20.275 | 1.00 | 30.00 |
| 1241 | CA | LYS | 171 | 144.408 | -9.747 | 21.460 | 1.00 | 30.00 |
| 1242 | CB | LYS | 171 | 145.719 | -8.998 | 21.702 | 1.00 | 30.00 |
| 1243 | CG | LYS | 171 | 145.625 | -7.903 | 22.760 | 1.00 | 30.00 |
| 1244 | CD | LYS | 171 | 146.872 | -7.036 | 22.761 | 1.00 | 30.00 |
| 1245 | CE | LYS | 171 | 147.135 | -6.447 | 21.376 | 1.00 | 30.00 |
| 1246 | NZ | LYS | 171 | 145.987 | -5.650 | 20.855 | 1.00 | 30.00 |
| 1247 | C | LYS | 171 | 143.269 | -8.743 | 21.290 | 1.00 | 30.00 |
| 1248 | O | LYS | 171 | 142.433 | -8.583 | 22.182 | 1.00 | 30.00 |
| 1249 | N | GLN | 172 | 143.254 | -8.071 | 20.140 | 1.00 | 30.00 |
| 1250 | CA | GLN | 172 | 142.228 | -7.085 | 19.811 | 1.00 | 30.00 |
| 1251 | CB | GLN | 172 | 142.339 | -6.694 | 18.341 | 1.00 | 30.00 |
| 1252 | CG | GLN | 172 | 143.457 | -5.756 | 18.012 | 1.00 | 30.00 |
| 1253 | CD | GLN | 172 | 143.233 | -4.391 | 18.595 | 1.00 | 30.00 |
| 1254 | OE1 | GLN | 172 | 143.311 | -4.203 | 19.804 | 1.00 | 30.00 |
| 1255 | NE2 | GLN | 172 | 142.938 | -3.426 | 17.738 | 1.00 | 30.00 |
| 1256 | C | GLN | 172 | 140.814 | -7.605 | 20.051 | 1.00 | 30.00 |
| 1257 | O | GLN | 172 | 140.061 | -7.057 | 20.859 | 1.00 | 30.00 |
| 1258 | N | LEU | 173 | 140.473 | -8.663 | 19.313 | 1.00 | 30.00 |
| 1259 | CA | LEU | 173 | 139.165 | -9.310 | 19.363 | 1.00 | 30.00 |
| 1260 | CB | LEU | 173 | 139.100 | -10.415 | 18.299 | 1.00 | 30.00 |
| 1261 | CG | LEU | 173 | 139.193 | -9.971 | 16.828 | 1.00 | 30.00 |
| 1262 | CD1 | LEU | 173 | 139.318 | -11.183 | 15.928 | 1.00 | 30.00 |
| 1263 | CD2 | LEU | 173 | 137.962 | -9.154 | 16.446 | 1.00 | 30.00 |
| 1264 | C | LEU | 173 | 138.856 | -9.884 | 20.738 | 1.00 | 30.00 |
| 1265 | O | LEU | 173 | 137.697 | -9.930 | 21.164 | 1.00 | 30.00 |
| 1266 | N | ALA | 174 | 139.901 | -10.319 | 21.430 | 1.00 | 30.00 |
| 1267 | CA | ALA | 174 | 139.744 | -10.880 | 22.760 | 1.00 | 30.00 |
| 1268 | CB | ALA | 174 | 140.938 | -11.757 | 23.094 | 1.00 | 30.00 |
| 1269 | C | ALA | 174 | 139.608 | -9.765 | 23.791 | 1.00 | 30.00 |
| 1270 | O | ALA | 174 | 139.140 | -9.994 | 24.905 | 1.00 | 30.00 |
| 1271 | N | ALA | 175 | 140.005 | -8.555 | 23.411 | 1.00 | 30.00 |
| 1272 | CA | ALA | 175 | 139.942 | -7.419 | 24.320 | 1.00 | 30.00 |
| 1273 | CB | ALA | 175 | 141.293 | -6.720 | 24.361 | 1.00 | 30.00 |
| 1274 | C | ALA | 175 | 138.846 | -6.413 | 23.975 | 1.00 | 30.00 |
| 1275 | O | ALA | 175 | 138.473 | -5.586 | 24.813 | 1.00 | 30.00 |
| 1276 | N | ALA | 176 | 138.340 | -6.478 | 22.747 | 1.00 | 30.00 |
| 1277 | CA | ALA | 176 | 137.280 | -5.571 | 22.303 | 1.00 | 30.00 |
| 1278 | CB | ALA | 176 | 136.993 | -5.791 | 20.820 | 1.00 | 30.00 |
| 1279 | C | ALA | 176 | 136.008 | -5.793 | 23.121 | 1.00 | 30.00 |
| 1280 | O | ALA | 176 | 135.644 | -6.930 | 23.424 | 1.00 | 30.00 |
| 1281 | N | LYS | 177 | 135.335 | -4.705 | 23.477 | 1.00 | 30.00 |
| 1282 | CA | LYS | 177 | 134.109 | -4.799 | 24.261 | 1.00 | 30.00 |
| 1283 | CB | LYS | 177 | 134.317 | -4.198 | 25.657 | 1.00 | 30.00 |

39

| 1284 | CG | LYS | 177 | 135.482 | -4.803 | 26.441 | 1.00 | 30.00 |
|---|---|---|---|---|---|---|---|---|
| 1285 | CD | LYS | 177 | 135.295 | -6.299 | 26.688 | 1.00 | 30.00 |
| 1286 | CE | LYS | 177 | 136.544 | -6.934 | 27.302 | 1.00 | 30.00 |
| 1287 | NZ | LYS | 177 | 136.909 | -6.336 | 28.617 | 1.00 | 30.00 |
| 1288 | C | LYS | 177 | 132.949 | -4.094 | 23.567 | 1.00 | 30.00 |
| 1289 | O | LYS | 177 | 131.869 | -3.965 | 24.140 | 1.00 | 30.00 |
| 1290 | N | GLU | 178 | 133.170 | -3.643 | 22.334 | 1.00 | 30.00 |
| 1291 | CA | GLU | 178 | 132.126 | -2.956 | 21.576 | 1.00 | 30.00 |
| 1292 | CB | GLU | 178 | 132.611 | -2.617 | 20.167 | 1.00 | 30.00 |
| 1293 | CG | GLU | 178 | 134.115 | -2.568 | 20.020 | 1.00 | 30.00 |
| 1294 | CD | GLU | 178 | 134.757 | -1.544 | 20.915 | 1.00 | 30.00 |
| 1295 | OE1 | GLU | 178 | 134.268 | -0.396 | 20.936 | 1.00 | 30.00 |
| 1296 | OE2 | GLU | 178 | 135.752 | -1.881 | 21.591 | 1.00 | 30.00 |
| 1297 | C | GLU | 178 | 130.905 | -3.865 | 21.473 | 1.00 | 30.00 |
| 1298 | O | GLU | 178 | 130.967 | -5.045 | 21.819 | 1.00 | 30.00 |
| 1299 | N | ASP | 179 | 129.798 | -3.315 | 20.989 | 1.00 | 30.00 |
| 1300 | CA | ASP | 179 | 128.565 | -4.082 | 20.849 | 1.00 | 30.00 |
| 1301 | CB | ASP | 179 | 127.364 | -3.140 | 20.867 | 1.00 | 30.00 |
| 1302 | CG | ASP | 179 | 127.237 | -2.405 | 22.178 | 1.00 | 30.00 |
| 1303 | OD1 | ASP | 179 | 126.941 | -3.065 | 23.194 | 1.00 | 30.00 |
| 1304 | OD2 | ASP | 179 | 127.446 | -1.174 | 22.194 | 1.00 | 30.00 |
| 1305 | C | ASP | 179 | 128.570 | -4.901 | 19.570 | 1.00 | 30.00 |
| 1306 | O | ASP | 179 | 127.938 | -5.954 | 19.490 | 1.00 | 30.00 |
| 1307 | N | TYR | 180 | 129.273 | -4.404 | 18.562 | 1.00 | 30.00 |
| 1308 | CA | TYR | 180 | 129.385 | -5.112 | 17.297 | 1.00 | 30.00 |
| 1309 | CB | TYR | 180 | 128.662 | -4.369 | 16.169 | 1.00 | 30.00 |
| 1310 | CG | TYR | 180 | 127.155 | -4.304 | 16.271 | 1.00 | 30.00 |
| 1311 | CD1 | TYR | 180 | 126.531 | -3.507 | 17.232 | 1.00 | 30.00 |
| 1312 | CE1 | TYR | 180 | 125.138 | -3.406 | 17.294 | 1.00 | 30.00 |
| 1313 | CD2 | TYR | 180 | 126.349 | -5.007 | 15.376 | 1.00 | 30.00 |
| 1314 | CE2 | TYR | 180 | 124.958 | -4.916 | 15.428 | 1.00 | 30.00 |
| 1315 | CZ | TYR | 180 | 124.358 | -4.112 | 16.389 | 1.00 | 30.00 |
| 1316 | OH | TYR | 180 | 122.984 | -4.005 | 16.432 | 1.00 | 30.00 |
| 1317 | C | TYR | 180 | 130.865 | -5.199 | 16.949 | 1.00 | 30.00 |
| 1318 | O | TYR | 180 | 131.665 | -4.371 | 17.386 | 1.00 | 30.00 |
| 1319 | N | VAL | 181 | 131.229 | -6.212 | 16.173 | 1.00 | 30.00 |
| 1320 | CA | VAL | 181 | 132.607 | -6.373 | 15.742 | 1.00 | 30.00 |
| 1321 | CB | VAL | 181 | 133.387 | -7.348 | 16.637 | 1.00 | 30.00 |
| 1322 | CG1 | VAL | 181 | 134.814 | -7.478 | 16.122 | 1.00 | 30.00 |
| 1323 | CG2 | VAL | 181 | 133.380 | -6.855 | 18.085 | 1.00 | 30.00 |
| 1324 | C | VAL | 181 | 132.620 | -6.901 | 14.321 | 1.00 | 30.00 |
| 1325 | O | VAL | 181 | 132.172 | -8.011 | 14.063 | 1.00 | 30.00 |
| 1326 | N | LEU | 182 | 133.106 | -6.082 | 13.398 | 1.00 | 30.00 |
| 1327 | CA | LEU | 182 | 133.197 | -6.476 | 12.001 | 1.00 | 30.00 |
| 1328 | CB | LEU | 182 | 132.600 | -5.410 | 11.073 | 1.00 | 30.00 |
| 1329 | CG | LEU | 182 | 131.226 | -4.801 | 11.352 | 1.00 | 30.00 |
| 1330 | CD1 | LEU | 182 | 130.806 | -3.965 | 10.147 | 1.00 | 30.00 |
| 1331 | CD2 | LEU | 182 | 130.221 | -5.878 | 11.634 | 1.00 | 30.00 |
| 1332 | C | LEU | 182 | 134.673 | -6.641 | 11.668 | 1.00 | 30.00 |
| 1333 | O | LEU | 182 | 135.527 | -6.020 | 12.298 | 1.00 | 30.00 |
| 1334 | N | VAL | 183 | 134.958 | -7.491 | 10.687 | 1.00 | 30.00 |
| 1335 | CA | VAL | 183 | 136.315 | -7.747 | 10.233 | 1.00 | 30.00 |

40

| 1336 | CB | VAL | 183 | 136.854 | -9.103 | 10.758 | 1.00 | 30.00 |
| 1337 | CG1 | VAL | 183 | 138.276 | -9.327 | 10.273 | 1.00 | 30.00 |
| 1338 | CG2 | VAL | 183 | 136.805 | -9.135 | 12.278 | 1.00 | 30.00 |
| 1339 | C | VAL | 183 | 136.261 | -7.781 | 8.714 | 1.00 | 30.00 |
| 1340 | O | VAL | 183 | 135.375 | -8.391 | 8.128 | 1.00 | 30.00 |
| 1341 | N | ALA | 184 | 137.208 | -7.102 | 8.085 | 1.00 | 30.00 |
| 1342 | CA | ALA | 184 | 137.292 | -7.055 | 6.630 | 1.00 | 30.00 |
| 1343 | CB | ALA | 184 | 136.799 | -5.702 | 6.121 | 1.00 | 30.00 |
| 1344 | C | ALA | 184 | 138.741 | -7.296 | 6.186 | 1.00 | 30.00 |
| 1345 | O | ALA | 184 | 139.686 | -7.085 | 6.948 | 1.00 | 30.00 |
| 1346 | N | GLY | 185 | 138.891 | -7.753 | 4.951 | 1.00 | 30.00 |
| 1347 | CA | GLY | 185 | 140.199 | -8.032 | 4.375 | 1.00 | 30.00 |
| 1348 | C | GLY | 185 | 139.934 | -8.149 | 2.886 | 1.00 | 30.00 |
| 1349 | O | GLY | 185 | 138.784 | -7.988 | 2.468 | 1.00 | 30.00 |
| 1350 | N | HIS | 186 | 140.938 | -8.437 | 2.070 | 1.00 | 30.00 |
| 1351 | CA | HIS | 186 | 140.674 | -8.520 | 0.639 | 1.00 | 30.00 |
| 1352 | CB | HIS | 186 | 141.847 | -7.970 | -0.173 | 1.00 | 30.00 |
| 1353 | CG | HIS | 186 | 141.600 | -7.972 | -1.651 | 1.00 | 30.00 |
| 1354 | CD2 | HIS | 186 | 142.241 | -8.610 | -2.666 | 1.00 | 30.00 |
| 1355 | ND1 | HIS | 186 | 140.569 | -7.263 | -2.236 | 1.00 | 30.00 |
| 1356 | CE1 | HIS | 186 | 140.586 | -7.464 | -3.545 | 1.00 | 30.00 |
| 1357 | C | HIS | 186 | 140.358 | -9.915 | 0.146 | 1.00 | 30.00 |
| 1358 | O | HIS | 186 | 139.502 | -10.093 | -0.719 | 1.00 | 30.00 |
| 1359 | NE2 | HIS | 186 | 141.590 | -8.278 | -3.830 | 1.00 | 30.00 |
| 1360 | N | TYR | 187 | 141.057 | -10.904 | 0.685 | 1.00 | 30.00 |
| 1361 | CA | TYR | 187 | 140.844 | -12.288 | 0.279 | 1.00 | 30.00 |
| 1362 | CB | TYR | 187 | 142.073 | -13.136 | 0.621 | 1.00 | 30.00 |
| 1363 | CG | TYR | 187 | 143.290 | -12.814 | -0.215 | 1.00 | 30.00 |
| 1364 | CD1 | TYR | 187 | 144.579 | -13.007 | 0.293 | 1.00 | 30.00 |
| 1365 | CE1 | TYR | 187 | 145.703 | -12.715 | -0.470 | 1.00 | 30.00 |
| 1366 | CD2 | TYR | 187 | 143.157 | -12.321 | -1.517 | 1.00 | 30.00 |
| 1367 | CE2 | TYR | 187 | 144.271 | -12.029 | -2.289 | 1.00 | 30.00 |
| 1368 | CZ | TYR | 187 | 145.541 | -12.228 | -1.760 | 1.00 | 30.00 |
| 1369 | OH | TYR | 187 | 146.642 | -11.933 | -2.521 | 1.00 | 30.00 |
| 1370 | C | TYR | 187 | 139.622 | -12.850 | 0.978 | 1.00 | 30.00 |
| 1371 | O | TYR | 187 | 139.325 | -12.476 | 2.108 | 1.00 | 30.00 |
| 1372 | N | PRO | 188 | 138.891 | -13.758 | 0.307 | 1.00 | 30.00 |
| 1373 | CD | PRO | 188 | 139.083 | -14.166 | -1.099 | 1.00 | 30.00 |
| 1374 | CA | PRO | 188 | 137.684 | -14.385 | 0.868 | 1.00 | 30.00 |
| 1375 | CB | PRO | 188 | 136.974 | -14.968 | -0.363 | 1.00 | 30.00 |
| 1376 | CG | PRO | 188 | 137.672 | -14.331 | -1.565 | 1.00 | 30.00 |
| 1377 | C | PRO | 188 | 138.033 | -15.522 | 1.827 | 1.00 | 30.00 |
| 1378 | O | PRO | 188 | 139.082 | -16.152 | 1.695 | 1.00 | 30.00 |
| 1379 | N | ILE | 189 | 137.174 | -15.772 | 2.803 | 1.00 | 30.00 |
| 1380 | CA | ILE | 189 | 137.379 | -16.928 | 3.665 | 1.00 | 30.00 |
| 1381 | CB | ILE | 189 | 136.758 | -16.757 | 5.050 | 1.00 | 30.00 |
| 1382 | CG2 | ILE | 189 | 136.619 | -18.122 | 5.710 | 1.00 | 30.00 |
| 1383 | CG1 | ILE | 189 | 137.620 | -15.823 | 5.897 | 1.00 | 30.00 |
| 1384 | CD1 | ILE | 189 | 137.027 | -15.523 | 7.275 | 1.00 | 30.00 |
| 1385 | C | ILE | 189 | 136.534 | -17.933 | 2.871 | 1.00 | 30.00 |
| 1386 | O | ILE | 189 | 137.039 | -18.915 | 2.337 | 1.00 | 30.00 |
| 1387 | N | TRP | 190 | 135.240 | -17.632 | 2.779 | 1.00 | 30.00 |

| 1388 | CA | TRP | 190 | 134.279 | -18.429 | 2.018 | 1.00 | 30.00 |
| --- | --- | --- | --- | --- | --- | --- | --- | --- |
| 1389 | CB | TRP | 190 | 133.025 | -18.716 | 2.876 | 1.00 | 30.00 |
| 1390 | CG | TRP | 190 | 133.259 | -19.666 | 4.035 | 1.00 | 30.00 |
| 1391 | CD2 | TRP | 190 | 133.989 | -20.907 | 4.006 | 1.00 | 30.00 |
| 1392 | CE2 | TRP | 190 | 134.018 | -21.412 | 5.336 | 1.00 | 30.00 |
| 1393 | CE3 | TRP | 190 | 134.628 | -21.636 | 2.989 | 1.00 | 30.00 |
| 1394 | CD1 | TRP | 190 | 132.876 | -19.483 | 5.342 | 1.00 | 30.00 |
| 1395 | NE1 | TRP | 190 | 133.333 | -20.526 | 6.128 | 1.00 | 30.00 |
| 1396 | CZ2 | TRP | 190 | 134.661 | -22.613 | 5.673 | 1.00 | 30.00 |
| 1397 | CZ3 | TRP | 190 | 135.275 | -22.830 | 3.327 | 1.00 | 30.00 |
| 1398 | CH2 | TRP | 190 | 135.284 | -23.304 | 4.660 | 1.00 | 30.00 |
| 1399 | C | TRP | 190 | 133.880 | -17.666 | 0.727 | 1.00 | 30.00 |
| 1400 | O | TRP | 190 | 133.674 | -16.458 | 0.744 | 1.00 | 30.00 |
| 1401 | N | SER | 191 | 133.815 | -18.379 | -0.392 | 1.00 | 30.00 |
| 1402 | CA | SER | 191 | 133.412 | -17.811 | -1.682 | 1.00 | 30.00 |
| 1403 | CB | SER | 191 | 134.385 | -16.761 | -2.197 | 1.00 | 30.00 |
| 1404 | OG | SER | 191 | 134.220 | -16.645 | -3.612 | 1.00 | 30.00 |
| 1405 | C | SER | 191 | 133.360 | -18.904 | -2.717 | 1.00 | 30.00 |
| 1406 | O | SER | 191 | 134.293 | -19.688 | -2.834 | 1.00 | 30.00 |
| 1407 | N | ILE | 192 | 132.283 | -18.936 | -3.483 | 1.00 | 30.00 |
| 1408 | CA | ILE | 192 | 132.094 | -19.952 | -4.507 | 1.00 | 30.00 |
| 1409 | CB | ILE | 192 | 130.598 | -20.248 | -4.675 | 1.00 | 30.00 |
| 1410 | CG2 | ILE | 192 | 129.940 | -20.336 | -3.302 | 1.00 | 30.00 |
| 1411 | CG1 | ILE | 192 | 129.929 | -19.115 | -5.469 | 1.00 | 30.00 |
| 1412 | CD1 | ILE | 192 | 128.493 | -19.401 | -5.871 | 1.00 | 30.00 |
| 1413 | C | ILE | 192 | 132.647 | -19.536 | -5.874 | 1.00 | 30.00 |
| 1414 | O | ILE | 192 | 132.755 | -20.366 | -6.772 | 1.00 | 30.00 |
| 1415 | N | ALA | 193 | 133.001 | -18.258 | -6.017 | 1.00 | 30.00 |
| 1416 | CA | ALA | 193 | 133.485 | -17.719 | -7.283 | 1.00 | 30.00 |
| 1417 | CB | ALA | 193 | 133.495 | -16.214 | -7.205 | 1.00 | 30.00 |
| 1418 | C | ALA | 193 | 134.840 | -18.237 | -7.791 | 1.00 | 30.00 |
| 1419 | O | ALA | 193 | 135.352 | -19.245 | -7.306 | 1.00 | 30.00 |
| 1420 | N | GLU | 194 | 135.406 | -17.539 | -8.777 | 1.00 | 30.00 |
| 1421 | CA | GLU | 194 | 136.677 | -17.917 | -9.398 | 1.00 | 30.00 |
| 1422 | CB | GLU | 194 | 137.146 | -16.826 | -10.369 | 1.00 | 30.00 |
| 1423 | CG | GLU | 194 | 137.486 | -15.481 | -9.730 | 1.00 | 30.00 |
| 1424 | CD | GLU | 194 | 136.280 | -14.560 | -9.591 | 1.00 | 30.00 |
| 1425 | OE1 | GLU | 194 | 136.471 | -13.373 | -9.250 | 1.00 | 30.00 |
| 1426 | OE2 | GLU | 194 | 135.142 | -15.020 | -9.825 | 1.00 | 30.00 |
| 1427 | C | GLU | 194 | 137.827 | -18.259 | -8.462 | 1.00 | 30.00 |
| 1428 | O | GLU | 194 | 138.441 | -19.317 | -8.589 | 1.00 | 30.00 |
| 1429 | N | HIS | 195 | 138.145 | -17.369 | -7.534 | 1.00 | 30.00 |
| 1430 | CA | HIS | 195 | 139.244 | -17.643 | -6.612 | 1.00 | 30.00 |
| 1431 | CB | HIS | 195 | 139.721 | -16.346 | -5.935 | 1.00 | 30.00 |
| 1432 | CG | HIS | 195 | 140.440 | -15.415 | -6.862 | 1.00 | 30.00 |
| 1433 | CD2 | HIS | 195 | 140.164 | -14.146 | -7.247 | 1.00 | 30.00 |
| 1434 | ND1 | HIS | 195 | 141.578 | -15.782 | -7.547 | 1.00 | 30.00 |
| 1435 | CE1 | HIS | 195 | 141.970 | -14.782 | -8.316 | 1.00 | 30.00 |
| 1436 | NE2 | HIS | 195 | 141.128 | -13.778 | -8.151 | 1.00 | 30.00 |
| 1437 | C | HIS | 195 | 138.846 | -18.669 | -5.558 | 1.00 | 30.00 |
| 1438 | O | HIS | 195 | 139.588 | -19.619 | -5.288 | 1.00 | 30.00 |
| 1439 | N | GLY | 196 | 137.679 | -18.472 | -4.958 | 1.00 | 30.00 |

42

| 1440 | CA | GLY | 196 | 137.213 | -19.404 | -3.952 | 1.00 | 30.00 |
| 1441 | C | GLY | 196 | 137.798 | -19.203 | -2.568 | 1.00 | 30.00 |
| 1442 | O | GLY | 196 | 138.581 | -18.275 | -2.337 | 1.00 | 30.00 |
| 1443 | N | PRO | 197 | 137.430 | -20.076 | -1.615 | 1.00 | 30.00 |
| 1444 | CD | PRO | 197 | 136.673 | -21.331 | -1.793 | 1.00 | 30.00 |
| 1445 | CA | PRO | 197 | 137.937 | -19.972 | -0.246 | 1.00 | 30.00 |
| 1446 | CB | PRO | 197 | 137.502 | -21.293 | 0.393 | 1.00 | 30.00 |
| 1447 | CG | PRO | 197 | 136.282 | -21.670 | -0.373 | 1.00 | 30.00 |
| 1448 | C | PRO | 197 | 139.457 | -19.847 | -0.273 | 1.00 | 30.00 |
| 1449 | O | PRO | 197 | 140.126 | -20.400 | -1.159 | 1.00 | 30.00 |
| 1450 | N | THR | 198 | 140.011 | -19.119 | 0.684 | 1.00 | 30.00 |
| 1451 | CA | THR | 198 | 141.450 | -18.996 | 0.729 | 1.00 | 30.00 |
| 1452 | CB | THR | 198 | 141.880 | -17.510 | 0.871 | 1.00 | 30.00 |
| 1453 | OG1 | THR | 198 | 141.603 | -17.047 | 2.197 | 1.00 | 30.00 |
| 1454 | CG2 | THR | 198 | 141.108 | -16.645 | -0.151 | 1.00 | 30.00 |
| 1455 | C | THR | 198 | 141.863 | -19.847 | 1.921 | 1.00 | 30.00 |
| 1456 | O | THR | 198 | 141.487 | -19.567 | 3.061 | 1.00 | 30.00 |
| 1457 | N | ARG | 199 | 142.612 | -20.905 | 1.629 | 1.00 | 30.00 |
| 1458 | CA | ARG | 199 | 143.061 | -21.855 | 2.634 | 1.00 | 30.00 |
| 1459 | CB | ARG | 199 | 144.091 | -22.796 | 1.989 | 1.00 | 30.00 |
| 1460 | CG | ARG | 199 | 143.454 | -23.592 | 0.837 | 1.00 | 30.00 |
| 1461 | CD | ARG | 199 | 144.378 | -24.609 | 0.167 | 1.00 | 30.00 |
| 1462 | NE | ARG | 199 | 143.668 | -25.471 | -0.795 | 1.00 | 30.00 |
| 1463 | CZ | ARG | 199 | 143.106 | -25.057 | -1.932 | 1.00 | 30.00 |
| 1464 | NH1 | ARG | 199 | 143.155 | -23.775 | -2.282 | 1.00 | 30.00 |
| 1465 | NH2 | ARG | 199 | 142.502 | -25.930 | -2.734 | 1.00 | 30.00 |
| 1466 | C | ARG | 199 | 143.569 | -21.281 | 3.962 | 1.00 | 30.00 |
| 1467 | O | ARG | 199 | 143.074 | -21.644 | 5.029 | 1.00 | 30.00 |
| 1468 | N | CYS | 200 | 144.542 | -20.382 | 3.892 | 1.00 | 30.00 |
| 1469 | CA | CYS | 200 | 145.124 | -19.760 | 5.080 | 1.00 | 30.00 |
| 1470 | C | CYS | 200 | 144.099 | -18.998 | 5.939 | 1.00 | 30.00 |
| 1471 | O | CYS | 200 | 144.185 | -19.010 | 7.169 | 1.00 | 30.00 |
| 1472 | CB | CYS | 200 | 146.241 | -18.830 | 4.623 | 1.00 | 30.00 |
| 1473 | SG | CYS | 200 | 145.656 | -17.960 | 3.146 | 1.00 | 30.00 |
| 1474 | N | LEU | 201 | 143.133 | -18.334 | 5.304 | 1.00 | 30.00 |
| 1475 | CA | LEU | 201 | 142.121 | -17.593 | 6.055 | 1.00 | 30.00 |
| 1476 | CB | LEU | 201 | 141.377 | -16.611 | 5.142 | 1.00 | 30.00 |
| 1477 | CG | LEU | 201 | 142.167 | -15.346 | 4.776 | 1.00 | 30.00 |
| 1478 | CD1 | LEU | 201 | 141.322 | -14.450 | 3.894 | 1.00 | 30.00 |
| 1479 | CD2 | LEU | 201 | 142.566 | -14.605 | 6.038 | 1.00 | 30.00 |
| 1480 | C | LEU | 201 | 141.153 | -18.564 | 6.718 | 1.00 | 30.00 |
| 1481 | O | LEU | 201 | 140.834 | -18.424 | 7.900 | 1.00 | 30.00 |
| 1482 | N | VAL | 202 | 140.703 | -19.556 | 5.956 | 1.00 | 30.00 |
| 1483 | CA | VAL | 202 | 139.794 | -20.572 | 6.479 | 1.00 | 30.00 |
| 1484 | CB | VAL | 202 | 139.492 | -21.670 | 5.419 | 1.00 | 30.00 |
| 1485 | CG1 | VAL | 202 | 138.735 | -22.825 | 6.062 | 1.00 | 30.00 |
| 1486 | CG2 | VAL | 202 | 138.672 | -21.088 | 4.273 | 1.00 | 30.00 |
| 1487 | C | VAL | 202 | 140.426 | -21.253 | 7.693 | 1.00 | 30.00 |
| 1488 | O | VAL | 202 | 139.730 | -21.675 | 8.616 | 1.00 | 30.00 |
| 1489 | N | LYS | 203 | 141.751 | -21.347 | 7.689 | 1.00 | 30.00 |
| 1490 | CA | LYS | 203 | 142.473 | -21.995 | 8.777 | 1.00 | 30.00 |
| 1491 | CB | LYS | 203 | 143.752 | -22.667 | 8.244 | 1.00 | 30.00 |

| 1492 | CG | LYS | 203 | 144.508 | -23.477 | 9.302 | 1.00 | 30.00 |
| 1493 | CD | LYS | 203 | 145.749 | -24.188 | 8.759 | 1.00 | 30.00 |
| 1494 | CE | LYS | 203 | 146.871 | -23.221 | 8.415 | 1.00 | 30.00 |
| 1495 | NZ | LYS | 203 | 148.116 | -23.933 | 8.001 | 1.00 | 30.00 |
| 1496 | C | LYS | 203 | 142.847 | -21.082 | 9.934 | 1.00 | 30.00 |
| 1497 | O | LYS | 203 | 142.662 | -21.451 | 11.090 | 1.00 | 30.00 |
| 1498 | N | ASN | 204 | 143.364 | -19.896 | 9.619 | 1.00 | 30.00 |
| 1499 | CA | ASN | 204 | 143.814 | -18.948 | 10.641 | 1.00 | 30.00 |
| 1500 | CB | ASN | 204 | 145.122 | -18.284 | 10.187 | 1.00 | 30.00 |
| 1501 | CG | ASN | 204 | 146.280 | -19.264 | 10.100 | 1.00 | 30.00 |
| 1502 | OD1 | ASN | 204 | 146.333 | -20.111 | 9.210 | 1.00 | 30.00 |
| 1503 | ND2 | ASN | 204 | 147.215 | -19.152 | 11.032 | 1.00 | 30.00 |
| 1504 | C | ASN | 204 | 142.836 | -17.859 | 11.089 | 1.00 | 30.00 |
| 1505 | O | ASN | 204 | 142.852 | -17.450 | 12.261 | 1.00 | 30.00 |
| 1506 | N | LEU | 205 | 141.993 | -17.380 | 10.177 | 1.00 | 30.00 |
| 1507 | CA | LEU | 205 | 141.039 | -16.341 | 10.539 | 1.00 | 30.00 |
| 1508 | CB | LEU | 205 | 140.860 | -15.369 | 9.369 | 1.00 | 30.00 |
| 1509 | CG | LEU | 205 | 140.120 | -14.057 | 9.684 | 1.00 | 30.00 |
| 1510 | CD1 | LEU | 205 | 140.730 | -13.400 | 10.925 | 1.00 | 30.00 |
| 1511 | CD2 | LEU | 205 | 140.189 | -13.117 | 8.482 | 1.00 | 30.00 |
| 1512 | C | LEU | 205 | 139.671 | -16.890 | 10.988 | 1.00 | 30.00 |
| 1513 | O | LEU | 205 | 139.238 | -16.639 | 12.121 | 1.00 | 30.00 |
| 1514 | N | ARG | 206 | 139.010 | -17.647 | 10.109 | 1.00 | 30.00 |
| 1515 | CA | ARG | 206 | 137.685 | -18.219 | 10.379 | 1.00 | 30.00 |
| 1516 | CB | ARG | 206 | 137.416 | -19.397 | 9.420 | 1.00 | 30.00 |
| 1517 | CG | ARG | 206 | 135.967 | -19.913 | 9.378 | 1.00 | 30.00 |
| 1518 | CD | ARG | 206 | 135.641 | -20.907 | 10.501 | 1.00 | 30.00 |
| 1519 | NE | ARG | 206 | 134.428 | -20.532 | 11.244 | 1.00 | 30.00 |
| 1520 | CZ | ARG | 206 | 133.168 | -20.750 | 10.854 | 1.00 | 30.00 |
| 1521 | NH1 | ARG | 206 | 132.896 | -21.367 | 9.700 | 1.00 | 30.00 |
| 1522 | NH2 | ARG | 206 | 132.170 | -20.327 | 11.630 | 1.00 | 30.00 |
| 1523 | C | ARG | 206 | 137.472 | -18.658 | 11.827 | 1.00 | 30.00 |
| 1524 | O | ARG | 206 | 136.425 | -18.392 | 12.418 | 1.00 | 30.00 |
| 1525 | N | PRO | 207 | 138.460 | -19.338 | 12.420 | 1.00 | 30.00 |
| 1526 | CD | PRO | 207 | 139.671 | -19.949 | 11.840 | 1.00 | 30.00 |
| 1527 | CA | PRO | 207 | 138.282 | -19.771 | 13.805 | 1.00 | 30.00 |
| 1528 | CB | PRO | 207 | 139.536 | -20.612 | 14.064 | 1.00 | 30.00 |
| 1529 | CG | PRO | 207 | 139.865 | -21.163 | 12.720 | 1.00 | 30.00 |
| 1530 | C | PRO | 207 | 138.152 | -18.614 | 14.796 | 1.00 | 30.00 |
| 1531 | O | PRO | 207 | 137.546 | -18.773 | 15.856 | 1.00 | 30.00 |
| 1532 | N | LEU | 208 | 138.713 | -17.455 | 14.443 | 1.00 | 30.00 |
| 1533 | CA | LEU | 208 | 138.699 | -16.277 | 15.314 | 1.00 | 30.00 |
| 1534 | CB | LEU | 208 | 139.862 | -15.352 | 14.959 | 1.00 | 30.00 |
| 1535 | CG | LEU | 208 | 141.283 | -15.825 | 15.270 | 1.00 | 30.00 |
| 1536 | CD1 | LEU | 208 | 142.285 | -14.752 | 14.868 | 1.00 | 30.00 |
| 1537 | CD2 | LEU | 208 | 141.402 | -16.125 | 16.753 | 1.00 | 30.00 |
| 1538 | C | LEU | 208 | 137.416 | -15.454 | 15.330 | 1.00 | 30.00 |
| 1539 | O | LEU | 208 | 137.194 | -14.667 | 16.255 | 1.00 | 30.00 |
| 1540 | N | LEU | 209 | 136.580 | -15.630 | 14.309 | 1.00 | 30.00 |
| 1541 | CA | LEU | 209 | 135.328 | -14.888 | 14.205 | 1.00 | 30.00 |
| 1542 | CB | LEU | 209 | 134.814 | -14.955 | 12.772 | 1.00 | 30.00 |
| 1543 | CG | LEU | 209 | 135.881 | -14.580 | 11.745 | 1.00 | 30.00 |

44

| 1544 | CD1 | LEU | 209 | 135.324 | −14.715 | 10.346 | 1.00 | 30.00 |
| 1545 | CD2 | LEU | 209 | 136.352 | −13.171 | 11.992 | 1.00 | 30.00 |
| 1546 | C | LEU | 209 | 134.277 | −15.434 | 15.164 | 1.00 | 30.00 |
| 1547 | O | LEU | 209 | 133.806 | −14.725 | 16.053 | 1.00 | 30.00 |
| 1548 | N | ALA | 210 | 133.912 | −16.698 | 14.987 | 1.00 | 30.00 |
| 1549 | CA | ALA | 210 | 132.923 | −17.319 | 15.860 | 1.00 | 30.00 |
| 1550 | CB | ALA | 210 | 132.571 | −18.711 | 15.344 | 1.00 | 30.00 |
| 1551 | C | ALA | 210 | 133.480 | −17.409 | 17.281 | 1.00 | 30.00 |
| 1552 | O | ALA | 210 | 132.732 | −17.387 | 18.257 | 1.00 | 30.00 |
| 1553 | N | ALA | 211 | 134.804 | −17.503 | 17.381 | 1.00 | 30.00 |
| 1554 | CA | ALA | 211 | 135.493 | −17.608 | 18.665 | 1.00 | 30.00 |
| 1555 | CB | ALA | 211 | 136.991 | −17.710 | 18.437 | 1.00 | 30.00 |
| 1556 | C | ALA | 211 | 135.198 | −16.444 | 19.595 | 1.00 | 30.00 |
| 1557 | O | ALA | 211 | 134.838 | −16.644 | 20.754 | 1.00 | 30.00 |
| 1558 | N | TYR | 212 | 135.366 | −15.227 | 19.084 | 1.00 | 30.00 |
| 1559 | CA | TYR | 212 | 135.127 | −14.029 | 19.878 | 1.00 | 30.00 |
| 1560 | CB | TYR | 212 | 136.335 | −13.093 | 19.807 | 1.00 | 30.00 |
| 1561 | CG | TYR | 212 | 137.606 | −13.734 | 20.315 | 1.00 | 30.00 |
| 1562 | CD1 | TYR | 212 | 138.496 | −14.353 | 19.434 | 1.00 | 30.00 |
| 1563 | CE1 | TYR | 212 | 139.648 | −14.980 | 19.902 | 1.00 | 30.00 |
| 1564 | CD2 | TYR | 212 | 137.902 | −13.758 | 21.678 | 1.00 | 30.00 |
| 1565 | CE2 | TYR | 212 | 139.051 | −14.386 | 22.156 | 1.00 | 30.00 |
| 1566 | CZ | TYR | 212 | 139.917 | −14.993 | 21.262 | 1.00 | 30.00 |
| 1567 | OH | TYR | 212 | 141.044 | −15.624 | 21.727 | 1.00 | 30.00 |
| 1568 | C | TYR | 212 | 133.868 | −13.290 | 19.462 | 1.00 | 30.00 |
| 1569 | O | TYR | 212 | 133.666 | −12.134 | 19.827 | 1.00 | 30.00 |
| 1570 | N | GLY | 213 | 133.028 | −13.966 | 18.688 | 1.00 | 30.00 |
| 1571 | CA | GLY | 213 | 131.764 | −13.387 | 18.268 | 1.00 | 30.00 |
| 1572 | C | GLY | 213 | 131.750 | −12.226 | 17.295 | 1.00 | 30.00 |
| 1573 | O | GLY | 213 | 131.070 | −11.229 | 17.541 | 1.00 | 30.00 |
| 1574 | N | VAL | 214 | 132.495 | −12.350 | 16.198 | 1.00 | 30.00 |
| 1575 | CA | VAL | 214 | 132.530 | −11.323 | 15.161 | 1.00 | 30.00 |
| 1576 | CB | VAL | 214 | 133.662 | −11.573 | 14.145 | 1.00 | 30.00 |
| 1577 | CG1 | VAL | 214 | 133.656 | −10.489 | 13.076 | 1.00 | 30.00 |
| 1578 | CG2 | VAL | 214 | 135.001 | −11.612 | 14.858 | 1.00 | 30.00 |
| 1579 | C | VAL | 214 | 131.196 | −11.434 | 14.432 | 1.00 | 30.00 |
| 1580 | O | VAL | 214 | 130.750 | −12.526 | 14.091 | 1.00 | 30.00 |
| 1581 | N | THR | 215 | 130.548 | −10.312 | 14.193 | 1.00 | 30.00 |
| 1582 | CA | THR | 215 | 129.266 | −10.367 | 13.529 | 1.00 | 30.00 |
| 1583 | CB | THR | 215 | 128.584 | −8.983 | 13.585 | 1.00 | 30.00 |
| 1584 | OG1 | THR | 215 | 128.647 | −8.493 | 14.931 | 1.00 | 30.00 |
| 1585 | CG2 | THR | 215 | 127.120 | −9.075 | 13.148 | 1.00 | 30.00 |
| 1586 | C | THR | 215 | 129.405 | −10.845 | 12.081 | 1.00 | 30.00 |
| 1587 | O | THR | 215 | 128.603 | −11.658 | 11.598 | 1.00 | 30.00 |
| 1588 | N | ALA | 216 | 130.434 | −10.366 | 11.390 | 1.00 | 30.00 |
| 1589 | CA | ALA | 216 | 130.596 | −10.756 | 10.004 | 1.00 | 30.00 |
| 1590 | CB | ALA | 216 | 129.511 | −10.108 | 9.165 | 1.00 | 30.00 |
| 1591 | C | ALA | 216 | 131.948 | −10.410 | 9.422 | 1.00 | 30.00 |
| 1592 | O | ALA | 216 | 132.696 | −9.602 | 9.972 | 1.00 | 30.00 |
| 1593 | N | TYR | 217 | 132.239 | −11.032 | 8.284 | 1.00 | 30.00 |
| 1594 | CA | TYR | 217 | 133.481 | −10.805 | 7.585 | 1.00 | 30.00 |
| 1595 | CB | TYR | 217 | 134.325 | −12.094 | 7.550 | 1.00 | 30.00 |

| | | | | | | | |
|---|---|---|---|---|---|---|---|
| 1596 | CG | TYR | 217 | 135.644 | -11.931 | 6.809 | 1.00 | 30.00 |
| 1597 | CD1 | TYR | 217 | 135.861 | -12.543 | 5.568 | 1.00 | 30.00 |
| 1598 | CE1 | TYR | 217 | 137.069 | -12.359 | 4.874 | 1.00 | 30.00 |
| 1599 | CD2 | TYR | 217 | 136.670 | -11.128 | 7.337 | 1.00 | 30.00 |
| 1600 | CE2 | TYR | 217 | 137.873 | -10.939 | 6.651 | 1.00 | 30.00 |
| 1601 | CZ | TYR | 217 | 138.065 | -11.555 | 5.427 | 1.00 | 30.00 |
| 1602 | OH | TYR | 217 | 139.262 | -11.370 | 4.775 | 1.00 | 30.00 |
| 1603 | C | TYR | 217 | 133.212 | -10.315 | 6.167 | 1.00 | 30.00 |
| 1604 | O | TYR | 217 | 132.676 | -11.048 | 5.321 | 1.00 | 30.00 |
| 1605 | N | LEU | 218 | 133.580 | -9.061 | 5.924 | 1.00 | 30.00 |
| 1606 | CA | LEU | 218 | 133.431 | -8.443 | 4.605 | 1.00 | 30.00 |
| 1607 | CB | LEU | 218 | 133.120 | -6.949 | 4.743 | 1.00 | 30.00 |
| 1608 | CG | LEU | 218 | 131.761 | -6.597 | 5.346 | 1.00 | 30.00 |
| 1609 | CD1 | LEU | 218 | 131.877 | -6.603 | 6.863 | 1.00 | 30.00 |
| 1610 | CD2 | LEU | 218 | 131.307 | -5.229 | 4.841 | 1.00 | 30.00 |
| 1611 | C | LEU | 218 | 134.726 | -8.628 | 3.801 | 1.00 | 30.00 |
| 1612 | O | LEU | 218 | 135.828 | -8.633 | 4.368 | 1.00 | 30.00 |
| 1613 | N | CYS | 219 | 134.597 | -8.772 | 2.484 | 1.00 | 30.00 |
| 1614 | CA | CYS | 219 | 135.773 | -8.964 | 1.647 | 1.00 | 30.00 |
| 1615 | CB | CYS | 219 | 136.290 | -10.381 | 1.809 | 1.00 | 30.00 |
| 1616 | SG | CYS | 219 | 135.239 | -11.548 | 0.914 | 1.00 | 30.00 |
| 1617 | C | CYS | 219 | 135.408 | -8.778 | 0.196 | 1.00 | 30.00 |
| 1618 | O | CYS | 219 | 134.240 | -8.640 | -0.132 | 1.00 | 30.00 |
| 1619 | N | GLY | 220 | 136.419 | -8.803 | -0.667 | 1.00 | 30.00 |
| 1620 | CA | GLY | 220 | 136.202 | -8.677 | -2.099 | 1.00 | 30.00 |
| 1621 | C | GLY | 220 | 137.001 | -9.764 | -2.785 | 1.00 | 30.00 |
| 1622 | O | GLY | 220 | 136.866 | -10.942 | -2.463 | 1.00 | 30.00 |
| 1623 | N | HIS | 221 | 137.834 | -9.365 | -3.734 | 1.00 | 30.00 |
| 1624 | CA | HIS | 221 | 138.707 | -10.281 | -4.466 | 1.00 | 30.00 |
| 1625 | CB | HIS | 221 | 139.428 | -11.218 | -3.496 | 1.00 | 30.00 |
| 1626 | CG | HIS | 221 | 140.569 | -11.953 | -4.123 | 1.00 | 30.00 |
| 1627 | CD2 | HIS | 221 | 140.852 | -13.274 | -4.192 | 1.00 | 30.00 |
| 1628 | CE1 | HIS | 221 | 142.405 | -12.203 | -5.314 | 1.00 | 30.00 |
| 1629 | NE2 | HIS | 221 | 141.996 | -13.403 | -4.941 | 1.00 | 30.00 |
| 1630 | C | HIS | 221 | 138.018 | -11.076 | -5.570 | 1.00 | 30.00 |
| 1631 | O | HIS | 221 | 138.525 | -11.148 | -6.690 | 1.00 | 30.00 |
| 1632 | ND1 | HIS | 221 | 141.561 | -11.309 | -4.831 | 1.00 | 30.00 |
| 1633 | N | ASP | 222 | 136.889 | -11.700 | -5.258 | 1.00 | 30.00 |
| 1634 | CA | ASP | 222 | 136.131 | -12.415 | -6.289 | 1.00 | 30.00 |
| 1635 | CB | ASP | 222 | 135.312 | -13.577 | -5.697 | 1.00 | 30.00 |
| 1636 | CG | ASP | 222 | 136.028 | -14.930 | -5.809 | 1.00 | 30.00 |
| 1637 | OD1 | ASP | 222 | 136.495 | -15.283 | -6.913 | 1.00 | 30.00 |
| 1638 | OD2 | ASP | 222 | 136.106 | -15.652 | -4.795 | 1.00 | 30.00 |
| 1639 | C | ASP | 222 | 135.200 | -11.354 | -6.884 | 1.00 | 30.00 |
| 1640 | O | ASP | 222 | 134.365 | -10.789 | -6.185 | 1.00 | 30.00 |
| 1641 | N | HIS | 223 | 135.371 | -11.072 | -8.169 | 1.00 | 30.00 |
| 1642 | CA | HIS | 223 | 134.584 | -10.057 | -8.854 | 1.00 | 30.00 |
| 1643 | CB | HIS | 223 | 135.226 | -9.784 | -10.209 | 1.00 | 30.00 |
| 1644 | CG | HIS | 223 | 136.643 | -9.312 | -10.105 | 1.00 | 30.00 |
| 1645 | CD2 | HIS | 223 | 137.364 | -8.906 | -9.030 | 1.00 | 30.00 |
| 1646 | ND1 | HIS | 223 | 137.479 | -9.192 | -11.195 | 1.00 | 30.00 |
| 1647 | CE1 | HIS | 223 | 138.650 | -8.733 | -10.798 | 1.00 | 30.00 |

| 1648 | C | HIS | 223 | 133.094 | -10.367 | -8.998 | 1.00 | 30.00 |
| 1649 | O | HIS | 223 | 132.600 | -10.700 | -10.077 | 1.00 | 30.00 |
| 1650 | NE2 | HIS | 223 | 138.607 | -8.551 | -9.491 | 1.00 | 30.00 |
| 1651 | N | ASN | 224 | 132.382 | -10.232 | -7.887 | 1.00 | 30.00 |
| 1652 | CA | ASN | 224 | 130.962 | -10.495 | -7.841 | 1.00 | 30.00 |
| 1653 | CB | ASN | 224 | 130.689 | -11.963 | -8.178 | 1.00 | 30.00 |
| 1654 | CG | ASN | 224 | 131.687 | -12.900 | -7.546 | 1.00 | 30.00 |
| 1655 | OD1 | ASN | 224 | 131.679 | -13.127 | -6.328 | 1.00 | 30.00 |
| 1656 | ND2 | ASN | 224 | 132.576 | -13.446 | -8.376 | 1.00 | 30.00 |
| 1657 | C | ASN | 224 | 130.363 | -10.145 | -6.487 | 1.00 | 30.00 |
| 1658 | O | ASN | 224 | 131.045 | -9.630 | -5.589 | 1.00 | 30.00 |
| 1659 | N | LEU | 225 | 129.071 | -10.424 | -6.360 | 1.00 | 30.00 |
| 1660 | CA | LEU | 225 | 128.332 | -10.136 | -5.147 | 1.00 | 30.00 |
| 1661 | CB | LEU | 225 | 127.138 | -9.236 | -5.462 | 1.00 | 30.00 |
| 1662 | CG | LEU | 225 | 127.419 | -7.867 | -6.069 | 1.00 | 30.00 |
| 1663 | CD1 | LEU | 225 | 126.093 | -7.224 | -6.506 | 1.00 | 30.00 |
| 1664 | CD2 | LEU | 225 | 128.169 | -7.004 | -5.041 | 1.00 | 30.00 |
| 1665 | C | LEU | 225 | 127.793 | -11.390 | -4.494 | 1.00 | 30.00 |
| 1666 | O | LEU | 225 | 127.072 | -12.155 | -5.141 | 1.00 | 30.00 |
| 1667 | N | GLN | 226 | 128.130 | -11.604 | -3.222 | 1.00 | 30.00 |
| 1668 | CA | GLN | 226 | 127.587 | -12.749 | -2.504 | 1.00 | 30.00 |
| 1669 | CB | GLN | 226 | 128.306 | -14.054 | -2.896 | 1.00 | 30.00 |
| 1670 | CG | GLN | 226 | 129.816 | -14.052 | -2.816 | 1.00 | 30.00 |
| 1671 | CD | GLN | 226 | 130.436 | -15.353 | -3.340 | 1.00 | 30.00 |
| 1672 | OE1 | GLN | 226 | 130.160 | -16.436 | -2.819 | 1.00 | 30.00 |
| 1673 | NE2 | GLN | 226 | 131.277 | -15.243 | -4.376 | 1.00 | 30.00 |
| 1674 | C | GLN | 226 | 127.532 | -12.612 | -0.993 | 1.00 | 30.00 |
| 1675 | O | GLN | 226 | 128.327 | -11.911 | -0.374 | 1.00 | 30.00 |
| 1676 | N | TYR | 227 | 126.542 | -13.270 | -0.416 | 1.00 | 30.00 |
| 1677 | CA | TYR | 227 | 126.356 | -13.289 | 1.024 | 1.00 | 30.00 |
| 1678 | CB | TYR | 227 | 125.038 | -12.643 | 1.444 | 1.00 | 30.00 |
| 1679 | CG | TYR | 227 | 124.859 | -12.683 | 2.938 | 1.00 | 30.00 |
| 1680 | CD1 | TYR | 227 | 125.603 | -11.837 | 3.758 | 1.00 | 30.00 |
| 1681 | CE1 | TYR | 227 | 125.540 | -11.931 | 5.144 | 1.00 | 30.00 |
| 1682 | CD2 | TYR | 227 | 124.025 | -13.629 | 3.541 | 1.00 | 30.00 |
| 1683 | CE2 | TYR | 227 | 123.951 | -13.739 | 4.931 | 1.00 | 30.00 |
| 1684 | CZ | TYR | 227 | 124.717 | -12.883 | 5.728 | 1.00 | 30.00 |
| 1685 | OH | TYR | 227 | 124.692 | -12.978 | 7.106 | 1.00 | 30.00 |
| 1686 | C | TYR | 227 | 126.317 | -14.748 | 1.436 | 1.00 | 30.00 |
| 1687 | O | TYR | 227 | 125.536 | -15.536 | 0.889 | 1.00 | 30.00 |
| 1688 | N | LEU | 228 | 127.168 | -15.102 | 2.391 | 1.00 | 30.00 |
| 1689 | CA | LEU | 228 | 127.233 | -16.463 | 2.898 | 1.00 | 30.00 |
| 1690 | CB | LEU | 228 | 128.627 | -17.073 | 2.665 | 1.00 | 30.00 |
| 1691 | CG | LEU | 228 | 129.261 | -17.170 | 1.268 | 1.00 | 30.00 |
| 1692 | CD1 | LEU | 228 | 128.490 | -18.145 | 0.408 | 1.00 | 30.00 |
| 1693 | CD2 | LEU | 228 | 129.304 | -15.804 | 0.616 | 1.00 | 30.00 |
| 1694 | C | LEU | 228 | 126.992 | -16.343 | 4.393 | 1.00 | 30.00 |
| 1695 | O | LEU | 228 | 127.055 | -15.239 | 4.943 | 1.00 | 30.00 |
| 1696 | N | GLN | 229 | 126.713 | -17.468 | 5.045 | 1.00 | 30.00 |
| 1697 | CA | GLN | 229 | 126.516 | -17.474 | 6.484 | 1.00 | 30.00 |
| 1698 | CB | GLN | 229 | 125.139 | -16.926 | 6.840 | 1.00 | 30.00 |
| 1699 | CG | GLN | 229 | 124.959 | -16.636 | 8.325 | 1.00 | 30.00 |

| 1700 | CD | GLN | 229 | 123.623 | -15.976 | 8.627 | 1.00 | 30.00 |
| --- | --- | --- | --- | --- | --- | --- | --- | --- |
| 1701 | OE1 | GLN | 229 | 123.123 | -16.036 | 9.754 | 1.00 | 30.00 |
| 1702 | NE2 | GLN | 229 | 123.045 | -15.330 | 7.621 | 1.00 | 30.00 |
| 1703 | C | GLN | 229 | 126.701 | -18.885 | 7.032 | 1.00 | 30.00 |
| 1704 | O | GLN | 229 | 126.024 | -19.824 | 6.610 | 1.00 | 30.00 |
| 1705 | N | ASP | 230 | 127.645 | -19.027 | 7.960 | 1.00 | 30.00 |
| 1706 | CA | ASP | 230 | 127.945 | -20.317 | 8.566 | 1.00 | 30.00 |
| 1707 | CB | ASP | 230 | 129.392 | -20.355 | 9.091 | 1.00 | 30.00 |
| 1708 | CG | ASP | 230 | 129.639 | -19.397 | 10.254 | 1.00 | 30.00 |
| 1709 | OD1 | ASP | 230 | 128.816 | -19.334 | 11.193 | 1.00 | 30.00 |
| 1710 | OD2 | ASP | 230 | 130.685 | -18.718 | 10.236 | 1.00 | 30.00 |
| 1711 | C | ASP | 230 | 126.977 | -20.656 | 9.688 | 1.00 | 30.00 |
| 1712 | O | ASP | 230 | 126.266 | -19.791 | 10.192 | 1.00 | 30.00 |
| 1713 | N | GLU | 231 | 126.972 | -21.923 | 10.084 | 1.00 | 30.00 |
| 1714 | CA | GLU | 231 | 126.084 | -22.414 | 11.131 | 1.00 | 30.00 |
| 1715 | CB | GLU | 231 | 126.209 | -23.938 | 11.261 | 1.00 | 30.00 |
| 1716 | CG | GLU | 231 | 127.331 | -24.426 | 12.192 | 1.00 | 30.00 |
| 1717 | CD | GLU | 231 | 128.726 | -24.414 | 11.563 | 1.00 | 30.00 |
| 1718 | OE1 | GLU | 231 | 129.687 | -24.792 | 12.277 | 1.00 | 30.00 |
| 1719 | OE2 | GLU | 231 | 128.859 | -24.043 | 10.372 | 1.00 | 30.00 |
| 1720 | C | GLU | 231 | 126.336 | -21.772 | 12.490 | 1.00 | 30.00 |
| 1721 | O | GLU | 231 | 125.765 | -22.191 | 13.494 | 1.00 | 30.00 |
| 1722 | N | ASN | 232 | 127.190 | -20.763 | 12.541 | 1.00 | 30.00 |
| 1723 | CA | ASN | 232 | 127.459 | -20.101 | 13.813 | 1.00 | 30.00 |
| 1724 | CB | ASN | 232 | 128.976 | -19.952 | 14.061 | 1.00 | 30.00 |
| 1725 | CG | ASN | 232 | 129.618 | -21.213 | 14.667 | 1.00 | 30.00 |
| 1726 | OD1 | ASN | 232 | 129.110 | -21.783 | 15.635 | 1.00 | 30.00 |
| 1727 | ND2 | ASN | 232 | 130.757 | -21.629 | 14.106 | 1.00 | 30.00 |
| 1728 | C | ASN | 232 | 126.801 | -18.726 | 13.826 | 1.00 | 30.00 |
| 1729 | O | ASN | 232 | 126.781 | -18.049 | 14.859 | 1.00 | 30.00 |
| 1730 | N | GLY | 233 | 126.259 | -18.321 | 12.680 | 1.00 | 30.00 |
| 1731 | CA | GLY | 233 | 125.627 | -17.015 | 12.587 | 1.00 | 30.00 |
| 1732 | C | GLY | 233 | 126.562 | -15.916 | 12.096 | 1.00 | 30.00 |
| 1733 | O | GLY | 233 | 126.131 | -14.797 | 11.827 | 1.00 | 30.00 |
| 1734 | N | VAL | 234 | 127.853 | -16.224 | 12.012 | 1.00 | 30.00 |
| 1735 | CA | VAL | 234 | 128.819 | -15.269 | 11.513 | 1.00 | 30.00 |
| 1736 | CB | VAL | 234 | 130.246 | -15.830 | 11.594 | 1.00 | 30.00 |
| 1737 | CG1 | VAL | 234 | 131.229 | -14.852 | 10.967 | 1.00 | 30.00 |
| 1738 | CG2 | VAL | 234 | 130.610 | -16.109 | 13.046 | 1.00 | 30.00 |
| 1739 | C | VAL | 234 | 128.415 | -15.136 | 10.059 | 1.00 | 30.00 |
| 1740 | O | VAL | 234 | 128.177 | -16.144 | 9.402 | 1.00 | 30.00 |
| 1741 | N | GLY | 235 | 128.310 | -13.905 | 9.565 | 1.00 | 30.00 |
| 1742 | CA | GLY | 235 | 127.917 | -13.703 | 8.183 | 1.00 | 30.00 |
| 1743 | C | GLY | 235 | 129.123 | -13.525 | 7.289 | 1.00 | 30.00 |
| 1744 | O | GLY | 235 | 130.205 | -13.208 | 7.768 | 1.00 | 30.00 |
| 1745 | N | TYR | 236 | 128.950 | -13.742 | 5.991 | 1.00 | 30.00 |
| 1746 | CA | TYR | 236 | 130.054 | -13.565 | 5.060 | 1.00 | 30.00 |
| 1747 | CB | TYR | 236 | 130.583 | -14.922 | 4.593 | 1.00 | 30.00 |
| 1748 | CG | TYR | 236 | 131.222 | -15.674 | 5.729 | 1.00 | 30.00 |
| 1749 | CD1 | TYR | 236 | 130.446 | -16.427 | 6.616 | 1.00 | 30.00 |
| 1750 | CE1 | TYR | 236 | 131.017 | -17.035 | 7.741 | 1.00 | 30.00 |
| 1751 | CD2 | TYR | 236 | 132.586 | -15.551 | 5.989 | 1.00 | 30.00 |

| 1752 | CE2 | TYR | 236 | 133.166 | -16.154 | 7.110 | 1.00 | 30.00 |
|------|-----|-----|-----|---------|---------|-------|------|-------|
| 1753 | CZ | TYR | 236 | 132.375 | -16.891 | 7.982 | 1.00 | 30.00 |
| 1754 | OH | TYR | 236 | 132.935 | -17.463 | 9.096 | 1.00 | 30.00 |
| 1755 | C | TYR | 236 | 129.642 | -12.703 | 3.885 | 1.00 | 30.00 |
| 1756 | O | TYR | 236 | 129.013 | -13.170 | 2.941 | 1.00 | 30.00 |
| 1757 | N | VAL | 237 | 130.020 | -11.431 | 3.973 | 1.00 | 30.00 |
| 1758 | CA | VAL | 237 | 129.707 | -10.414 | 2.972 | 1.00 | 30.00 |
| 1759 | CB | VAL | 237 | 129.462 | -9.038 | 3.652 | 1.00 | 30.00 |
| 1760 | CG1 | VAL | 237 | 129.007 | -8.020 | 2.629 | 1.00 | 30.00 |
| 1761 | CG2 | VAL | 237 | 128.449 | -9.184 | 4.787 | 1.00 | 30.00 |
| 1762 | C | VAL | 237 | 130.835 | -10.241 | 1.965 | 1.00 | 30.00 |
| 1763 | O | VAL | 237 | 131.872 | -9.648 | 2.287 | 1.00 | 30.00 |
| 1764 | N | LEU | 238 | 130.633 | -10.762 | 0.754 | 1.00 | 30.00 |
| 1765 | CA | LEU | 238 | 131.630 | -10.646 | -0.316 | 1.00 | 30.00 |
| 1766 | CB | LEU | 238 | 131.894 | -12.014 | -0.955 | 1.00 | 30.00 |
| 1767 | CG | LEU | 238 | 133.043 | -12.164 | -1.967 | 1.00 | 30.00 |
| 1768 | CD1 | LEU | 238 | 133.514 | -13.624 | -1.980 | 1.00 | 30.00 |
| 1769 | CD2 | LEU | 238 | 132.598 | -11.710 | -3.360 | 1.00 | 30.00 |
| 1770 | C | LEU | 238 | 131.076 | -9.675 | -1.348 | 1.00 | 30.00 |
| 1771 | O | LEU | 238 | 130.206 | -10.025 | -2.149 | 1.00 | 30.00 |
| 1772 | N | SER | 239 | 131.589 | -8.452 | -1.325 | 1.00 | 30.00 |
| 1773 | CA | SER | 239 | 131.107 | -7.421 | -2.224 | 1.00 | 30.00 |
| 1774 | CB | SER | 239 | 130.406 | -6.335 | -1.419 | 1.00 | 30.00 |
| 1775 | OG | SER | 239 | 131.275 | -5.824 | -0.434 | 1.00 | 30.00 |
| 1776 | C | SER | 239 | 132.130 | -6.754 | -3.111 | 1.00 | 30.00 |
| 1777 | O | SER | 239 | 132.152 | -5.527 | -3.196 | 1.00 | 30.00 |
| 1778 | N | GLY | 240 | 132.950 | -7.537 | -3.795 | 1.00 | 30.00 |
| 1779 | CA | GLY | 240 | 133.948 | -6.934 | -4.654 | 1.00 | 30.00 |
| 1780 | C | GLY | 240 | 133.577 | -6.882 | -6.128 | 1.00 | 30.00 |
| 1781 | O | GLY | 240 | 134.156 | -7.592 | -6.947 | 1.00 | 30.00 |
| 1782 | N | ALA | 241 | 132.615 | -6.047 | -6.490 | 1.00 | 30.00 |
| 1783 | CA | ALA | 241 | 132.259 | -5.965 | -7.894 | 1.00 | 30.00 |
| 1784 | CB | ALA | 241 | 131.018 | -6.782 | -8.171 | 1.00 | 30.00 |
| 1785 | C | ALA | 241 | 132.047 | -4.532 | -8.330 | 1.00 | 30.00 |
| 1786 | O | ALA | 241 | 130.999 | -4.195 | -8.880 | 1.00 | 30.00 |
| 1787 | N | GLY | 242 | 133.052 | -3.691 | -8.097 | 1.00 | 30.00 |
| 1788 | CA | GLY | 242 | 132.946 | -2.294 | -8.479 | 1.00 | 30.00 |
| 1789 | C | GLY | 242 | 133.584 | -1.956 | -9.816 | 1.00 | 30.00 |
| 1790 | O | GLY | 242 | 133.362 | -0.877 | -10.355 | 1.00 | 30.00 |
| 1791 | N | ASN | 243 | 134.355 | -2.884 | -10.368 | 1.00 | 30.00 |
| 1792 | CA | ASN | 243 | 135.047 | -2.649 | -11.629 | 1.00 | 30.00 |
| 1793 | CB | ASN | 243 | 136.534 | -2.396 | -11.338 | 1.00 | 30.00 |
| 1794 | CG | ASN | 243 | 137.336 | -2.086 | -12.578 | 1.00 | 30.00 |
| 1795 | OD1 | ASN | 243 | 136.956 | -1.239 | -13.372 | 1.00 | 30.00 |
| 1796 | ND2 | ASN | 243 | 138.464 | -2.761 | -12.741 | 1.00 | 30.00 |
| 1797 | C | ASN | 243 | 134.888 | -3.828 | -12.576 | 1.00 | 30.00 |
| 1798 | O | ASN | 243 | 134.721 | -3.649 | -13.788 | 1.00 | 30.00 |
| 1799 | N | PHE | 244 | 134.933 | -5.031 | -12.007 | 1.00 | 30.00 |
| 1800 | CA | PHE | 244 | 134.812 | -6.265 | -12.780 | 1.00 | 30.00 |
| 1801 | CB | PHE | 244 | 136.091 | -7.094 | -12.653 | 1.00 | 30.00 |
| 1802 | CG | PHE | 244 | 137.272 | -6.515 | -13.376 | 1.00 | 30.00 |
| 1803 | CD1 | PHE | 244 | 138.377 | -6.058 | -12.674 | 1.00 | 30.00 |

| 1804 | CD2 | PHE | 244 | 137.301 | -6.469 | -14.768 | 1.00 | 30.00 |
| --- | --- | --- | --- | --- | --- | --- | --- | --- |
| 1805 | CE1 | PHE | 244 | 139.498 | -5.568 | -13.348 | 1.00 | 30.00 |
| 1806 | CE2 | PHE | 244 | 138.418 | -5.981 | -15.452 | 1.00 | 30.00 |
| 1807 | CZ | PHE | 244 | 139.515 | -5.532 | -14.742 | 1.00 | 30.00 |
| 1808 | C | PHE | 244 | 133.628 | -7.133 | -12.352 | 1.00 | 30.00 |
| 1809 | O | PHE | 244 | 133.078 | -6.969 | -11.264 | 1.00 | 30.00 |
| 1810 | N | MET | 245 | 133.251 | -8.070 | -13.215 | 1.00 | 30.00 |
| 1811 | CA | MET | 245 | 132.142 | -8.979 | -12.928 | 1.00 | 30.00 |
| 1812 | CB | MET | 245 | 130.871 | -8.455 | -13.589 | 1.00 | 30.00 |
| 1813 | CG | MET | 245 | 129.600 | -8.954 | -12.957 | 1.00 | 30.00 |
| 1814 | SD | MET | 245 | 129.286 | -8.191 | -11.360 | 1.00 | 30.00 |
| 1815 | CE | MET | 245 | 127.683 | -8.994 | -10.925 | 1.00 | 30.00 |
| 1816 | C | MET | 245 | 132.454 | -10.396 | -13.438 | 1.00 | 30.00 |
| 1817 | O | MET | 245 | 132.554 | -10.618 | -14.652 | 1.00 | 30.00 |
| 1818 | N | ASP | 246 | 132.614 | -11.348 | -12.518 | 1.00 | 30.00 |
| 1819 | CA | ASP | 246 | 132.922 | -12.731 | -12.895 | 1.00 | 30.00 |
| 1820 | CB | ASP | 246 | 134.202 | -13.206 | -12.208 | 1.00 | 30.00 |
| 1821 | CG | ASP | 246 | 134.865 | -14.347 | -12.954 | 1.00 | 30.00 |
| 1822 | OD1 | ASP | 246 | 134.137 | -15.186 | -13.518 | 1.00 | 30.00 |
| 1823 | OD2 | ASP | 246 | 136.111 | -14.411 | -12.976 | 1.00 | 30.00 |
| 1824 | C | ASP | 246 | 131.779 | -13.695 | -12.554 | 1.00 | 30.00 |
| 1825 | O | ASP | 246 | 131.413 | -13.852 | -11.388 | 1.00 | 30.00 |
| 1826 | N | PRO | 247 | 131.226 | -14.375 | -13.579 | 1.00 | 30.00 |
| 1827 | CD | PRO | 247 | 131.698 | -14.248 | -14.971 | 1.00 | 30.00 |
| 1828 | CA | PRO | 247 | 130.117 | -15.342 | -13.503 | 1.00 | 30.00 |
| 1829 | CB | PRO | 247 | 129.630 | -15.395 | -14.941 | 1.00 | 30.00 |
| 1830 | CG | PRO | 247 | 130.911 | -15.335 | -15.688 | 1.00 | 30.00 |
| 1831 | C | PRO | 247 | 130.472 | -16.731 | -12.978 | 1.00 | 30.00 |
| 1832 | O | PRO | 247 | 129.604 | -17.595 | -12.851 | 1.00 | 30.00 |
| 1833 | N | SER | 248 | 131.751 | -16.928 | -12.672 | 1.00 | 30.00 |
| 1834 | CA | SER | 248 | 132.271 | -18.200 | -12.178 | 1.00 | 30.00 |
| 1835 | CB | SER | 248 | 133.805 | -18.182 | -12.182 | 1.00 | 30.00 |
| 1836 | OG | SER | 248 | 134.336 | -19.351 | -11.580 | 1.00 | 30.00 |
| 1837 | C | SER | 248 | 131.803 | -18.600 | -10.794 | 1.00 | 30.00 |
| 1838 | O | SER | 248 | 131.600 | -17.762 | -9.907 | 1.00 | 30.00 |
| 1839 | N | VAL | 249 | 131.649 | -19.911 | -10.638 | 1.00 | 30.00 |
| 1840 | CA | VAL | 249 | 131.251 | -20.535 | -9.388 | 1.00 | 30.00 |
| 1841 | CB | VAL | 249 | 129.738 | -20.802 | -9.339 | 1.00 | 30.00 |
| 1842 | CG1 | VAL | 249 | 128.988 | -19.485 | -9.256 | 1.00 | 30.00 |
| 1843 | CG2 | VAL | 249 | 129.306 | -21.586 | -10.563 | 1.00 | 30.00 |
| 1844 | C | VAL | 249 | 132.010 | -21.856 | -9.292 | 1.00 | 30.00 |
| 1845 | O | VAL | 249 | 131.524 | -22.821 | -8.714 | 1.00 | 30.00 |
| 1846 | N | ARG | 250 | 133.209 | -21.879 | -9.874 | 1.00 | 30.00 |
| 1847 | CA | ARG | 250 | 134.079 | -23.060 | -9.861 | 1.00 | 30.00 |
| 1848 | CB | ARG | 250 | 135.471 | -22.717 | -10.436 | 1.00 | 30.00 |
| 1849 | CG | ARG | 250 | 136.529 | -23.804 | -10.197 | 1.00 | 30.00 |
| 1850 | CD | ARG | 250 | 137.978 | -23.325 | -10.392 | 1.00 | 30.00 |
| 1851 | NE | ARG | 250 | 138.934 | -24.197 | -9.695 | 1.00 | 30.00 |
| 1852 | CZ | ARG | 250 | 140.247 | -23.978 | -9.602 | 1.00 | 30.00 |
| 1853 | NH1 | ARG | 250 | 140.785 | -22.908 | -10.168 | 1.00 | 30.00 |
| 1854 | NH2 | ARG | 250 | 141.021 | -24.814 | -8.915 | 1.00 | 30.00 |
| 1855 | C | ARG | 250 | 134.262 | -23.628 | -8.456 | 1.00 | 30.00 |

| 1856 | O | ARG | 250 | 134.596 | -24.799 | -8.296 | 1.00 | 30.00 |
|------|-----|-----|-----|---------|---------|--------|------|-------|
| 1857 | N | HIS | 251 | 134.038 | -22.806 | -7.438 | 1.00 | 30.00 |
| 1858 | CA | HIS | 251 | 134.236 | -23.253 | -6.066 | 1.00 | 30.00 |
| 1859 | CB | HIS | 251 | 135.179 | -22.289 | -5.358 | 1.00 | 30.00 |
| 1860 | CG | HIS | 251 | 136.571 | -22.319 | -5.906 | 1.00 | 30.00 |
| 1861 | CD2 | HIS | 251 | 137.174 | -21.559 | -6.851 | 1.00 | 30.00 |
| 1862 | ND1 | HIS | 251 | 137.503 | -23.257 | -5.515 | 1.00 | 30.00 |
| 1863 | CE1 | HIS | 251 | 138.622 | -23.069 | -6.192 | 1.00 | 30.00 |
| 1864 | NE2 | HIS | 251 | 138.449 | -22.046 | -7.010 | 1.00 | 30.00 |
| 1865 | C | HIS | 251 | 132.995 | -23.468 | -5.226 | 1.00 | 30.00 |
| 1866 | O | HIS | 251 | 133.066 | -23.412 | -3.989 | 1.00 | 30.00 |
| 1867 | N | GLN | 252 | 131.865 | -23.715 | -5.893 | 1.00 | 30.00 |
| 1868 | CA | GLN | 252 | 130.599 | -23.967 | -5.203 | 1.00 | 30.00 |
| 1869 | CB | GLN | 252 | 129.506 | -24.409 | -6.173 | 1.00 | 30.00 |
| 1870 | CG | GLN | 252 | 129.231 | -23.492 | -7.322 | 1.00 | 30.00 |
| 1871 | CD | GLN | 252 | 127.829 | -23.682 | -7.849 | 1.00 | 30.00 |
| 1872 | OE1 | GLN | 252 | 126.858 | -23.206 | -7.240 | 1.00 | 30.00 |
| 1873 | NE2 | GLN | 252 | 127.705 | -24.393 | -8.971 | 1.00 | 30.00 |
| 1874 | C | GLN | 252 | 130.868 | -25.135 | -4.280 | 1.00 | 30.00 |
| 1875 | O | GLN | 252 | 130.550 | -25.100 | -3.090 | 1.00 | 30.00 |
| 1876 | N | ARG | 253 | 131.456 | -26.170 | -4.872 | 1.00 | 30.00 |
| 1877 | CA | ARG | 253 | 131.801 | -27.393 | -4.181 | 1.00 | 30.00 |
| 1878 | CB | ARG | 253 | 132.454 | -28.338 | -5.182 | 1.00 | 30.00 |
| 1879 | CG | ARG | 253 | 131.673 | -28.476 | -6.493 | 1.00 | 30.00 |
| 1880 | CD | ARG | 253 | 130.812 | -29.738 | -6.524 | 1.00 | 30.00 |
| 1881 | NE | ARG | 253 | 131.622 | -30.953 | -6.434 | 1.00 | 30.00 |
| 1882 | CZ | ARG | 253 | 131.141 | -32.190 | -6.528 | 1.00 | 30.00 |
| 1883 | NH1 | ARG | 253 | 129.844 | -32.387 | -6.719 | 1.00 | 30.00 |
| 1884 | NH2 | ARG | 253 | 131.958 | -33.230 | -6.424 | 1.00 | 30.00 |
| 1885 | C | ARG | 253 | 132.724 | -27.178 | -2.969 | 1.00 | 30.00 |
| 1886 | O | ARG | 253 | 132.654 | -27.932 | -2.002 | 1.00 | 30.00 |
| 1887 | N | LYS | 254 | 133.581 | -26.157 | -3.004 | 1.00 | 30.00 |
| 1888 | CA | LYS | 254 | 134.493 | -25.901 | -1.878 | 1.00 | 30.00 |
| 1889 | CB | LYS | 254 | 135.695 | -25.060 | -2.336 | 1.00 | 30.00 |
| 1890 | CG | LYS | 254 | 136.769 | -25.814 | -3.130 | 1.00 | 30.00 |
| 1891 | CD | LYS | 254 | 136.311 | -26.199 | -4.539 | 1.00 | 30.00 |
| 1892 | CE | LYS | 254 | 137.458 | -26.821 | -5.347 | 1.00 | 30.00 |
| 1893 | NZ | LYS | 254 | 137.063 | -27.165 | -6.748 | 1.00 | 30.00 |
| 1894 | C | LYS | 254 | 133.842 | -25.211 | -0.668 | 1.00 | 30.00 |
| 1895 | O | LYS | 254 | 134.478 | -25.062 | 0.379 | 1.00 | 30.00 |
| 1896 | N | VAL | 255 | 132.589 | -24.790 | -0.809 | 1.00 | 30.00 |
| 1897 | CA | VAL | 255 | 131.879 | -24.109 | 0.267 | 1.00 | 30.00 |
| 1898 | CB | VAL | 255 | 131.177 | -22.832 | -0.274 | 1.00 | 30.00 |
| 1899 | CG1 | VAL | 255 | 130.813 | -21.894 | 0.877 | 1.00 | 30.00 |
| 1900 | CG2 | VAL | 255 | 132.085 | -22.131 | -1.274 | 1.00 | 30.00 |
| 1901 | C | VAL | 255 | 130.840 | -25.069 | 0.867 | 1.00 | 30.00 |
| 1902 | O | VAL | 255 | 129.908 | -25.488 | 0.186 | 1.00 | 30.00 |
| 1903 | N | PRO | 256 | 130.982 | -25.412 | 2.162 | 1.00 | 30.00 |
| 1904 | CD | PRO | 256 | 131.865 | -24.738 | 3.134 | 1.00 | 30.00 |
| 1905 | CA | PRO | 256 | 130.066 | -26.330 | 2.851 | 1.00 | 30.00 |
| 1906 | CB | PRO | 256 | 130.598 | -26.338 | 4.289 | 1.00 | 30.00 |
| 1907 | CG | PRO | 256 | 131.153 | -24.984 | 4.452 | 1.00 | 30.00 |

| | | | | | | | |
|---|---|---|---|---|---|---|---|
| 1908 | C | PRO | 256 | 128.601 | -25.938 | 2.742 | 1.00 | 30.00 |
| 1909 | O | PRO | 256 | 128.167 | -24.939 | 3.312 | 1.00 | 30.00 |
| 1910 | N | ASN | 257 | 127.855 | -26.755 | 1.997 | 1.00 | 30.00 |
| 1911 | CA | ASN | 257 | 126.430 | -26.547 | 1.727 | 1.00 | 30.00 |
| 1912 | CB | ASN | 257 | 125.795 | -27.877 | 1.327 | 1.00 | 30.00 |
| 1913 | CG | ASN | 257 | 126.121 | -28.256 | -0.097 | 1.00 | 30.00 |
| 1914 | OD1 | ASN | 257 | 127.292 | -28.301 | -0.483 | 1.00 | 30.00 |
| 1915 | ND2 | ASN | 257 | 125.085 | -28.526 | -0.894 | 1.00 | 30.00 |
| 1916 | C | ASN | 257 | 125.588 | -25.869 | 2.805 | 1.00 | 30.00 |
| 1917 | O | ASN | 257 | 125.579 | -26.278 | 3.970 | 1.00 | 30.00 |
| 1918 | N | GLY | 258 | 124.866 | -24.833 | 2.387 | 1.00 | 30.00 |
| 1919 | CA | GLY | 258 | 124.038 | -24.089 | 3.311 | 1.00 | 30.00 |
| 1920 | C | GLY | 258 | 124.627 | -22.718 | 3.606 | 1.00 | 30.00 |
| 1921 | O | GLY | 258 | 123.922 | -21.826 | 4.095 | 1.00 | 30.00 |
| 1922 | N | TYR | 259 | 125.919 | -22.543 | 3.320 | 1.00 | 30.00 |
| 1923 | CA | TYR | 259 | 126.580 | -21.258 | 3.552 | 1.00 | 30.00 |
| 1924 | CB | TYR | 259 | 128.100 | -21.430 | 3.538 | 1.00 | 30.00 |
| 1925 | CG | TYR | 259 | 128.676 | -22.010 | 4.821 | 1.00 | 30.00 |
| 1926 | CD1 | TYR | 259 | 127.899 | -22.806 | 5.675 | 1.00 | 30.00 |
| 1927 | CE1 | TYR | 259 | 128.443 | -23.363 | 6.845 | 1.00 | 30.00 |
| 1928 | CD2 | TYR | 259 | 130.011 | -21.785 | 5.170 | 1.00 | 30.00 |
| 1929 | CE2 | TYR | 259 | 130.564 | -22.339 | 6.337 | 1.00 | 30.00 |
| 1930 | CZ | TYR | 259 | 129.773 | -23.125 | 7.166 | 1.00 | 30.00 |
| 1931 | OH | TYR | 259 | 130.320 | -23.670 | 8.304 | 1.00 | 30.00 |
| 1932 | C | TYR | 259 | 126.143 | -20.222 | 2.508 | 1.00 | 30.00 |
| 1933 | O | TYR | 259 | 125.874 | -19.063 | 2.851 | 1.00 | 30.00 |
| 1934 | N | LEU | 260 | 126.060 | -20.630 | 1.242 | 1.00 | 30.00 |
| 1935 | CA | LEU | 260 | 125.612 | -19.703 | 0.206 | 1.00 | 30.00 |
| 1936 | CB | LEU | 260 | 125.780 | -20.320 | -1.185 | 1.00 | 30.00 |
| 1937 | CG | LEU | 260 | 125.551 | -19.306 | -2.316 | 1.00 | 30.00 |
| 1938 | CD1 | LEU | 260 | 126.690 | -18.276 | -2.311 | 1.00 | 30.00 |
| 1939 | CD2 | LEU | 260 | 125.508 | -20.000 | -3.644 | 1.00 | 30.00 |
| 1940 | C | LEU | 260 | 124.137 | -19.329 | 0.401 | 1.00 | 30.00 |
| 1941 | O | LEU | 260 | 123.282 | -20.202 | 0.511 | 1.00 | 30.00 |
| 1942 | N | ARG | 261 | 123.837 | -18.039 | 0.458 | 1.00 | 30.00 |
| 1943 | CA | ARG | 261 | 122.453 | -17.592 | 0.625 | 1.00 | 30.00 |
| 1944 | CB | ARG | 261 | 122.263 | -16.788 | 1.914 | 1.00 | 30.00 |
| 1945 | CG | ARG | 261 | 122.729 | -17.470 | 3.169 | 1.00 | 30.00 |
| 1946 | CD | ARG | 261 | 122.154 | -18.850 | 3.277 | 1.00 | 30.00 |
| 1947 | NE | ARG | 261 | 122.851 | -19.577 | 4.326 | 1.00 | 30.00 |
| 1948 | CZ | ARG | 261 | 122.607 | -19.432 | 5.620 | 1.00 | 30.00 |
| 1949 | NH1 | ARG | 261 | 121.673 | -18.589 | 6.029 | 1.00 | 30.00 |
| 1950 | NH2 | ARG | 261 | 123.334 | -20.104 | 6.499 | 1.00 | 30.00 |
| 1951 | C | ARG | 261 | 122.114 | -16.689 | -0.532 | 1.00 | 30.00 |
| 1952 | O | ARG | 261 | 120.952 | -16.549 | -0.904 | 1.00 | 30.00 |
| 1953 | N | PHE | 262 | 123.144 | -16.061 | -1.085 | 1.00 | 30.00 |
| 1954 | CA | PHE | 262 | 122.956 | -15.153 | -2.201 | 1.00 | 30.00 |
| 1955 | CB | PHE | 262 | 122.520 | -13.777 | -1.705 | 1.00 | 30.00 |
| 1956 | CG | PHE | 262 | 122.500 | -12.741 | -2.787 | 1.00 | 30.00 |
| 1957 | CD1 | PHE | 262 | 121.529 | -12.780 | -3.784 | 1.00 | 30.00 |
| 1958 | CD2 | PHE | 262 | 123.485 | -11.766 | -2.848 | 1.00 | 30.00 |
| 1959 | CE1 | PHE | 262 | 121.537 | -11.868 | -4.831 | 1.00 | 30.00 |

52

| | | | | | | | | |
|---|---|---|---|---|---|---|---|---|
| 1960 | CE2 | PHE | 262 | 123.504 | -10.847 | -3.890 | 1.00 | 30.00 |
| 1961 | CZ | PHE | 262 | 122.522 | -10.902 | -4.889 | 1.00 | 30.00 |
| 1962 | C | PHE | 262 | 124.204 | -14.975 | -3.039 | 1.00 | 30.00 |
| 1963 | O | PHE | 262 | 125.292 | -14.793 | -2.505 | 1.00 | 30.00 |
| 1964 | N | HIS | 263 | 124.041 | -15.018 | -4.357 | 1.00 | 30.00 |
| 1965 | CA | HIS | 263 | 125.169 | -14.811 | -5.255 | 1.00 | 30.00 |
| 1966 | CB | HIS | 263 | 125.890 | -16.124 | -5.565 | 1.00 | 30.00 |
| 1967 | CG | HIS | 263 | 126.766 | -16.043 | -6.778 | 1.00 | 30.00 |
| 1968 | CD2 | HIS | 263 | 128.031 | -15.581 | -6.936 | 1.00 | 30.00 |
| 1969 | ND1 | HIS | 263 | 126.321 | -16.373 | -8.041 | 1.00 | 30.00 |
| 1970 | CE1 | HIS | 263 | 127.272 | -16.120 | -8.924 | 1.00 | 30.00 |
| 1971 | NE2 | HIS | 263 | 128.320 | -15.637 | -8.280 | 1.00 | 30.00 |
| 1972 | C | HIS | 263 | 124.764 | -14.155 | -6.573 | 1.00 | 30.00 |
| 1973 | O | HIS | 263 | 123.792 | -14.554 | -7.200 | 1.00 | 30.00 |
| 1974 | N | TYR | 264 | 125.517 | -13.143 | -6.984 | 1.00 | 30.00 |
| 1975 | CA | TYR | 264 | 125.240 | -12.476 | -8.248 | 1.00 | 30.00 |
| 1976 | CB | TYR | 264 | 124.353 | -11.244 | -8.054 | 1.00 | 30.00 |
| 1977 | CG | TYR | 264 | 123.858 | -10.680 | -9.370 | 1.00 | 30.00 |
| 1978 | CD1 | TYR | 264 | 123.208 | -11.502 | -10.298 | 1.00 | 30.00 |
| 1979 | CE1 | TYR | 264 | 122.759 | -11.000 | -11.520 | 1.00 | 30.00 |
| 1980 | CD2 | TYR | 264 | 124.046 | -9.336 | -9.698 | 1.00 | 30.00 |
| 1981 | CE2 | TYR | 264 | 123.599 | -8.821 | -10.919 | 1.00 | 30.00 |
| 1982 | CZ | TYR | 264 | 122.957 | -9.659 | -11.824 | 1.00 | 30.00 |
| 1983 | OH | TYR | 264 | 122.517 | -9.170 | -13.038 | 1.00 | 30.00 |
| 1984 | C | TYR | 264 | 126.539 | -12.062 | -8.929 | 1.00 | 30.00 |
| 1985 | O | TYR | 264 | 127.329 | -11.286 | -8.380 | 1.00 | 30.00 |
| 1986 | N | GLY | 265 | 126.756 | -12.590 | -10.128 | 1.00 | 30.00 |
| 1987 | CA | GLY | 265 | 127.957 | -12.268 | -10.868 | 1.00 | 30.00 |
| 1988 | C | GLY | 265 | 127.758 | -12.388 | -12.366 | 1.00 | 30.00 |
| 1989 | O | GLY | 265 | 128.688 | -12.746 | -13.089 | 1.00 | 30.00 |
| 1990 | N | SER | 266 | 126.554 | -12.070 | -12.839 | 1.00 | 30.00 |
| 1991 | CA | SER | 266 | 126.245 | -12.170 | -14.265 | 1.00 | 30.00 |
| 1992 | CB | SER | 266 | 124.791 | -11.766 | -14.537 | 1.00 | 30.00 |
| 1993 | OG | SER | 266 | 124.555 | -10.416 | -14.184 | 1.00 | 30.00 |
| 1994 | C | SER | 266 | 127.172 | -11.354 | -15.155 | 1.00 | 30.00 |
| 1995 | O | SER | 266 | 127.695 | -10.312 | -14.759 | 1.00 | 30.00 |
| 1996 | N | GLU | 267 | 127.356 | -11.850 | -16.371 | 1.00 | 30.00 |
| 1997 | CA | GLU | 267 | 128.213 | -11.214 | -17.359 | 1.00 | 30.00 |
| 1998 | CB | GLU | 267 | 128.339 | -12.140 | -18.579 | 1.00 | 30.00 |
| 1999 | CG | GLU | 267 | 129.504 | -11.844 | -19.507 | 1.00 | 30.00 |
| 2000 | CD | GLU | 267 | 130.824 | -12.342 | -18.958 | 1.00 | 30.00 |
| 2001 | OE1 | GLU | 267 | 131.209 | -11.920 | -17.846 | 1.00 | 30.00 |
| 2002 | OE2 | GLU | 267 | 131.478 | -13.159 | -19.642 | 1.00 | 30.00 |
| 2003 | C | GLU | 267 | 127.654 | -9.848 | -17.791 | 1.00 | 30.00 |
| 2004 | O | GLU | 267 | 128.330 | -8.826 | -17.687 | 1.00 | 30.00 |
| 2005 | N | ASP | 268 | 126.408 | -9.840 | -18.255 | 1.00 | 30.00 |
| 2006 | CA | ASP | 268 | 125.752 | -8.629 | -18.748 | 1.00 | 30.00 |
| 2007 | CB | ASP | 268 | 124.431 | -9.012 | -19.409 | 1.00 | 30.00 |
| 2008 | CG | ASP | 268 | 124.585 | -10.158 | -20.377 | 1.00 | 30.00 |
| 2009 | OD1 | ASP | 268 | 125.326 | -10.006 | -21.372 | 1.00 | 30.00 |
| 2010 | OD2 | ASP | 268 | 123.969 | -11.215 | -20.137 | 1.00 | 30.00 |
| 2011 | C | ASP | 268 | 125.496 | -7.504 | -17.751 | 1.00 | 30.00 |

| 2012 | O | ASP | 268 | 125.022 | -6.433 | -18.136 | 1.00 | 30.00 |
|------|-----|-----|-----|---------|--------|---------|------|-------|
| 2013 | N | SER | 269 | 125.798 | -7.732 | -16.480 | 1.00 | 30.00 |
| 2014 | CA | SER | 269 | 125.566 | -6.702 | -15.470 | 1.00 | 30.00 |
| 2015 | CB | SER | 269 | 125.150 | -7.345 | -14.149 | 1.00 | 30.00 |
| 2016 | OG | SER | 269 | 125.212 | -6.400 | -13.095 | 1.00 | 30.00 |
| 2017 | C | SER | 269 | 126.769 | -5.813 | -15.206 | 1.00 | 30.00 |
| 2018 | O | SER | 269 | 127.906 | -6.274 | -15.241 | 1.00 | 30.00 |
| 2019 | N | LEU | 270 | 126.520 | -4.533 | -14.947 | 1.00 | 30.00 |
| 2020 | CA | LEU | 270 | 127.618 | -3.627 | -14.628 | 1.00 | 30.00 |
| 2021 | CB | LEU | 270 | 127.188 | -2.157 | -14.737 | 1.00 | 30.00 |
| 2022 | CG | LEU | 270 | 127.051 | -1.524 | -16.126 | 1.00 | 30.00 |
| 2023 | CD1 | LEU | 270 | 126.647 | -0.079 | -15.954 | 1.00 | 30.00 |
| 2024 | CD2 | LEU | 270 | 128.363 | -1.617 | -16.901 | 1.00 | 30.00 |
| 2025 | C | LEU | 270 | 127.999 | -3.948 | -13.191 | 1.00 | 30.00 |
| 2026 | O | LEU | 270 | 127.828 | -5.081 | -12.729 | 1.00 | 30.00 |
| 2027 | N | GLY | 271 | 128.494 | -2.960 | -12.466 | 1.00 | 30.00 |
| 2028 | CA | GLY | 271 | 128.873 | -3.236 | -11.096 | 1.00 | 30.00 |
| 2029 | C | GLY | 271 | 127.784 | -3.716 | -10.140 | 1.00 | 30.00 |
| 2030 | O | GLY | 271 | 126.767 | -4.294 | -10.529 | 1.00 | 30.00 |
| 2031 | N | GLY | 272 | 128.047 | -3.449 | -8.863 | 1.00 | 30.00 |
| 2032 | CA | GLY | 272 | 127.168 | -3.797 | -7.767 | 1.00 | 30.00 |
| 2033 | C | GLY | 272 | 127.994 | -3.615 | -6.505 | 1.00 | 30.00 |
| 2034 | O | GLY | 272 | 129.220 | -3.694 | -6.556 | 1.00 | 30.00 |
| 2035 | N | PHE | 273 | 127.349 | -3.353 | -5.375 | 1.00 | 30.00 |
| 2036 | CA | PHE | 273 | 128.086 | -3.185 | -4.119 | 1.00 | 30.00 |
| 2037 | CB | PHE | 273 | 128.670 | -1.771 | -4.031 | 1.00 | 30.00 |
| 2038 | CG | PHE | 273 | 127.626 | -0.701 | -4.090 | 1.00 | 30.00 |
| 2039 | CD1 | PHE | 273 | 127.256 | -0.010 | -2.935 | 1.00 | 30.00 |
| 2040 | CD2 | PHE | 273 | 126.947 | -0.436 | -5.283 | 1.00 | 30.00 |
| 2041 | CE1 | PHE | 273 | 126.223 | 0.920 | -2.964 | 1.00 | 30.00 |
| 2042 | CE2 | PHE | 273 | 125.914 | 0.492 | -5.318 | 1.00 | 30.00 |
| 2043 | CZ | PHE | 273 | 125.550 | 1.168 | -4.159 | 1.00 | 30.00 |
| 2044 | C | PHE | 273 | 127.132 | -3.449 | -2.951 | 1.00 | 30.00 |
| 2045 | O | PHE | 273 | 126.010 | -3.898 | -3.162 | 1.00 | 30.00 |
| 2046 | N | THR | 274 | 127.578 | -3.172 | -1.728 | 1.00 | 30.00 |
| 2047 | CA | THR | 274 | 126.747 | -3.400 | -0.544 | 1.00 | 30.00 |
| 2048 | CB | THR | 274 | 127.368 | -4.510 | 0.406 | 1.00 | 30.00 |
| 2049 | OG1 | THR | 274 | 128.705 | -4.150 | 0.778 | 1.00 | 30.00 |
| 2050 | CG2 | THR | 274 | 127.401 | -5.860 | -0.276 | 1.00 | 30.00 |
| 2051 | C | THR | 274 | 126.522 | -2.132 | 0.285 | 1.00 | 30.00 |
| 2052 | O | THR | 274 | 127.349 | -1.209 | 0.292 | 1.00 | 30.00 |
| 2053 | N | TYR | 275 | 125.374 | -2.076 | 0.955 | 1.00 | 30.00 |
| 2054 | CA | TYR | 275 | 125.055 | -0.957 | 1.837 | 1.00 | 30.00 |
| 2055 | CB | TYR | 275 | 123.820 | -0.200 | 1.340 | 1.00 | 30.00 |
| 2056 | CG | TYR | 275 | 123.494 | 1.048 | 2.139 | 1.00 | 30.00 |
| 2057 | CD1 | TYR | 275 | 124.186 | 2.244 | 1.939 | 1.00 | 30.00 |
| 2058 | CE1 | TYR | 275 | 123.905 | 3.386 | 2.711 | 1.00 | 30.00 |
| 2059 | CD2 | TYR | 275 | 122.514 | 1.017 | 3.123 | 1.00 | 30.00 |
| 2060 | CE2 | TYR | 275 | 122.229 | 2.139 | 3.897 | 1.00 | 30.00 |
| 2061 | CZ | TYR | 275 | 122.921 | 3.319 | 3.692 | 1.00 | 30.00 |
| 2062 | OH | TYR | 275 | 122.608 | 4.404 | 4.485 | 1.00 | 30.00 |
| 2063 | C | TYR | 275 | 124.817 | -1.618 | 3.201 | 1.00 | 30.00 |

54

| 2064 | O | TYR | 275 | 124.151 | -2.649 | 3.290 | 1.00 | 30.00 |
| 2065 | N | VAL | 276 | 125.414 | -1.052 | 4.246 | 1.00 | 30.00 |
| 2066 | CA | VAL | 276 | 125.313 | -1.602 | 5.598 | 1.00 | 30.00 |
| 2067 | CB | VAL | 276 | 126.714 | -2.058 | 6.147 | 1.00 | 30.00 |
| 2068 | CG1 | VAL | 276 | 126.596 | -2.523 | 7.620 | 1.00 | 30.00 |
| 2069 | CG2 | VAL | 276 | 127.291 | -3.176 | 5.266 | 1.00 | 30.00 |
| 2070 | C | VAL | 276 | 124.766 | -0.555 | 6.544 | 1.00 | 30.00 |
| 2071 | O | VAL | 276 | 125.162 | 0.607 | 6.484 | 1.00 | 30.00 |
| 2072 | N | GLU | 277 | 123.871 | -0.982 | 7.429 | 1.00 | 30.00 |
| 2073 | CA | GLU | 277 | 123.261 | -0.081 | 8.393 | 1.00 | 30.00 |
| 2074 | CB | GLU | 277 | 121.884 | 0.349 | 7.886 | 1.00 | 30.00 |
| 2075 | CG | GLU | 277 | 121.353 | 1.621 | 8.500 | 1.00 | 30.00 |
| 2076 | CD | GLU | 277 | 119.977 | 1.975 | 7.989 | 1.00 | 30.00 |
| 2077 | OE1 | GLU | 277 | 119.756 | 1.890 | 6.764 | 1.00 | 30.00 |
| 2078 | OE2 | GLU | 277 | 119.118 | 2.343 | 8.809 | 1.00 | 30.00 |
| 2079 | C | GLU | 277 | 123.139 | -0.810 | 9.731 | 1.00 | 30.00 |
| 2080 | O | GLU | 277 | 122.320 | -1.712 | 9.888 | 1.00 | 30.00 |
| 2081 | N | ILE | 278 | 123.967 | -0.426 | 10.692 | 1.00 | 30.00 |
| 2082 | CA | ILE | 278 | 123.957 | -1.036 | 12.016 | 1.00 | 30.00 |
| 2083 | CB | ILE | 278 | 125.390 | -1.204 | 12.561 | 1.00 | 30.00 |
| 2084 | CG2 | ILE | 278 | 125.353 | -1.878 | 13.934 | 1.00 | 30.00 |
| 2085 | CG1 | ILE | 278 | 126.237 | -2.009 | 11.572 | 1.00 | 30.00 |
| 2086 | CD1 | ILE | 278 | 127.717 | -1.793 | 11.760 | 1.00 | 30.00 |
| 2087 | C | ILE | 278 | 123.194 | -0.142 | 12.987 | 1.00 | 30.00 |
| 2088 | O | ILE | 278 | 123.539 | 1.022 | 13.169 | 1.00 | 30.00 |
| 2089 | N | GLY | 279 | 122.158 | -0.696 | 13.607 | 1.00 | 30.00 |
| 2090 | CA | GLY | 279 | 121.369 | 0.068 | 14.552 | 1.00 | 30.00 |
| 2091 | C | GLY | 279 | 121.449 | -0.525 | 15.942 | 1.00 | 30.00 |
| 2092 | O | GLY | 279 | 122.274 | -1.396 | 16.205 | 1.00 | 30.00 |
| 2093 | N | SER | 280 | 120.583 | -0.051 | 16.832 | 1.00 | 30.00 |
| 2094 | CA | SER | 280 | 120.543 | -0.523 | 18.212 | 1.00 | 30.00 |
| 2095 | CB | SER | 280 | 119.455 | 0.236 | 18.982 | 1.00 | 30.00 |
| 2096 | OG | SER | 280 | 119.239 | -0.327 | 20.268 | 1.00 | 30.00 |
| 2097 | C | SER | 280 | 120.289 | -2.026 | 18.331 | 1.00 | 30.00 |
| 2098 | O | SER | 280 | 120.825 | -2.685 | 19.224 | 1.00 | 30.00 |
| 2099 | N | LYS | 281 | 119.481 | -2.561 | 17.421 | 1.00 | 30.00 |
| 2100 | CA | LYS | 281 | 119.124 | -3.970 | 17.458 | 1.00 | 30.00 |
| 2101 | CB | LYS | 281 | 117.613 | -4.112 | 17.253 | 1.00 | 30.00 |
| 2102 | CG | LYS | 281 | 116.776 | -3.451 | 18.343 | 1.00 | 30.00 |
| 2103 | CD | LYS | 281 | 117.091 | -4.039 | 19.712 | 1.00 | 30.00 |
| 2104 | CE | LYS | 281 | 116.171 | -3.493 | 20.796 | 1.00 | 30.00 |
| 2105 | NZ | LYS | 281 | 116.429 | -4.137 | 22.121 | 1.00 | 30.00 |
| 2106 | C | LYS | 281 | 119.859 | -4.887 | 16.488 | 1.00 | 30.00 |
| 2107 | O | LYS | 281 | 120.420 | -5.907 | 16.900 | 1.00 | 30.00 |
| 2108 | N | GLU | 282 | 119.855 | -4.553 | 15.203 | 1.00 | 30.00 |
| 2109 | CA | GLU | 282 | 120.540 | -5.402 | 14.237 | 1.00 | 30.00 |
| 2110 | CB | GLU | 282 | 119.533 | -6.283 | 13.493 | 1.00 | 30.00 |
| 2111 | CG | GLU | 282 | 118.810 | -5.602 | 12.339 | 1.00 | 30.00 |
| 2112 | CD | GLU | 282 | 117.700 | -4.680 | 12.798 | 1.00 | 30.00 |
| 2113 | OE1 | GLU | 282 | 116.703 | -5.180 | 13.365 | 1.00 | 30.00 |
| 2114 | OE2 | GLU | 282 | 117.820 | -3.456 | 12.588 | 1.00 | 30.00 |
| 2115 | C | GLU | 282 | 121.397 | -4.669 | 13.207 | 1.00 | 30.00 |

| | | | | | | | | |
|---|---|---|---|---|---|---|---|---|
| 2116 | O | GLU | 282 | 121.368 | -3.440 | 13.082 | 1.00 | 30.00 |
| 2117 | N | MET | 283 | 122.169 | -5.463 | 12.474 | 1.00 | 30.00 |
| 2118 | CA | MET | 283 | 123.031 | -4.971 | 11.414 | 1.00 | 30.00 |
| 2119 | CB | MET | 283 | 124.435 | -5.552 | 11.558 | 1.00 | 30.00 |
| 2120 | CG | MET | 283 | 125.332 | -5.228 | 10.386 | 1.00 | 30.00 |
| 2121 | SD | MET | 283 | 126.841 | -6.204 | 10.356 | 1.00 | 30.00 |
| 2122 | CE | MET | 283 | 127.318 | -6.048 | 8.590 | 1.00 | 30.00 |
| 2123 | C | MET | 283 | 122.418 | -5.457 | 10.109 | 1.00 | 30.00 |
| 2124 | O | MET | 283 | 122.173 | -6.649 | 9.945 | 1.00 | 30.00 |
| 2125 | N | SER | 284 | 122.160 | -4.543 | 9.185 | 1.00 | 30.00 |
| 2126 | CA | SER | 284 | 121.571 | -4.929 | 7.910 | 1.00 | 30.00 |
| 2127 | CB | SER | 284 | 120.336 | -4.072 | 7.631 | 1.00 | 30.00 |
| 2128 | OG | SER | 284 | 119.431 | -4.151 | 8.715 | 1.00 | 30.00 |
| 2129 | C | SER | 284 | 122.557 | -4.825 | 6.740 | 1.00 | 30.00 |
| 2130 | O | SER | 284 | 123.428 | -3.946 | 6.712 | 1.00 | 30.00 |
| 2131 | N | ILE | 285 | 122.414 | -5.736 | 5.783 | 1.00 | 30.00 |
| 2132 | CA | ILE | 285 | 123.275 | -5.747 | 4.610 | 1.00 | 30.00 |
| 2133 | CB | ILE | 285 | 124.279 | -6.950 | 4.592 | 1.00 | 30.00 |
| 2134 | CG2 | ILE | 285 | 125.247 | -6.785 | 3.415 | 1.00 | 30.00 |
| 2135 | CG1 | ILE | 285 | 125.045 | -7.063 | 5.915 | 1.00 | 30.00 |
| 2136 | CD1 | ILE | 285 | 124.275 | -7.786 | 6.995 | 1.00 | 30.00 |
| 2137 | C | ILE | 285 | 122.429 | -5.876 | 3.351 | 1.00 | 30.00 |
| 2138 | O | ILE | 285 | 122.011 | -6.974 | 2.989 | 1.00 | 30.00 |
| 2139 | N | THR | 286 | 122.159 | -4.770 | 2.677 | 1.00 | 30.00 |
| 2140 | CA | THR | 286 | 121.394 | -4.875 | 1.452 | 1.00 | 30.00 |
| 2141 | CB | THR | 286 | 120.231 | -3.824 | 1.415 | 1.00 | 30.00 |
| 2142 | OG1 | THR | 286 | 120.273 | -3.086 | 0.191 | 1.00 | 30.00 |
| 2143 | CG2 | THR | 286 | 120.298 | -2.895 | 2.637 | 1.00 | 30.00 |
| 2144 | C | THR | 286 | 122.383 | -4.734 | 0.290 | 1.00 | 30.00 |
| 2145 | O | THR | 286 | 123.282 | -3.903 | 0.323 | 1.00 | 30.00 |
| 2146 | N | TYR | 287 | 122.245 | -5.607 | -0.703 | 1.00 | 30.00 |
| 2147 | CA | TYR | 287 | 123.121 | -5.622 | -1.870 | 1.00 | 30.00 |
| 2148 | CB | TYR | 287 | 123.404 | -7.067 | -2.317 | 1.00 | 30.00 |
| 2149 | CG | TYR | 287 | 124.246 | -7.905 | -1.354 | 1.00 | 30.00 |
| 2150 | CD1 | TYR | 287 | 123.770 | -8.253 | -0.089 | 1.00 | 30.00 |
| 2151 | CE1 | TYR | 287 | 124.536 | -9.013 | 0.786 | 1.00 | 30.00 |
| 2152 | CD2 | TYR | 287 | 125.521 | -8.345 | -1.718 | 1.00 | 30.00 |
| 2153 | CE2 | TYR | 287 | 126.297 | -9.106 | -0.846 | 1.00 | 30.00 |
| 2154 | CZ | TYR | 287 | 125.800 | -9.436 | 0.406 | 1.00 | 30.00 |
| 2155 | OH | TYR | 287 | 126.573 | -10.177 | 1.275 | 1.00 | 30.00 |
| 2156 | C | TYR | 287 | 122.465 | -4.859 | -3.004 | 1.00 | 30.00 |
| 2157 | O | TYR | 287 | 121.387 | -5.227 | -3.476 | 1.00 | 30.00 |
| 2158 | N | VAL | 288 | 123.135 | -3.800 | -3.443 | 1.00 | 30.00 |
| 2159 | CA | VAL | 288 | 122.636 | -2.944 | -4.502 | 1.00 | 30.00 |
| 2160 | CB | VAL | 288 | 122.691 | -1.478 | -4.052 | 1.00 | 30.00 |
| 2161 | CG1 | VAL | 288 | 121.973 | -0.582 | -5.053 | 1.00 | 30.00 |
| 2162 | CG2 | VAL | 288 | 122.089 | -1.354 | -2.671 | 1.00 | 30.00 |
| 2163 | C | VAL | 288 | 123.425 | -3.090 | -5.799 | 1.00 | 30.00 |
| 2164 | O | VAL | 288 | 124.644 | -2.930 | -5.822 | 1.00 | 30.00 |
| 2165 | N | GLU | 289 | 122.728 | -3.393 | -6.885 | 1.00 | 30.00 |
| 2166 | CA | GLU | 289 | 123.381 | -3.528 | -8.181 | 1.00 | 30.00 |
| 2167 | CB | GLU | 289 | 122.439 | -4.201 | -9.174 | 1.00 | 30.00 |

56

| 2168 | CG | GLU | 289 | 122.987 | -4.310 | -10.577 | 1.00 | 30.00 |
| 2169 | CD | GLU | 289 | 122.177 | -5.263 | -11.422 | 1.00 | 30.00 |
| 2170 | OE1 | GLU | 289 | 120.933 | -5.234 | -11.300 | 1.00 | 30.00 |
| 2171 | OE2 | GLU | 289 | 122.777 | -6.035 | -12.206 | 1.00 | 30.00 |
| 2172 | C | GLU | 289 | 123.719 | -2.131 | -8.664 | 1.00 | 30.00 |
| 2173 | O | GLU | 289 | 123.151 | -1.154 | -8.182 | 1.00 | 30.00 |
| 2174 | N | ALA | 290 | 124.645 | -2.027 | -9.604 | 1.00 | 30.00 |
| 2175 | CA | ALA | 290 | 125.010 | -0.721 | -10.130 | 1.00 | 30.00 |
| 2176 | CB | ALA | 290 | 125.952 | -0.879 | -11.319 | 1.00 | 30.00 |
| 2177 | C | ALA | 290 | 123.738 | 0.018 | -10.553 | 1.00 | 30.00 |
| 2178 | O | ALA | 290 | 123.551 | 1.187 | -10.216 | 1.00 | 30.00 |
| 2179 | N | SER | 291 | 122.863 | -0.688 | -11.268 | 1.00 | 30.00 |
| 2180 | CA | SER | 291 | 121.587 | -0.156 | -11.771 | 1.00 | 30.00 |
| 2181 | CB | SER | 291 | 120.751 | -1.293 | -12.375 | 1.00 | 30.00 |
| 2182 | OG | SER | 291 | 121.347 | -1.801 | -13.560 | 1.00 | 30.00 |
| 2183 | C | SER | 291 | 120.716 | 0.617 | -10.775 | 1.00 | 30.00 |
| 2184 | O | SER | 291 | 120.020 | 1.551 | -11.159 | 1.00 | 30.00 |
| 2185 | N | GLY | 292 | 120.735 | 0.225 | -9.506 | 1.00 | 30.00 |
| 2186 | CA | GLY | 292 | 119.934 | 0.920 | -8.515 | 1.00 | 30.00 |
| 2187 | C | GLY | 292 | 119.005 | -0.015 | -7.767 | 1.00 | 30.00 |
| 2188 | O | GLY | 292 | 118.585 | 0.284 | -6.645 | 1.00 | 30.00 |
| 2189 | N | LYS | 293 | 118.688 | -1.151 | -8.392 | 1.00 | 30.00 |
| 2190 | CA | LYS | 293 | 117.806 | -2.161 | -7.808 | 1.00 | 30.00 |
| 2191 | CB | LYS | 293 | 117.471 | -3.258 | -8.829 | 1.00 | 30.00 |
| 2192 | CG | LYS | 293 | 116.586 | -2.862 | -9.990 | 1.00 | 30.00 |
| 2193 | CD | LYS | 293 | 116.208 | -4.106 | -10.789 | 1.00 | 30.00 |
| 2194 | CE | LYS | 293 | 115.212 | -3.795 | -11.896 | 1.00 | 30.00 |
| 2195 | NZ | LYS | 293 | 114.723 | -5.037 | -12.567 | 1.00 | 30.00 |
| 2196 | C | LYS | 293 | 118.444 | -2.859 | -6.623 | 1.00 | 30.00 |
| 2197 | O | LYS | 293 | 119.606 | -3.248 | -6.690 | 1.00 | 30.00 |
| 2198 | N | SER | 294 | 117.691 | -3.017 | -5.540 | 1.00 | 30.00 |
| 2199 | CA | SER | 294 | 118.201 | -3.755 | -4.392 | 1.00 | 30.00 |
| 2200 | CB | SER | 294 | 117.450 | -3.376 | -3.109 | 1.00 | 30.00 |
| 2201 | OG | SER | 294 | 117.750 | -2.043 | -2.715 | 1.00 | 30.00 |
| 2202 | C | SER | 294 | 117.899 | -5.204 | -4.777 | 1.00 | 30.00 |
| 2203 | O | SER | 294 | 116.743 | -5.552 | -4.989 | 1.00 | 30.00 |
| 2204 | N | LEU | 295 | 118.929 | -6.040 | -4.894 | 1.00 | 30.00 |
| 2205 | CA | LEU | 295 | 118.703 | -7.424 | -5.291 | 1.00 | 30.00 |
| 2206 | CB | LEU | 295 | 119.598 | -7.780 | -6.484 | 1.00 | 30.00 |
| 2207 | CG | LEU | 295 | 120.988 | -7.173 | -6.595 | 1.00 | 30.00 |
| 2208 | CD1 | LEU | 295 | 121.874 | -7.716 | -5.496 | 1.00 | 30.00 |
| 2209 | CD2 | LEU | 295 | 121.553 | -7.510 | -7.960 | 1.00 | 30.00 |
| 2210 | C | LEU | 295 | 118.804 | -8.494 | -4.202 | 1.00 | 30.00 |
| 2211 | O | LEU | 295 | 118.556 | -9.676 | -4.460 | 1.00 | 30.00 |
| 2212 | N | PHE | 296 | 119.152 | -8.075 | -2.988 | 1.00 | 30.00 |
| 2213 | CA | PHE | 296 | 119.234 | -8.987 | -1.847 | 1.00 | 30.00 |
| 2214 | CB | PHE | 296 | 120.343 | -10.021 | -2.023 | 1.00 | 30.00 |
| 2215 | CG | PHE | 296 | 120.420 | -11.019 | -0.888 | 1.00 | 30.00 |
| 2216 | CD1 | PHE | 296 | 119.628 | -12.167 | -0.893 | 1.00 | 30.00 |
| 2217 | CD2 | PHE | 296 | 121.268 | -10.803 | 0.194 | 1.00 | 30.00 |
| 2218 | CE1 | PHE | 296 | 119.682 | -13.083 | 0.164 | 1.00 | 30.00 |
| 2219 | CE2 | PHE | 296 | 121.326 | -11.718 | 1.258 | 1.00 | 30.00 |

57

| 2220 | CZ | PHE | 296 | 120.530 | -12.857 | 1.240 | 1.00 | 30.00 |
| 2221 | C | PHE | 296 | 119.491 | -8.260 | -0.539 | 1.00 | 30.00 |
| 2222 | O | PHE | 296 | 120.358 | -7.392 | -0.450 | 1.00 | 30.00 |
| 2223 | N | LYS | 297 | 118.737 | -8.626 | 0.486 | 1.00 | 30.00 |
| 2224 | CA | LYS | 297 | 118.935 | -8.029 | 1.794 | 1.00 | 30.00 |
| 2225 | CB | LYS | 297 | 117.933 | -6.903 | 2.049 | 1.00 | 30.00 |
| 2226 | CG | LYS | 297 | 118.033 | -6.324 | 3.451 | 1.00 | 30.00 |
| 2227 | CD | LYS | 297 | 117.144 | -5.106 | 3.640 | 1.00 | 30.00 |
| 2228 | CE | LYS | 297 | 117.398 | -4.442 | 4.990 | 1.00 | 30.00 |
| 2229 | NZ | LYS | 297 | 116.591 | -3.202 | 5.173 | 1.00 | 30.00 |
| 2230 | C | LYS | 297 | 118.770 | -9.093 | 2.857 | 1.00 | 30.00 |
| 2231 | O | LYS | 297 | 118.108 | -10.106 | 2.633 | 1.00 | 30.00 |
| 2232 | N | THR | 298 | 119.403 | -8.858 | 3.999 | 1.00 | 30.00 |
| 2233 | CA | THR | 298 | 119.336 | -9.738 | 5.159 | 1.00 | 30.00 |
| 2234 | CB | THR | 298 | 120.195 | -11.014 | 4.980 | 1.00 | 30.00 |
| 2235 | OG1 | THR | 298 | 120.207 | -11.758 | 6.203 | 1.00 | 30.00 |
| 2236 | CG2 | THR | 298 | 121.604 | -10.661 | 4.604 | 1.00 | 30.00 |
| 2237 | C | THR | 298 | 119.867 | -8.928 | 6.334 | 1.00 | 30.00 |
| 2238 | O | THR | 298 | 120.516 | -7.901 | 6.139 | 1.00 | 30.00 |
| 2239 | N | SER | 299 | 119.573 | -9.353 | 7.553 | 1.00 | 30.00 |
| 2240 | CA | SER | 299 | 120.074 | -8.627 | 8.709 | 1.00 | 30.00 |
| 2241 | CB | SER | 299 | 118.942 | -7.877 | 9.419 | 1.00 | 30.00 |
| 2242 | OG | SER | 299 | 118.130 | -8.758 | 10.169 | 1.00 | 30.00 |
| 2243 | C | SER | 299 | 120.734 | -9.612 | 9.663 | 1.00 | 30.00 |
| 2244 | O | SER | 299 | 120.458 | -10.819 | 9.626 | 1.00 | 30.00 |
| 2245 | N | LEU | 300 | 121.628 | -9.099 | 10.497 | 1.00 | 30.00 |
| 2246 | CA | LEU | 300 | 122.320 | -9.936 | 11.456 | 1.00 | 30.00 |
| 2247 | CB | LEU | 300 | 123.828 | -9.935 | 11.182 | 1.00 | 30.00 |
| 2248 | CG | LEU | 300 | 124.269 | -10.543 | 9.848 | 1.00 | 30.00 |
| 2249 | CD1 | LEU | 300 | 125.713 | -10.171 | 9.569 | 1.00 | 30.00 |
| 2250 | CD2 | LEU | 300 | 124.085 | -12.056 | 9.883 | 1.00 | 30.00 |
| 2251 | C | LEU | 300 | 122.045 | -9.438 | 12.862 | 1.00 | 30.00 |
| 2252 | O | LEU | 300 | 122.064 | -8.237 | 13.130 | 1.00 | 30.00 |
| 2253 | N | PRO | 301 | 121.778 | -10.365 | 13.784 | 1.00 | 30.00 |
| 2254 | CD | PRO | 301 | 121.729 | -11.825 | 13.589 | 1.00 | 30.00 |
| 2255 | CA | PRO | 301 | 121.498 | -10.008 | 15.175 | 1.00 | 30.00 |
| 2256 | CB | PRO | 301 | 121.090 | -11.345 | 15.792 | 1.00 | 30.00 |
| 2257 | CG | PRO | 301 | 121.893 | -12.338 | 15.000 | 1.00 | 30.00 |
| 2258 | C | PRO | 301 | 122.686 | -9.355 | 15.894 | 1.00 | 30.00 |
| 2259 | O | PRO | 301 | 123.832 | -9.452 | 15.453 | 1.00 | 30.00 |
| 2260 | N | ARG | 302 | 122.392 | -8.688 | 17.005 | 1.00 | 30.00 |
| 2261 | CA | ARG | 302 | 123.403 | -8.011 | 17.802 | 1.00 | 30.00 |
| 2262 | CB | ARG | 302 | 122.704 | -7.149 | 18.838 | 1.00 | 30.00 |
| 2263 | CG | ARG | 302 | 123.605 | -6.330 | 19.726 | 1.00 | 30.00 |
| 2264 | CD | ARG | 302 | 122.719 | -5.473 | 20.600 | 1.00 | 30.00 |
| 2265 | NE | ARG | 302 | 123.449 | -4.601 | 21.502 | 1.00 | 30.00 |
| 2266 | CZ | ARG | 302 | 122.862 | -3.884 | 22.451 | 1.00 | 30.00 |
| 2267 | NH1 | ARG | 302 | 121.547 | -3.947 | 22.605 | 1.00 | 30.00 |
| 2268 | NH2 | ARG | 302 | 123.586 | -3.107 | 23.244 | 1.00 | 30.00 |
| 2269 | C | ARG | 302 | 124.345 | -8.992 | 18.497 | 1.00 | 30.00 |
| 2270 | O | ARG | 302 | 125.529 | -9.056 | 18.097 | 1.00 | 30.00 |
| 2271 | OXT | ARG | 302 | 123.889 | -9.685 | 19.431 | 1.00 | 30.00 |

| 2272 | FE2 | FER | 401 | 141.993 | -9.359 | -5.779 | 1.00 | 30.00 |
| 2273 | FE3 | FER | 401 | 140.139 | -8.283 | -8.062 | 1.00 | 30.00 |
| 2274 | P | PO4 | 410 | 142.542 | -10.658 | -8.835 | 1.00 | 30.00 |
| 2275 | O1 | PO4 | 410 | 141.472 | -11.541 | -8.265 | 1.00 | 30.00 |
| 2276 | O2 | PO4 | 410 | 143.263 | -9.966 | -7.711 | 1.00 | 30.00 |
| 2277 | O3 | PO4 | 410 | 143.515 | -11.497 | -9.622 | 1.00 | 30.00 |
| 2278 | O4 | PO4 | 410 | 141.918 | -9.633 | -9.741 | 1.00 | 30.00 |
| 2279 | CA | NAG | 411 | 153.692 | 0.595 | -3.480 | 1.00 | 30.00 |
| 2280 | CB | NAG | 411 | 154.437 | 1.922 | -3.710 | 1.00 | 30.00 |
| 2281 | CG | NAG | 411 | 154.997 | 2.522 | -2.418 | 1.00 | 30.00 |
| 2282 | OD1 | NAG | 411 | 154.719 | 2.024 | -1.315 | 1.00 | 30.00 |
| 2283 | ND2 | NAG | 411 | 155.778 | 3.608 | -2.546 | 1.00 | 30.00 |
| 2284 | C1 | NAG | 411 | 156.642 | 4.226 | -1.276 | 1.00 | 30.00 |
| 2285 | C2 | NAG | 411 | 157.916 | 4.702 | -2.090 | 1.00 | 30.00 |
| 2286 | N2 | NAG | 411 | 158.724 | 3.468 | -2.158 | 1.00 | 30.00 |
| 2287 | C7 | NAG | 411 | 159.035 | 2.767 | -3.246 | 1.00 | 30.00 |
| 2288 | O7 | NAG | 411 | 158.697 | 3.082 | -4.393 | 1.00 | 30.00 |
| 2289 | C8 | NAG | 411 | 159.866 | 1.565 | -2.833 | 1.00 | 30.00 |
| 2290 | C3 | NAG | 411 | 158.760 | 5.825 | -1.380 | 1.00 | 30.00 |
| 2291 | O3 | NAG | 411 | 159.415 | 6.562 | -2.377 | 1.00 | 30.00 |
| 2292 | C4 | NAG | 411 | 157.957 | 6.889 | -0.596 | 1.00 | 30.00 |
| 2293 | O4 | NAG | 411 | 158.813 | 7.383 | 0.465 | 1.00 | 30.00 |
| 2294 | C5 | NAG | 411 | 156.488 | 6.285 | 0.011 | 1.00 | 30.00 |
| 2295 | O5 | NAG | 411 | 155.813 | 5.361 | -0.926 | 1.00 | 30.00 |
| 2296 | C6 | NAG | 411 | 155.414 | 7.426 | 0.254 | 1.00 | 30.00 |
| 2297 | O6 | NAG | 411 | 155.083 | 8.095 | -1.001 | 1.00 | 30.00 |

Non-amino acid residue names:
FER: Iron ions
NAG: N-acetylglucosamine, glycosylation
PO4: phosphate Non-standard atom names:
FE2: Iron with charge +2
FE3: Iron with charge +3

What is claimed is:

1. A method for structure-based drug design for a specific modulator, activator or inhibitor of TRAP (tartrate-resistant and purple acid phosphatase) activity, comprising generating a compound structure using a crystalline form of mammalian TRAP activated by cleavage prior to crystallization with a protease, wherein the crystalline form of the mammalian TRAP is capable of being used for X-ray studies, and wherein the crystalline form of the mammalian TRAP has a crystal structure with atomic structural coordinates as given in Table 2, or with coordinates having a root mean square deviation therefrom, with respect to conserved backbone atoms of the listed amino acid sequence, of not more than 1.5 Å.

2. The method according to claim 1, wherein the crystalline form of activated TRAP is human or rat TRAP.

3. The method according to claim 1, wherein the crystalline form of activated TRAP comprises heavy metals.

4. The method according to claim 3, wherein the heavy metals are Fe.

5. The method according to claim 1, wherein the crystalline TRAP has a conserved surface with a crystal structure which is created by atoms from two metal ions and from the following amino acid residues: Asp14, Asp52, Tyr55, Phe56, Asn91, His92, His186, Tyr187, Glu194, His195, His221, His223, Phe244, and Asp246.

6. The method according to claim 1, wherein the crystalline form of activated TRAP is prepared in the presence of inorganic phosphate.

7. The method according to claim 1, wherein the crystalline form of activated TRAP is grown using a reservoir containing 0.1 M KH2PO4.

8. The method according to claim 1, wherein the crystalline form of activated TRAP has a structure comprising a double beta sheet sandwich surrounded on both sides by alpha helices.

9. The method according to claim 8, wherein the double beta sheet sandwich has seven strands for each beta sheet.

10. The method according to claim 1, wherein the crystalline form of activated TRAP has a disulfide bridge between Cys142 and Cys200.

11. The method according to claim 1, wherein the crystalline form of activated TRAP comprises Fe2+ and Fe3+, wherein after cleavage of a 21 amino acid N-terminal signal peptide the mammalian TRAP comprises amino acid residues Tyr55, Asn91, His186, Asp14, Asp52, His221 and His223, and wherein Tyr55, Asn91 and His186 coordinate the Fe2+, Asp14 coordinates the Fe3+, and Asp52, His221 and His223 coordinate both the Fe2+ and the Fe3+.

12. The method according to claim 1, wherein the crystalline form of activated TRAP is prepared in the presence of salt.

13. The method of claim 1, further comprising
(a) generating a conserved surface of the crystalline form of activated TRAP on a computer screen;
(b) generating compounds having a spatial structure; and
(c) determining if the compounds from step (b) fit the conserved surface.

14. The method according to claim 13, wherein the crystalline form of activated TRAP is human or rat TRAP.

15. The method according to claim 13, wherein the crystalline form of activated TRAP comprises heavy metals.

16. The method according to claim 15, wherein the heavy metals are Fe.

17. The method according to claim 13, wherein the crystalline TRAP has a conserved surface with a crystal structure which is created by atoms from two metal ions and from the following amino acid residues: Asp14, Asp52, Tyr55, Phe56, Asn91, His92, His186, Tyr187, Glu194, His195, His221, His223, Phe244, and Asp246.

18. The method according to claim 13, wherein the crystalline form of activated TRAP is prepared in the presence of inorganic phosphate.

19. The method according to claim 13, wherein the crystalline form of activated TRAP is grown using a reservoir containing 0.1 M KH2PO4.

20. The method according to claim 13, wherein the crystalline form of activated TRAP has a structure comprising a double beta sheet sandwich surrounded on both sides by alpha helices.

21. The method according to claim 20, wherein the double beta sleet sandwich has seven strands for each beta sheet.

22. The method according to claim 13, wherein the crystalline form of activated TRAP has a disulfide bridge between Cys142 and Cys200.

23. The method according to claim 13, wherein the crystalline form of activated TRAP comprises Fe2+ and Fe3+, wherein after cleavage of a 21 amino acid N-terminal signal peptide the mammalian TRAP comprises amino acid residues Tyr55, Asn91, His186, Asp14, Asp52, His221 and His223, and wherein Tyr55, Asn91 and His186 coordinate the Fe2+, Asp14 coordinates the Fe3+, and Asp52, His221 and His223 coordinate both the Fe2+ and the Fe3+.

24. The method according to claim 13, wherein the crystalline form of activated TRAP is prepared in the presence of salt.

* * * * *